(12) United States Patent
Rodman et al.

(10) Patent No.: US 10,316,318 B2
(45) Date of Patent: *Jun. 11, 2019

(54) OLIGONUCLEOTIDE COMPOSITIONS AND USES THEREOF

(71) Applicant: MIRAGEN THERAPEUTICS, INC., Boulder, CO (US)

(72) Inventors: David Rodman, Boulder, CO (US); Anita Seto, Boulder, CO (US); Christina Dalby, Boulder, CO (US); Aimee Jackson, Boulder, CO (US); Xuan Beatty, Boulder, CO (US)

(73) Assignee: MIRAGEN THERAPEUTICS, INC., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/976,333

(22) Filed: May 10, 2018

(65) Prior Publication Data

US 2019/0106695 A1    Apr. 11, 2019

Related U.S. Application Data

(63) Continuation of application No. 15/714,671, filed on Sep. 25, 2017, now Pat. No. 9,994,852, which is a continuation of application No. PCT/US2016/035865, filed on Jun. 3, 2016.

(60) Provisional application No. 62/171,758, filed on Jun. 5, 2015.

(51) Int. Cl.
| | |
|---|---|
| *A61K 31/70* | (2006.01) |
| *C07H 21/02* | (2006.01) |
| *C07H 21/04* | (2006.01) |
| *C12N 15/113* | (2010.01) |
| *C12N 5/00* | (2006.01) |

(52) U.S. Cl.
CPC ...... *C12N 15/113* (2013.01); *C12N 2310/113* (2013.01); *C12N 2310/315* (2013.01); *C12N 2310/3231* (2013.01); *C12N 2310/344* (2013.01); *C12N 2320/31* (2013.01)

(58) Field of Classification Search
None
See application file for complete search history.

(56) References Cited

U.S. PATENT DOCUMENTS

| | | |
|---|---|---|
| 4,254,105 A | 3/1981 | Fukuda |
| 4,960,764 A | 10/1990 | Figueroa, Jr. et al. |
| 5,260,065 A | 11/1993 | Mathur et al. |
| 5,783,656 A | 7/1998 | Lee et al. |
| 5,837,533 A | 11/1998 | Boutin |
| 5,981,505 A | 11/1999 | Weiner et al. |
| 6,127,170 A | 10/2000 | Boutin |
| 6,217,900 B1 | 4/2001 | Ciccarelli et al. |
| 6,379,965 B1 | 4/2002 | Boutin |
| 6,383,512 B1 | 5/2002 | Ciccarelli et al. |
| 6,403,566 B1 | 6/2002 | Wang |
| 6,693,187 B1 | 2/2004 | Dellinger |
| 6,747,014 B2 | 6/2004 | Teng et al. |
| 6,838,283 B2 | 1/2005 | Bennett et al. |
| 7,067,641 B2 | 6/2006 | Dellinger |
| 7,202,227 B2 | 4/2007 | Boutin |
| 7,700,288 B2 | 4/2010 | Dahlberg et al. |
| 7,723,030 B2 | 5/2010 | Croce et al. |
| 7,838,660 B2 | 11/2010 | Tuschl et al. |
| 7,919,245 B2 | 4/2011 | Brown et al. |
| 7,943,318 B2 | 5/2011 | Croce et al. |
| 7,985,584 B2 | 7/2011 | Croce et al. |
| 7,993,831 B2 | 8/2011 | Latham et al. |
| 8,071,306 B2 | 12/2011 | Raymond |
| 8,106,025 B2 | 1/2012 | Bennett et al. |
| 8,163,708 B2 | 4/2012 | Elmen et al. |
| 8,354,224 B2 | 1/2013 | Croce et al. |
| 8,389,210 B2 | 3/2013 | Croce et al. |
| 8,404,659 B2 | 3/2013 | Kauppinen et al. |
| 8,465,918 B2 | 6/2013 | Croce |
| 8,492,357 B2 | 7/2013 | Worm et al. |
| 8,637,241 B2 | 1/2014 | Somasundaram et al. |
| 8,658,370 B2 | 2/2014 | Croce et al. |
| 8,664,192 B2 | 3/2014 | Croce |
| 8,685,946 B2 | 4/2014 | Hutvagner et al. |
| 8,697,672 B2 | 4/2014 | Baltimore et al. |
| 8,729,250 B2 | 5/2014 | Elmen et al. |
| 8,778,676 B2 | 7/2014 | Croce et al. |
| 8,911,936 B2 | 12/2014 | Croce et al. |
| 8,946,179 B2 | 2/2015 | Bennett et al. |

(Continued)

FOREIGN PATENT DOCUMENTS

| | | |
|---|---|---|
| EP | 2 390 328 A1 | 11/2011 |
| WO | WO-96/31194 A2 | 10/1996 |

(Continued)

OTHER PUBLICATIONS

Ballabio, E. et al. (2010). "MicroRNA expression in Sezary syndrome: identification, function, and diagnostic potential," *Blood* 116:1105-1113.

(Continued)

*Primary Examiner* — Sean McGarry

(74) *Attorney, Agent, or Firm* — Cooley LLP

(57) ABSTRACT

The present invention provides oligonucleotide inhibitors of miR-155 and compositions thereof. The invention further provides methods for treating cancer such as a T cell lymphoma in a subject by administering to the subject an oligonucleotide inhibitor of miR-155. The invention also provides methods for reducing or inhibiting the proliferation of malignant T cells by administering an oligonucleotide inhibitor of miR-155.

16 Claims, 34 Drawing Sheets

Specification includes a Sequence Listing.

(56) References Cited

U.S. PATENT DOCUMENTS

| | | | |
|---|---|---|---|
| 8,957,223 | B2 | 2/2015 | Manoharan et al. |
| 9,023,825 | B2 | 5/2015 | Croce et al. |
| 9,051,618 | B2 | 6/2015 | Croce et al. |
| 9,133,455 | B2 | 9/2015 | Elmen et al. |
| 9,150,859 | B2 | 10/2015 | Croce et al. |
| 9,290,761 | B2 | 3/2016 | Baltimore et al. |
| 9,315,810 | B2 | 4/2016 | Matsuda et al. |
| 9,334,497 | B2 | 5/2016 | Hutvagner et al. |
| 9,447,471 | B2 | 9/2016 | Qu et al. |
| 9,487,776 | B2 | 11/2016 | List et al. |
| 9,603,873 | B2 | 3/2017 | Caligiuri et al. |
| 9,771,585 | B2 | 9/2017 | Rodman et al. |
| 9,994,852 | B2 | 6/2018 | Rodman et al. |
| 2008/0300211 | A1 | 12/2008 | Baltimore et al. |
| 2009/0143326 | A1 | 6/2009 | Obad et al. |
| 2009/0298916 | A1 | 12/2009 | Kauppinen et al. |
| 2010/0004320 | A1 | 1/2010 | Elmen et al. |
| 2010/0203544 | A1 | 8/2010 | Croce et al. |
| 2010/0234241 | A1 | 9/2010 | Croce et al. |
| 2010/0286234 | A1 | 11/2010 | Elmen et al. |
| 2010/0286385 | A1 | 11/2010 | Tuschl et al. |
| 2010/0298410 | A1 | 11/2010 | Obad et al. |
| 2011/0021609 | A1 | 1/2011 | Croce et al. |
| 2011/0076322 | A1 | 3/2011 | Panzner et al. |
| 2011/0077288 | A1 | 3/2011 | Kauppinen et al. |
| 2012/0035248 | A9 | 2/2012 | Bennett et al. |
| 2012/0064122 | A1 | 3/2012 | Baltimore et al. |
| 2012/0128761 | A1 | 5/2012 | Vagle et al. |
| 2012/0157334 | A1 | 6/2012 | Beaudenon-Huibregtse et al. |
| 2012/0238618 | A1 | 9/2012 | Elmen et al. |
| 2012/0283114 | A1 | 11/2012 | Cohen et al. |
| 2012/0322680 | A1 | 12/2012 | Berger et al. |
| 2013/0065946 | A1 | 3/2013 | Croce et al. |
| 2013/0236453 | A1 | 9/2013 | Croce et al. |
| 2014/0187609 | A1 | 7/2014 | Croce |
| 2014/0235697 | A1 | 8/2014 | Weiner et al. |
| 2014/0256562 | A1 | 9/2014 | Umansky et al. |
| 2014/0272998 | A1 | 9/2014 | Ralfkiaer et al. |
| 2014/0329883 | A1 | 11/2014 | Elmen et al. |
| 2015/0299699 | A1 | 10/2015 | Obad et al. |
| 2015/0368647 | A1 | 12/2015 | Croce et al. |
| 2016/0002624 | A1 | 1/2016 | Dibble et al. |
| 2016/0010090 | A1 | 1/2016 | Vagle |
| 2016/0017329 | A1 | 1/2016 | Esau et al. |
| 2016/0244754 | A1 | 8/2016 | Baltimore et al. |
| 2016/0273054 | A1 | 9/2016 | Zhang et al. |
| 2016/0289683 | A1 | 10/2016 | Croce |
| 2016/0319279 | A1 | 11/2016 | Hutvagner et al. |
| 2018/0127750 | A1 | 5/2018 | Rodman et al. |
| 2018/0161357 | A1 | 6/2018 | Jackson et al. |

FOREIGN PATENT DOCUMENTS

| | | |
|---|---|---|
| WO | WO-96/31194 A3 | 10/1996 |
| WO | WO-2003/093449 A2 | 11/2003 |
| WO | WO-2003/093449 A3 | 11/2003 |
| WO | WO-2005/078139 A2 | 8/2005 |
| WO | WO-2005/078139 A3 | 8/2005 |
| WO | WO-2007/081720 A2 | 7/2007 |
| WO | WO-2007/081720 A3 | 7/2007 |
| WO | WO-2007/095387 A2 | 8/2007 |
| WO | WO-2007/095387 A3 | 8/2007 |
| WO | WO-2007/109236 A2 | 9/2007 |
| WO | WO-2007/109236 A3 | 9/2007 |
| WO | WO-2007/112753 A2 | 10/2007 |
| WO | WO-2007/112753 A3 | 10/2007 |
| WO | WO-2007/112754 A2 | 10/2007 |
| WO | WO-2007/112754 A3 | 10/2007 |
| WO | WO-2009/029690 A1 | 3/2009 |
| WO | WO-2009/043353 A2 | 4/2009 |
| WO | WO-2009/043353 A3 | 4/2009 |
| WO | WO-2010/012667 A1 | 2/2010 |
| WO | WO-2013/011378 A1 | 1/2013 |
| WO | WO-2013/055865 A1 | 4/2013 |
| WO | WO-2013/134403 A1 | 9/2013 |
| WO | WO-2016/196978 A1 | 12/2016 |
| WO | WO-2016/197024 A2 | 12/2016 |
| WO | WO-2016/197024 A3 | 12/2016 |
| WO | WO-2018/009855 A1 | 1/2018 |

OTHER PUBLICATIONS

Banerjee, J. et al. (2011). "MicroRNAs in skin and wound healing," *Physiol. Genomics* 43:543-556.

Baumjohann, D. et al. (2013). "MicroRNA-mediated regulation of T helper cell differentiation and plasticity," *Nat. Rev. Immunol.* 13:666-678.

Calin, G.A. et al. (2002), "Frequent deletions and down-regulation of micro-RNA genes miR15 and miR16 at 13q14 in chronic lymphocytic leukemia," *PNAS* 99:15524-15529.

Campbell, J.J. et al. (2010). "Sezary syndrome and mycosis fungoides arise from distinct T-cell subsets: a biologic rationale for their distinct clinical behaviors," *Blood* 116:767-771.

Ceppi, M. et al. (2009). "MicroRNA-155 modulates the interleukin-1 signaling pathway in activated human monocyte-derived dendritic cells," *PNAS* 106:2735-2740.

ClinicalTrials.gov (2015). "Safety, Tolerability and Pharmacokinetic Study of MRG-106 in Patients Wth Cutaneous T Cell Lymphoma (CTCL), MF Subtype," View of NCT02580552 on Oct. 19, 2015, clinical trials identifier: NCT02580552, 4 total pages.

ClinicalTrials.gov (2016). "Safety, Tolerability and Pharmacokinetic Study of MRG-106 in Patients With Cutaneous T Cell Lymphoma (CTCL), MF Subtype," View of NCT02580552 on May 17, 2016, clinical trials identifier: NCT02580552, 4 total pages.

Crouch et al. (1993). *J. Immunological Meth.* 160:81-88.

Dudda, J.C. et al. (2013), "MicroRNA-155 is required for effector CD8+ T cell responses to virus infection and cancer," *Immunity* 38:742-753.

Eis, P.S. et al. (2005). "Accumulation of miR-155 and BIC RNA in human B cell lymphomas," *PNAS* 102:3627-3632.

Elmén, J. et al. (2008). "LNA-mediated microRNA silencing in non-human primates," *Nature* 452:896-899.

Elmén, J. et al. (2008). "Antagonism of microRNA-122 in mice by systemically administered LNA-antimiR leads to up-regulation of a large set of predicted target mRNAs in the liver," *Nuc. Acids Research* 36:1153-1162.

Extended European Search Report dated Nov. 29, 2018, for EP Application No. 16 804 580.5, filed on Jun. 3, 2016, 7 pages.

Extended European Search Report dated Dec. 3, 2018, for EP Application No. 16 804 549.0, flied on Jun. 3, 2016, 9 pages.

Final Office Action dated Mar. 16, 2017, for U.S. Appl. No. 15/173,368, filed Jun. 3, 2016, 16 pages.

Gerloff, D. et al. (2014). "NF-κB/STAT5/miR-155 network targets PU.1 in FLT3-ITD-driven acute myeloid leukemia," *Leukemia* 29:535-547.

Girardi, M. et al. (2004). "The pathogenesis of mycosis fungoides," *N. Engl. J. Med.* 350:1978-1988.

Gracias, D.T. et al. (2013). "The microRNA miR-155 controls CD8+ T cell responses by regulating interferon signaling," *Nat. Immunol.* 14:593-602.

Haasch, D. et al. (2002), "T cell activation induces a noncoding RNA transcript sensitive to inhibition by immunosuppressant drugs and encoded by the proto-oncogene, BIC," *Cell Immunol.* 217:78-86.

Huang, D.W. et al. (2009), "Systematic and integrative analysis of large gene lists using DAVID bioinformatics resources," *Nat. Prtoc.* 4:44-57.

International Search Report dated Dec. 15, 2016, for PCT Application No. PCT/US2016/035865, filed on Jun. 3, 2016, 5 pages.

International Search Report dated Sep. 13, 2016, for PCT application No. PCT/US2016/35794, filed on Jun. 3, 2016, 4 pages.

International Search Report dated Oct. 31, 2017, for PCT application No. PCT/US2017/41180, filed on Jul. 7, 2016, 4 pages.

Iqbal, J. et al. (2015). "Global microRNA expression profiling uncovers molecular markers for classification and prognosis in aggressive B-cell lymphoma," *Blood* 125:1137-1145.

(56) References Cited

OTHER PUBLICATIONS

Jawed, S.I. et al. (2014). "Primary cutaneous T-cell lymphoma (mycosis fungoides and Sézary syndrome): part II. Prognosis, management, and future directions," *J. Am. Acad. Dermatol.* 70:223. e1-17, quiz 240-2.
Jawed, S.I. et al. (2014). "Primary cutaneous T-cell lymphoma (mycosis fungoides and Sézary syndrome): part I. Diagnosis: clinical and histopathologic features and new molecular and biologic markers," *J. Am. Acad. Dermatol.* 70:205.e1-16, quiz 221-2.
Kasashima, K. et al. (2004). "Altered expression profiles of microRNAs during TPA-induced differentiation of HL-60 cells," *Biochem. Biophys. Res. Commun.* 322:403-410.
Kadin, M.E. et al. (2010). "Targeted therapies: Denileukin diftitox—a step towards a 'magic bullet' for CTCL," *Nat. Rev. Clin. Oncol.* 7:430-432.
Kopp, K.L. et al. (2013). "STAT5-mediated expression of oncogenic miR-155 in cutaneous T-cell lymphoma," *Cell Cycle* 12:1939-1947.
Kopp, K.L. et al. (2013). "Expression of miR-155 and miR-126 in situ in cutaneous T-cell lymphoma," *APMIS.* 121:1020-1024.
Koval, E.D, et al. (2013). "Method for widespread microRNA-155 inhibition prolongs survival in ALS-model mice," *Hum. Mol. Genet.* 22:4127-4135.
Krejsgaard, T. et al. (2012). "Regulatory T cells and immunodeficiency in mycosis fungoides and Sézary syndrome," *Leukemia* 26:424-432.
Lagos-Quintana, M. et al. (2002), "Identification of tissue-specific microRNAs from mouse," *Curr. Biol.* 12:735-739.
Landgraf, P. et al. (2007). "A mammalian microRNA expression atlas based on small RNA library sequencing," *Cell* 129:1401-1414.
Lecellier, C.H. et al. (2005). "A cellular microRNA mediates antiviral defense in human cells," *Science* 308(5721):557-560.
Maj, J. et al. (2012). "Altered microRNA expression in mycosis fungoides," *Br. J. Dermatol.* 166:331-336.
Mao, C-P. et al. (2011). "In vivo microRNA-155 expression influences antigen-specific T cell-mediated immune responses generated by DNA vaccination," *Cell & Biosc.* 1:3, 11 total pages.
Masaki, S. et al. (2007). "Expression patterns of microRNAs 155 and 451 during normal human erythropoiesis," *Biochem. Biophys. Res. Comm.* 364:509-514.
McCutcheon's detergents and emulsifiers (1986). North American Edition, pp. 317-324.
Mezei, M. (1985). "Liposomes as a skin drug delivery system," in *Topics in Pharmaceutical Sciences*, Breimer, D. and Speiser, P. eds., Elsevier Science Publishers B.V., New York, NY., pp. 345-358.
Moyal, L. et al. (2013). "miR-155 is involved in tumor progression of mycosis fungoides," *Exp. Dermatol.* 22:431-433.
Naguibneva et al. (2006). *Nature Cell Biol.* 8:278-284.
Niemiec, S.M. et al. (1995). "Influence of nonionic liposomal composition on topical delivery of peptide drugs into pilosebaceous units: an in vivo study using the hamster ear model," *Pharm. Res.* 12:1184-1188.
Non-Final Office Action dated Dec. 5, 2016, for U.S. Appl. No. 15/173,368, filed Jun. 3, 2016, 13 pages.
Non-Final Office Action dated Mar. 5, 2018, for U.S. Appl. No. 15/714,671, filed Sep. 25, 2017, 11 pages.
Non-Final Office Action dated Jul. 12, 2018, for U.S. Appl. No. 15/677,818, filed Aug. 15, 2017, 14 pages.
Non-Final Office Action dated Jul. 25, 2018, for U.S. Appl. No. 15/579,718, filed Dec. 5, 2017, 14 pages.
Notice of Allowance dated Jul. 21, 2017, for U.S. Appl. No. 15/173,368, filed Jun. 3, 2016, 8 pages.
Notice of Allowance dated May 2, 2018, for U.S. Appl. No. 15/714,671, filed Sep. 25, 2017, 9 pages.
Obad, S. et al. (2011). "Silencing of microRNA families by seed-targeting tiny LNAs," *Nature Genetics* 43:371-378.
O'Connell, R.M. et al. (2010). "MicroRNA-155 promotes autoimmune inflammation by enhancing inflammatory T cell development," *Immunity* 33:607-619.
O'Connell, R.M. et al. (2007). "MicroRNA-155 is induced during the macrophage inflammatory response," *PNAS* 104:1604-1609.
Olsen, E.A. et al. (2011). "Clinical end points and response criteria in mycosis fungoides and Sézary syndrome: a consensus statement of the International Society for Cutaneous Lymphomas, the United States Cutaneous Lymphoma Consortium, and the Cutaneous Lymphoma Task Force of the European Organisation for Research and Treatment of Cancer," *J. Clin. Oncol.* 29:2598-2607.
Pitzer, C. et al. (2008). "Granulocyte-colony stimulating factor improves outcome in a mouse model of amyotrophic lateral sclerosis," *Brain* 131(Pt. 12):3335-3347.
Pollari, E. et al. (2011). "Granulocyte colony stimulating factor attenuates inflammation in a mouse model of amyotrophic lateral sclerosis," *Neuroinflammation* 8:74, 14 total pages.
Prince, H.M. et al. (2009). "How I treat mycosis fungoides and Sézary syndrome," *Blood* 114:4337-4353.
Qi, P. et al. (2006). "Virus-encoded microRNAs: future therapeutic targets?" *Cellular & Molec, Immunol.* 3:411-419.
Ralfkiaer, U. et al. (2011). "Diagnostic microRNA profiling in cutaneous T-cell lymphoma (CTCL)," *Blood* 118:5891-5900.
Restriction Requirement dated Sep. 15, 2016, for U.S. Appl. No. 15/173,366, filed Jun. 3, 2016, 8 pages.
Rodriguez, A. et al. (2007). "Requirement of bic/microRNA-155 for normal immune function," *Science* 316:608-611.
Sagarin (1972). Cosmetics, Science and Technology, $2^{nd}$ edition, Wiley-Interscience, vol. 1, pp. 32-43 and 72-73.
Seto et al. (2015) ASH abstract: Preclinical Results Supporting Therapeutic Development of MRG-106, an Oligonucleotide Inhibitor of miR-155, in CTCL.
Taganov, K.D. et al. (2006). "NF-κβ-dependent induction of microRNA miR-146, an inhibitor targeted to signaling proteins of innate immune responses," *PNAS* 103:12481-12486.
Tam, W. et al. (2002). "Avian bic, a gene isolated from a common retroviral site in avian leukosis virus-induced lymphomas that encodes a noncoding RNA, cooperates with c-myc in lymphomagenesis and erythroleukemogenesis," *J. Virol .* 76:4275-4286.
Takahashi, N. et al. (2012). "Profiling of immune-related microRNA expression in human cord blood and adult peripheral blood cells upon proinflammatory stimulation," *Eur. J. Haematol.* 68:31-38.
Thai, T-H. et al. (2007). "Regulation of the germinal center response by micro-RNA-155," *Science* 316:604-608.
van den Berg, A. et al. (2003). "High expression of B-cell receptor inducible gene BIC in all subtypes of Hodgkin lymphoma," *Genes Chromo. Cancer* 37:20-28.
van Doorn, R. et al. (2009). "Oncogenomic analysis of mycosis fungoides reveals major differences with Sezary syndrome," *Blood* 113:127-136.
van Kester, M.S. et al. (2011). "miRNA expression profiling of mycosis fungoides," *Molec. Oncol.* 5:273-280.
van Meer, L. et al. (2016). "Injection site reactions after subcutaneous oligonucleotide therapy," *Br. J. Clin. Pharmacol.* 82:340-351.
Vigorito, E. et al. (2007). "microRNA-155 regulates the generation of immunoglobulin class-switched plasma cells," *Immunity* 27:847-859.
Wang, G. et al. (1999). "Conformationally locked nucleosides. Synthesis and hybridization properties of oligodeoxynucleotides containing 2',4'-C-bridged 2'-deoxynucleosides," *Bioorg. Med. Chem. Letters* 9:1147-1150.
Weber, M.J. (2005). "New human and mouse microRNA genes found by homology search," *FEBS J.* 272:59-73.
Wenninger and McEwen (1997). International Cosmetic Ingredient Dictionary and Handbook, The Cosmetic, Toiletry, and Fragrance Association, Washington, DC., $7^{th}$ edition, vol. 2, pp. 1626, 1654-1655, 1656-1661, 1673-1686, and 1693-1697.
Worm, J. et al. (2009), "Silencing of microRNA-155 in mice during acute inflammatory response leads to derepression of c/ebp Beta and down-regulation of G-CSF," *Nuc. Acids Res.* 37(17):5784-5792.
Worm, J. et al. (2008). "Efficient LNA-mediated antagonism of microRNA-155 in vitro and in vivo," RNAi, microRNA and noncoding RNA, Keystone Symposium, Mar. 25-30, 2008. Abstract No. 474, 2 pages.
Written Opinion of the International Searching Authority dated Dec. 15, 2016, for PCT Application No. PCT/US2016/035865, filed on Jun. 3, 2016, 8 pages.

(56) References Cited

OTHER PUBLICATIONS

Written Opinion of the International Searching Authority dated Sep. 13, 2016, for PCT application No. PCT/US2016/35794, filed on Jun. 3, 2016, 6 pages.
Written Opinion of the International Searching Authority dated Oct. 31, 2017, for PCT application No. PCT/US2017/41180, filed on Jul. 7, 2016, 6 pages.
Zhang, L. et al. (2006). "microRNAs exhibit high frequency genomic alterations in human cancer," *PNAS* 103:9136-9141.
Zhang, Y. et al. (2012). "LNA-mediated anti-miR-155 silencing in low-grade B-cell lymphomas," *Blood* 120:1678-1686.
U.S. Appl. No. 16/315,344, filed Jul. 7, 2017, by Jackson et al.
Babar, I.A. et al. (2012). "Nanoparticle-based therapy in an in vivo microRNA-155 (miR-155)- dependent mouse model of lymphoma,"PNAS 109:E1695-E1704.

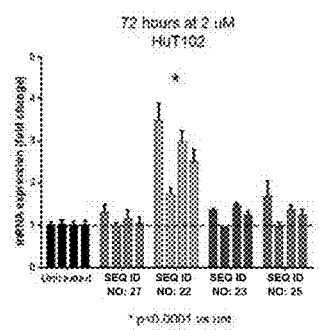 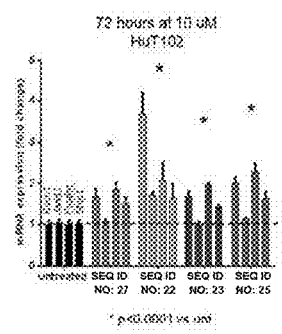 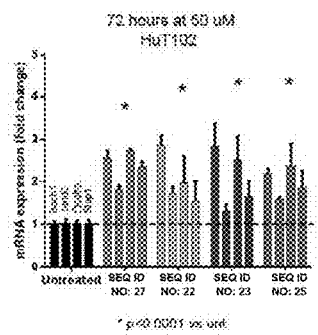
FIG. 3A            FIG. 3B            FIG. 3C
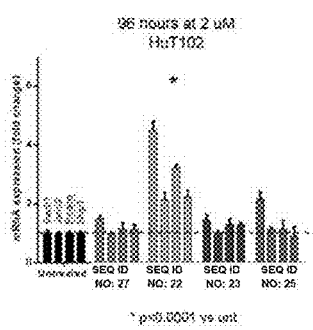 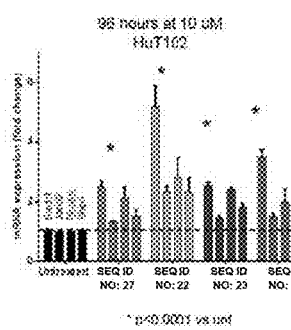 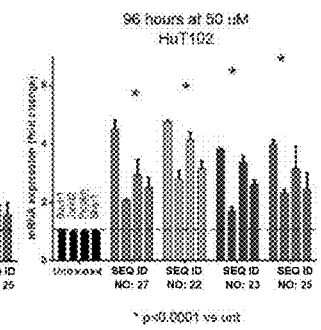
FIG. 3D            FIG. 3E            FIG. 3F

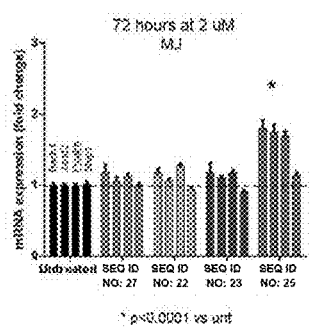 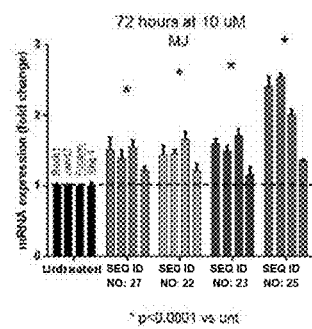 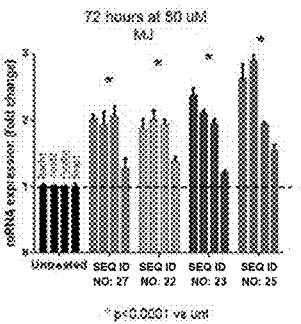
FIG. 4A　　　　　　FIG. 4B　　　　　　FIG. 4C
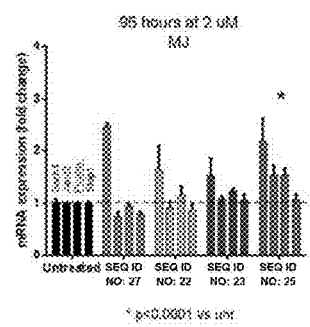 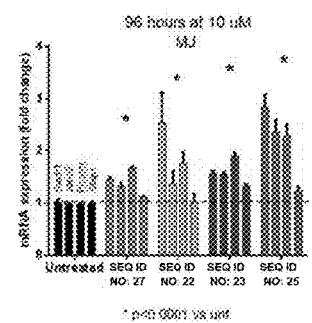 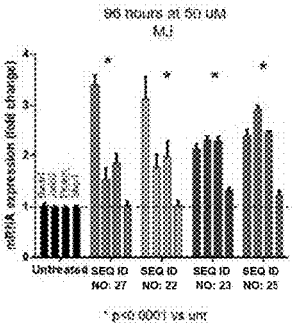
FIG. 4D　　　　　　FIG. 4E　　　　　　FIG. 4F

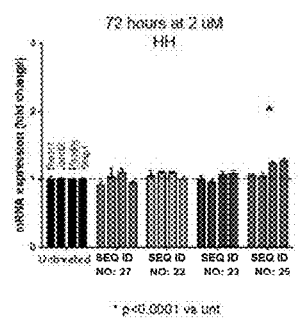 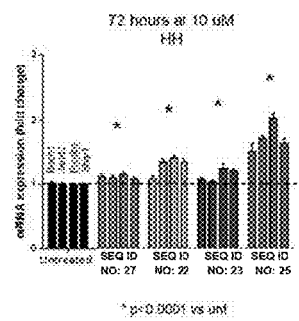 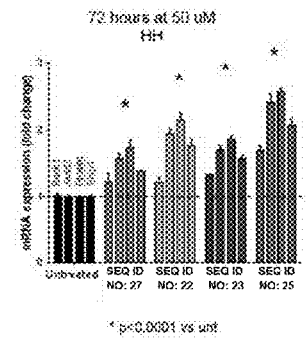
FIG. 5A　　　　　　FIG. 5B　　　　　　FIG. 5C
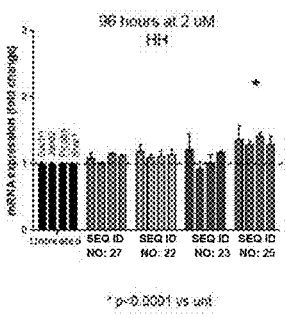 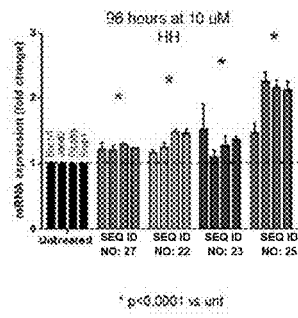 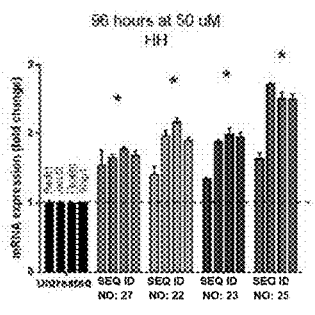
FIG. 5D　　　　　　FIG. 5E　　　　　　FIG. 5F

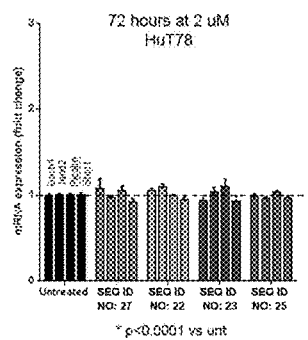
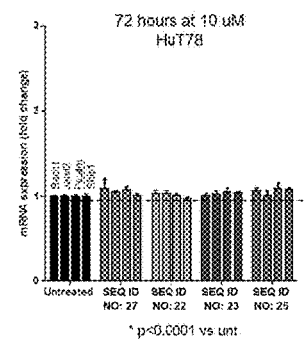
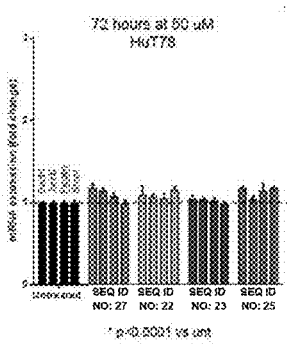
FIG. 7A                  FIG. 7B                  FIG. 7C
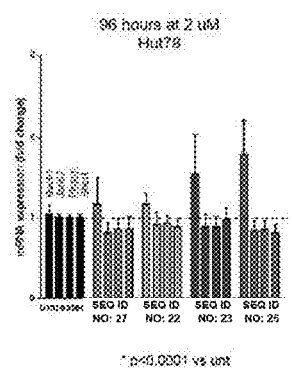
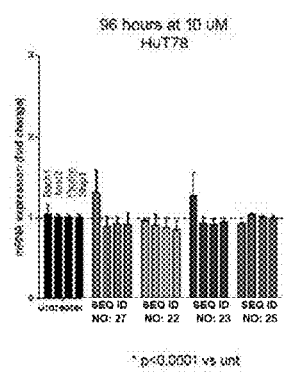
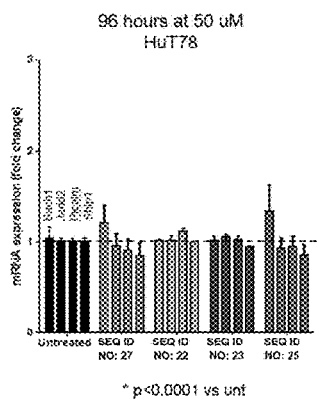
FIG. 7D                  FIG. 7E                  FIG. 7F

SEQUENCE LISTING

```
<160> NUMBER OF SEQ ID NOS: 122

<210> SEQ ID NO 1
<211> LENGTH: 23
<212> TYPE: RNA
<213> ORGANISM: Homo sapiens

<400> SEQUENCE: 1
uuaaugcuaa ucgugauagg ggu                                           23

<210> SEQ ID NO 2
<211> LENGTH: 22
<212> TYPE: RNA
<213> ORGANISM: Homo sapiens

<400> SEQUENCE: 2
cuccuacaua uuagcauuaa ca                                            22
```

<210> SEQ ID NO 3
<211> LENGTH: 16
<212> TYPE: DNA
<213> ORGANISM: Artificial Sequence
<220> FEATURE:
<223> OTHER INFORMATION: miR-155 10101
<220> FEATURE:
<221> NAME/KEY: misc_feature
<222> LOCATION: (1)..(16)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (5)..(5)
<223> OTHER INFORMATION: May be locked nucleic acid cytidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(11)
<223> OTHER INFORMATION: May be locked nucleic acid guanosine
<220> FEATURE:
<221> NAME/KEY: modified_base
<222> LOCATION: (13)..(13)
<223> OTHER INFORMATION: May be locked nucleic acid adenosine
<220> FEATURE:
<221> NAME/KEY: modified_base
<222> LOCATION: (15)..(15)
<223> OTHER INFORMATION: May be locked nucleic acid thymidine
<220> FEATURE:
<221> NAME/KEY: modified_base
<222> LOCATION: (16)..(16)
<223> OTHER INFORMATION: May be locked nucleic acid adenosine

<400> SEQUENCE: 3
atcacgatta gcatta                                                     16

<210> SEQ ID NO 4
<211> LENGTH: 16
<212> TYPE: DNA
<213> ORGANISM: Artificial Sequence
<220> FEATURE:
<223> OTHER INFORMATION: miR-155 11293
<220> FEATURE:
<221> NAME/KEY: misc_feature
<222> LOCATION: (1)..(16)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (5)..(5)
<223> OTHER INFORMATION: May be locked nucleic acid cytidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid thymidine -continued

```
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(11)
<223> OTHER INFORMATION: May be locked nucleic acid guanosine
<220> FEATURE:
<221> NAME/KEY: modified_base
<222> LOCATION: (13)..(13)
<223> OTHER INFORMATION: May be locked nucleic acid adenosine
<220> FEATURE:
<221> NAME/KEY: modified_base
<222> LOCATION: (15)..(15)
<223> OTHER INFORMATION: May be locked nucleic acid thymidine
<220> FEATURE:
<221> NAME/KEY: modified_base
<222> LOCATION: (16)..(16)
<223> OTHER INFORMATION: May be locked nucleic acid adenosine

<400> SEQUENCE: 4
atcacgatta gcatta                                                 16

<210> SEQ ID NO 5
<211> LENGTH: 16
<212> TYPE: DNA
<213> ORGANISM: Artificial Sequence
<220> FEATURE:
<223> OTHER INFORMATION: miR-155 11294
<220> FEATURE:
<221> NAME/KEY: misc_feature
<222> LOCATION: (1)..(16)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(11)
<223> OTHER INFORMATION: May be locked nucleic acid guanosine
<220> FEATURE:
<221> NAME/KEY: modified_base
<222> LOCATION: (13)..(13)
<223> OTHER INFORMATION: May be locked nucleic acid adenosine
<220> FEATURE:
<221> NAME/KEY: modified_base
<222> LOCATION: (15)..(15)
<223> OTHER INFORMATION: May be locked nucleic acid thymidine
<220> FEATURE:
<221> NAME/KEY: modified_base
<222> LOCATION: (16)..(16)
<223> OTHER INFORMATION: May be locked nucleic acid adenosine

<400> SEQUENCE: 5
atcacgatta gcatta                                                 16

<210> SEQ ID NO 6
```

```
<211> LENGTH: 16
<212> TYPE: DNA
<213> ORGANISM: Artificial Sequence
<220> FEATURE:
<223> OTHER INFORMATION: miR-155 11295
<220> FEATURE:
<221> NAME/KEY: misc_feature
<222> LOCATION: (1)..(16)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (7)..(7)
<223> OTHER INFORMATION: May be locked nucleic acid adenosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(11)
<223> OTHER INFORMATION: May be locked nucleic acid guanosine
<220> FEATURE:
<221> NAME/KEY: modified_base
<222> LOCATION: (12)..(12)
<223> OTHER INFORMATION: May be locked nucleic acid cytidine
<220> FEATURE:
<221> NAME/KEY: modified_base
<222> LOCATION: (14)..(14)
<223> OTHER INFORMATION: May be locked nucleic acid thymidine
<220> FEATURE:
<221> NAME/KEY: modified_base
<222> LOCATION: (16)..(16)
<223> OTHER INFORMATION: May be locked nucleic acid adenosine

<400> SEQUENCE: 6
atcacgatta gcatta                                                  16

<210> SEQ ID NO 7
<211> LENGTH: 16
<212> TYPE: DNA
<213> ORGANISM: Artificial Sequence
<220> FEATURE:
<223> OTHER INFORMATION: miR-155 11296
<220> FEATURE:
<221> NAME/KEY: misc_feature
<222> LOCATION: (1)..(16)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (5)..(5)
<223> OTHER INFORMATION: May be locked nucleic acid cytidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid thymidine
<220> FEATURE:
<221> NAME/KEY: modified_base
```

```
<222> LOCATION: (10)..(10)
<223> OTHER INFORMATION: May be locked nucleic acid adenosine
<220> FEATURE:
<221> NAME/KEY: modified_base
<222> LOCATION: (11)..(11)
<223> OTHER INFORMATION: May be locked nucleic acid guanosine
<220> FEATURE:
<221> NAME/KEY: modified_base
<222> LOCATION: (13)..(13)
<223> OTHER INFORMATION: May be locked nucleic acid adenosine
<220> FEATURE:
<221> NAME/KEY: modified_base
<222> LOCATION: (14)..(14)
<223> OTHER INFORMATION: May be locked nucleic acid thymidine
<220> FEATURE:
<221> NAME/KEY: modified_base
<222> LOCATION: (16)..(16)
<223> OTHER INFORMATION: May be locked nucleic acid adenosine

<400> SEQUENCE: 7
atcacgatta gcatta                                                   16

<210> SEQ ID NO 8
<211> LENGTH: 16
<212> TYPE: DNA
<213> ORGANISM: Artificial Sequence
<220> FEATURE:
<223> OTHER INFORMATION: miR-155 16 6
<220> FEATURE:
<221> NAME/KEY: misc_feature
<222> LOCATION: (1)..(16)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid thymidine
<220> FEATURE:
<221> NAME/KEY: modified_base
<222> LOCATION: (5)..(5)
<223> OTHER INFORMATION: May be locked nucleic acid cytidine
<220> FEATURE:
<221> NAME/KEY: modified_base
<222> LOCATION: (9)..(9)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (12)..(12)
<223> OTHER INFORMATION: May be locked nucleic acid cytidine
<220> FEATURE:
<221> NAME/KEY: modified_base
<222> LOCATION: (13)..(13)
<223> OTHER INFORMATION: May be locked nucleic acid adenosine
<220> FEATURE:
<221> NAME/KEY: modified_base
<222> LOCATION: (15)..(15)
<223> OTHER INFORMATION: May be locked nucleic acid thymidine
<220> FEATURE:
<221> NAME/KEY: modified_base
<222> LOCATION: (16)..(16)
<223> OTHER INFORMATION: May be locked nucleic acid adenosine

<400> SEQUENCE: 8
atcacgatta gcatta                                                   16

<210> SEQ ID NO 9
<211> LENGTH: 16
<212> TYPE: DNA
```

```
<213> ORGANISM: Artificial Sequence
<220> FEATURE:
<223> OTHER INFORMATION: miR-155 16 7
<220> FEATURE:
<221> NAME/KEY: misc_feature
<222> LOCATION: (1)..(16)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (5)..(5)
<223> OTHER INFORMATION: May be locked nucleic acid cytidine
<220> FEATURE:
<221> NAME/KEY: modified_base
<222> LOCATION: (7)..(7)
<223> OTHER INFORMATION: May be locked nucleic acid adenosine
<220> FEATURE:
<221> NAME/KEY: modified_base
<222> LOCATION: (9)..(9)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (12)..(12)
<223> OTHER INFORMATION: May be locked nucleic acid cytidine
<220> FEATURE:
<221> NAME/KEY: modified_base
<222> LOCATION: (13)..(13)
<223> OTHER INFORMATION: May be locked nucleic acid adenosine
<220> FEATURE:
<221> NAME/KEY: modified_base
<222> LOCATION: (15)..(15)
<223> OTHER INFORMATION: May be locked nucleic acid thymidine
<220> FEATURE:
<221> NAME/KEY: modified_base
<222> LOCATION: (16)..(16)
<223> OTHER INFORMATION: May be locked nucleic acid adenosine

<400> SEQUENCE: 9
atcacgatta gcatta                                                    16

<210> SEQ ID NO 10
<211> LENGTH: 16
<212> TYPE: DNA
<213> ORGANISM: Artificial Sequence
<220> FEATURE:
<223> OTHER INFORMATION: miR-155 16 8
<220> FEATURE:
<221> NAME/KEY: misc_feature
<222> LOCATION: (1)..(16)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (4)..(4)
<223> OTHER INFORMATION: May be locked nucleic acid adenosine
<220> FEATURE:
<221> NAME/KEY: modified_base
<222> LOCATION: (7)..(7)
<223> OTHER INFORMATION: May be locked nucleic acid adenosine
<220> FEATURE:
<221> NAME/KEY: modified_base
<222> LOCATION: (8)..(8)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid adenosine
```

```
<220> FEATURE:
<221> NAME/KEY: modified_base
<222> LOCATION: (11)..(11)
<223> OTHER INFORMATION: May be locked nucleic acid guanosine
<220> FEATURE:
<221> NAME/KEY: modified_base
<222> LOCATION: (13)..(13)
<223> OTHER INFORMATION: May be locked nucleic acid adenosine
<220> FEATURE:
<221> NAME/KEY: modified_base
<222> LOCATION: (15)..(15)
<223> OTHER INFORMATION: May be locked nucleic acid thymidine
<220> FEATURE:
<221> NAME/KEY: modified_base
<222> LOCATION: (16)..(16)
<223> OTHER INFORMATION: May be locked nucleic acid adenosine

<400> SEQUENCE: 10
atcacgatta gcatta                                                    16

<210> SEQ ID NO 11
<211> LENGTH: 16
<212> TYPE: DNA
<213> ORGANISM: Artificial Sequence
<220> FEATURE:
<223> OTHER INFORMATION: miR-155 16 9
<220> FEATURE:
<221> NAME/KEY: misc_feature
<222> LOCATION: (1)..(16)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(9)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid cytidine
<220> FEATURE:
<221> NAME/KEY: modified_base
<222> LOCATION: (13)..(13)
<223> OTHER INFORMATION: May be locked nucleic acid adenosine
<220> FEATURE:
<221> NAME/KEY: modified_base
<222> LOCATION: (15)..(15)
<223> OTHER INFORMATION: May be locked nucleic acid thymidine
<220> FEATURE:
<221> NAME/KEY: modified_base
<222> LOCATION: (16)..(16)
<223> OTHER INFORMATION: May be locked nucleic acid adenosine

<400> SEQUENCE: 11
atcacgatta gcatta                                                    16

<210> SEQ ID NO 12
<211> LENGTH: 16
<212> TYPE: DNA
<213> ORGANISM: Artificial Sequence
<220> FEATURE:
<223> OTHER INFORMATION: miR-155 16 10
<220> FEATURE:
<221> NAME/KEY: misc_feature
<222> LOCATION: (1)..(16)
```

```
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid thymidine
<220> FEATURE:
<221> NAME/KEY: modified_base
<222> LOCATION: (4)..(4)
<223> OTHER INFORMATION: May be locked nucleic acid adenosine
<220> FEATURE:
<221> NAME/KEY: modified_base
<222> LOCATION: (5)..(5)
<223> OTHER INFORMATION: May be locked nucleic acid cytidine
<220> FEATURE:
<221> NAME/KEY: modified_base
<222> LOCATION: (9)..(9)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (12)..(12)
<223> OTHER INFORMATION: May be locked nucleic acid cytidine
<220> FEATURE:
<221> NAME/KEY: modified_base
<222> LOCATION: (13)..(13)
<223> OTHER INFORMATION: May be locked nucleic acid adenosine
<220> FEATURE:
<221> NAME/KEY: modified_base
<222> LOCATION: (16)..(16)
<223> OTHER INFORMATION: May be locked nucleic acid adenosine

<400> SEQUENCE: 12
atcacgatta gcatta                                                    16

<210> SEQ ID NO 13
<211> LENGTH: 16
<212> TYPE: DNA
<213> ORGANISM: Artificial Sequence
<220> FEATURE:
<223> OTHER INFORMATION: miR-155 16 11
<220> FEATURE:
<221> NAME/KEY: misc_feature
<222> LOCATION: (1)..(16)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (7)..(7)
<223> OTHER INFORMATION: May be locked nucleic acid adenosine
<220> FEATURE:
<221> NAME/KEY: modified_base
<222> LOCATION: (9)..(9)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (12)..(12)
<223> OTHER INFORMATION: May be locked nucleic acid cytidine
<220> FEATURE:
<221> NAME/KEY: modified_base
```

```
<222> LOCATION: (13)..(13)
<223> OTHER INFORMATION: May be locked nucleic acid adenosine
<220> FEATURE:
<221> NAME/KEY: modified_base
<222> LOCATION: (15)..(15)
<223> OTHER INFORMATION: May be locked nucleic acid thymidine
<220> FEATURE:
<221> NAME/KEY: modified_base
<222> LOCATION: (16)..(16)
<223> OTHER INFORMATION: May be locked nucleic acid adenosine

<400> SEQUENCE: 13
atcacgatta gcatta                                                     16

<210> SEQ ID NO 14
<211> LENGTH: 16
<212> TYPE: DNA
<213> ORGANISM: Artificial Sequence
<220> FEATURE:
<223> OTHER INFORMATION: miR-155 16 12
<220> FEATURE:
<221> NAME/KEY: misc_feature
<222> LOCATION: (1)..(16)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (5)..(5)
<223> OTHER INFORMATION: May be locked nucleic acid cytidine
<220> FEATURE:
<221> NAME/KEY: modified_base
<222> LOCATION: (7)..(7)
<223> OTHER INFORMATION: May be locked nucleic acid adenosine
<220> FEATURE:
<221> NAME/KEY: modified_base
<222> LOCATION: (9)..(9)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid guanosine
<220> FEATURE:
<221> NAME/KEY: modified_base
<222> LOCATION: (13)..(13)
<223> OTHER INFORMATION: May be locked nucleic acid adenosine
<220> FEATURE:
<221> NAME/KEY: modified_base
<222> LOCATION: (15)..(15)
<223> OTHER INFORMATION: May be locked nucleic acid thymidine
<220> FEATURE:
<221> NAME/KEY: modified_base
<222> LOCATION: (16)..(16)
<223> OTHER INFORMATION: May be locked nucleic acid adenosine

<400> SEQUENCE: 14
atcacgatta gcatta                                                     16

<210> SEQ ID NO 15
<211> LENGTH: 15
<212> TYPE: DNA
<213> ORGANISM: Artificial Sequence
<220> FEATURE:
<223> OTHER INFORMATION: miR-155 15 1
<220> FEATURE:
<221> NAME/KEY: misc_feature
<222> LOCATION: (1)..(15)
<223> OTHER INFORMATION: May be joined through phosphorothioate bonds
<220> FEATURE:
```

```
<221> NAME/KEY: modified_base
<222> LOCATION: (1)..(1)
<223> OTHER INFORMATION: May be locked nucleic acid thymidine
<220> FEATURE:
<221> NAME/KEY: modified_base
<222> LOCATION: (4)..(4)
<223> OTHER INFORMATION: May be locked nucleic acid cytidine
<220> FEATURE:
<221> NAME/KEY: modified_base
<222> LOCATION: (7)..(7)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid guanosine
<220> FEATURE:
<221> NAME/KEY: modified_base
<222> LOCATION: (12)..(12)
<223> OTHER INFORMATION: May be locked nucleic acid adenosine
<220> FEATURE:
<221> NAME/KEY: modified_base
<222> LOCATION: (13)..(13)
<223> OTHER INFORMATION: May be locked nucleic acid thymidine
<220> FEATURE:
<221> NAME/KEY: modified_base
<222> LOCATION: (15)..(15)
<223> OTHER INFORMATION: May be locked nucleic acid adenosine

<400> SEQUENCE: 15
tcacgattag catta                                                      15

<210> SEQ ID NO 16
<211> LENGTH: 15
<212> TYPE: DNA
<213> ORGANISM: Artificial Sequence
<220> FEATURE:
<223> OTHER INFORMATION: miR-155 15 2
<220> FEATURE:
<221> NAME/KEY: misc_feature
<222> LOCATION: (1)..(15)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid thymidine
<220> FEATURE:
<221> NAME/KEY: modified_base
<222> LOCATION: (3)..(3)
<223> OTHER INFORMATION: May be locked nucleic acid adenosine
<220> FEATURE:
<221> NAME/KEY: modified_base
<222> LOCATION: (6)..(6)
<223> OTHER INFORMATION: May be locked nucleic acid adenosine
<220> FEATURE:
<221> NAME/KEY: modified_base
<222> LOCATION: (7)..(7)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid guanosine
<220> FEATURE:
<221> NAME/KEY: modified_base
<222> LOCATION: (12)..(12)
<223> OTHER INFORMATION: May be locked nucleic acid adenosine
<220> FEATURE:
<221> NAME/KEY: modified_base
<222> LOCATION: (14)..(14)
<223> OTHER INFORMATION: May be locked nucleic acid thymidine
<220> FEATURE:
<221> NAME/KEY: modified_base
<222> LOCATION: (15)..(15)
<223> OTHER INFORMATION: May be locked nucleic acid adenosine

<400> SEQUENCE: 16
tcacgattag catta                                                      15
```

```
<210> SEQ ID NO 17
<211> LENGTH: 15
<212> TYPE: DNA
<213> ORGANISM: Artificial Sequence
<220> FEATURE:
<223> OTHER INFORMATION: miR-155 15 3
<220> FEATURE:
<221> NAME/KEY: misc_feature
<222> LOCATION: (1)..(15)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid thymidine
<220> FEATURE:
<221> NAME/KEY: modified_base
<222> LOCATION: (5)..(5)
<223> OTHER INFORMATION: May be locked nucleic acid guanosine
<220> FEATURE:
<221> NAME/KEY: modified_base
<222> LOCATION: (6)..(6)
<223> OTHER INFORMATION: May be locked nucleic acid adenosine
<220> FEATURE:
<221> NAME/KEY: modified_base
<222> LOCATION: (7)..(7)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid guanosine
<220> FEATURE:
<221> NAME/KEY: modified_base
<222> LOCATION: (12)..(12)
<223> OTHER INFORMATION: May be locked nucleic acid adenosine
<220> FEATURE:
<221> NAME/KEY: modified_base
<222> LOCATION: (14)..(14)
<223> OTHER INFORMATION: May be locked nucleic acid thymidine
<220> FEATURE:
<221> NAME/KEY: modified_base
<222> LOCATION: (15)..(15)
<223> OTHER INFORMATION: May be locked nucleic acid adenosine

<400> SEQUENCE: 17
tcacgattag catta                                                15

<210> SEQ ID NO 18
<211> LENGTH: 15
<212> TYPE: DNA
<213> ORGANISM: Artificial Sequence
<220> FEATURE:
<223> OTHER INFORMATION: miR-155 15 10823
<220> FEATURE:
<221> NAME/KEY: misc_feature
<222> LOCATION: (1)..(15)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid thymidine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid adenosine
<220> FEATURE:
<221> NAME/KEY: modified_base
<222> LOCATION: (5)..(5)
<223> OTHER INFORMATION: May be locked nucleic acid guanosine
<220> FEATURE:
<221> NAME/KEY: modified_base
<222> LOCATION: (8)..(8)
```

<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (11)..(11)
<223> OTHER INFORMATION: May be locked nucleic acid cytidine
<220> FEATURE:
<221> NAME/KEY: modified_base
<222> LOCATION: (14)..(14)
<223> OTHER INFORMATION: May be locked nucleic acid thymidine
<220> FEATURE:
<221> NAME/KEY: modified_base
<222> LOCATION: (15)..(15)
<223> OTHER INFORMATION: May be locked nucleic acid adenosine

<400> SEQUENCE: 18
tcacgattag catta                                                    15

<210> SEQ ID NO 19
<211> LENGTH: 15
<212> TYPE: DNA
<213> ORGANISM: Artificial Sequence
<220> FEATURE:
<223> OTHER INFORMATION: miR-155 15 10824
<220> FEATURE:
<221> NAME/KEY: misc_feature
<222> LOCATION: (1)..(15)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid thymidine
<220> FEATURE:
<221> NAME/KEY: modified_base
<222> LOCATION: (4)..(4)
<223> OTHER INFORMATION: May be locked nucleic acid cytidine
<220> FEATURE:
<221> NAME/KEY: modified_base
<222> LOCATION: (8)..(8)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(10)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid cytidine
<220> FEATURE:
<221> NAME/KEY: modified_base
<222> LOCATION: (12)..(12)
<223> OTHER INFORMATION: May be locked nucleic acid adenosine
<220> FEATURE:
<221> NAME/KEY: modified_base
<222> LOCATION: (13)..(14)
<223> OTHER INFORMATION: May be locked nucleic acid thymidine
<220> FEATURE:
<221> NAME/KEY: modified_base
<222> LOCATION: (15)..(15)
<223> OTHER INFORMATION: May be locked nucleic acid adenosine

<400> SEQUENCE: 19
tcacgattag catta                                                    15

<210> SEQ ID NO 20
<211> LENGTH: 15
<212> TYPE: DNA
<213> ORGANISM: Artificial Sequence

```
<220> FEATURE:
<223> OTHER INFORMATION: miR-155 15 4
<220> FEATURE:
<221> NAME/KEY: misc_feature
<222> LOCATION: (1)..(15)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid thymidine
<220> FEATURE:
<221> NAME/KEY: modified_base
<222> LOCATION: (3)..(3)
<223> OTHER INFORMATION: May be locked nucleic acid adenosine
<220> FEATURE:
<221> NAME/KEY: modified_base
<222> LOCATION: (5)..(5)
<223> OTHER INFORMATION: May be locked nucleic acid guanosine
<220> FEATURE:
<221> NAME/KEY: modified_base
<222> LOCATION: (6)..(6)
<223> OTHER INFORMATION: May be locked nucleic acid adenosine
<220> FEATURE:
<221> NAME/KEY: modified_base
<222> LOCATION: (7)..(7)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid cytidine
<220> FEATURE:
<221> NAME/KEY: modified_base
<222> LOCATION: (12)..(12)
<223> OTHER INFORMATION: May be locked nucleic acid adenosine
<220> FEATURE:
<221> NAME/KEY: modified_base
<222> LOCATION: (14)..(14)
<223> OTHER INFORMATION: May be locked nucleic acid thymidine
<220> FEATURE:
<221> NAME/KEY: modified_base
<222> LOCATION: (15)..(15)
<223> OTHER INFORMATION: May be locked nucleic acid adenosine

<400> SEQUENCE: 20
tcacgattag catta                                                    15

<210> SEQ ID NO 21
<211> LENGTH: 11
<212> TYPE: DNA
<213> ORGANISM: Artificial Sequence
<220> FEATURE:
<223> OTHER INFORMATION: miR-155 11 1
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (2)..(2)
<223> OTHER INFORMATION: May be locked nucleic acid adenosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (5)..(5)
<223> OTHER INFORMATION: May be locked nucleic acid adenosine
<220> FEATURE:
```

<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(9)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 21
gattagcatt a                                                              11

<210> SEQ ID NO 22
<211> LENGTH: 12
<212> TYPE: DNA
<213> ORGANISM: Artificial Sequence
<220> FEATURE:
<223> OTHER INFORMATION: miR-155 12 1
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid adenosine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid adenosine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 22
cgattagcat ta                                                             12

<210> SEQ ID NO 23
<211> LENGTH: 12
<212> TYPE: DNA
<213> ORGANISM: Artificial Sequence
<220> FEATURE:
<223> OTHER INFORMATION: miR-155 12 2
<220> FEATURE:
<221> NAME/KEY: misc_feature
<222> LOCATION: (1)..(12)
<223> OTHER INFORMATION: May be joined through phosphorothioate bonds

```
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid adenosine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 23
cgattagcat ta                                                          12

<210> SEQ ID NO 24
<211> LENGTH: 14
<212> TYPE: DNA
<213> ORGANISM: Artificial Sequence
<220> FEATURE:
<223> OTHER INFORMATION: miR-155 14 1
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (2)..(2)
<223> OTHER INFORMATION: May be locked nucleic acid adenosine
<220> FEATURE:
<221> NAME/KEY: modified_base
<222> LOCATION: (4)..(4)
<223> OTHER INFORMATION: May be locked nucleic acid guanosine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 24
```
cacgattagc atta                                                         14

<210> SEQ ID NO 25
<211> LENGTH: 14
<212> TYPE: DNA
<213> ORGANISM: Artificial Sequence
<220> FEATURE:
<223> OTHER INFORMATION: miR-155 14 2
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 25
cacgattagc atta                                                         14

<210> SEQ ID NO 26
<211> LENGTH: 15
<212> TYPE: DNA
<213> ORGANISM: Artificial Sequence
<220> FEATURE:
<223> OTHER INFORMATION: 11622 Me C-DNA
<220> FEATURE:
<221> NAME/KEY: misc_feature
<222> LOCATION: (1)..(15)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid thymidine
<220> FEATURE:
<221> NAME/KEY: modified_base
<222> LOCATION: (3)..(3)
<223> OTHER INFORMATION: May be locked nucleic acid adenosine
<220> FEATURE:
<221> NAME/KEY: modified_base
<222> LOCATION: (4)..(4)
<223> OTHER INFORMATION: May be 5-Methylcytosine
<220> FEATURE:
<221> NAME/KEY: modified_base
<222> LOCATION: (5)..(5)
<223> OTHER INFORMATION: May be locked nucleic acid guanosine
<220> FEATURE:
<221> NAME/KEY: modified_base
<222> LOCATION: (6)..(6)
<223> OTHER INFORMATION: May be locked nucleic acid adenosine
<220> FEATURE:
<221> NAME/KEY: modified_base

```
<222> LOCATION: (7)..(7)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid cytidine
<220> FEATURE:
<221> NAME/KEY: modified_base
<222> LOCATION: (12)..(12)
<223> OTHER INFORMATION: May be locked nucleic acid adenosine
<220> FEATURE:
<221> NAME/KEY: modified_base
<222> LOCATION: (14)..(14)
<223> OTHER INFORMATION: May be locked nucleic acid thymidine
<220> FEATURE:
<221> NAME/KEY: modified_base
<222> LOCATION: (15)..(15)
<223> OTHER INFORMATION: May be locked nucleic acid adenosine

<400> SEQUENCE: 26
tcacgattag catta                                                15

<210> SEQ ID NO 27
<211> LENGTH: 8
<212> TYPE: DNA
<213> ORGANISM: Artificial Sequence
<220> FEATURE:
<223> OTHER INFORMATION: miR-155 8
<220> FEATURE:
<221> NAME/KEY: misc_feature
<222> LOCATION: (1)..(8)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid thymidine
<220> FEATURE:
<221> NAME/KEY: modified_base
<222> LOCATION: (2)..(2)
<223> OTHER INFORMATION: May be locked nucleic acid adenosine
<220> FEATURE:
<221> NAME/KEY: modified_base
<222> LOCATION: (3)..(3)
<223> OTHER INFORMATION: May be locked nucleic acid guanosine
<220> FEATURE:
<221> NAME/KEY: modified_base
<222> LOCATION: (4)..(4)
<223> OTHER INFORMATION: May be locked nucleic acid cytidine
<220> FEATURE:
<221> NAME/KEY: modified_base
<222> LOCATION: (5)..(5)
<223> OTHER INFORMATION: May be locked nucleic acid adenosine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid adenosine

<400> SEQUENCE: 27 tagcatta                                                         8

<210> SEQ ID NO 28
<211> LENGTH: 14
<212> TYPE: DNA
<213> ORGANISM: Artificial Sequence
<220> FEATURE:
<223> OTHER INFORMATION: miR-155 mimic 11667
<220> FEATURE:
```

```
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 28
cacgattagc atta                                                      14

<210> SEQ ID NO 29
<211> LENGTH: 14
<212> TYPE: DNA
<213> ORGANISM: Artificial Sequence
<220> FEATURE:
<223> OTHER INFORMATION: miR-155 mimic 12707
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (5)..(5)
<223> OTHER INFORMATION: May be locked nucleic acid adenosine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine
```

```
<400> SEQUENCE: 29
cacgattagc atta                                                        14

<210> SEQ ID NO 30
<211> LENGTH: 14
<212> TYPE: DNA
<213> ORGANISM: Artificial Sequence
<220> FEATURE:
<223> OTHER INFORMATION: miR-155 mimic 12708
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (5)..(5)
<223> OTHER INFORMATION: May be locked nucleic acid adenosine
<220> FEATURE:
<221> NAME/KEY: modified_base
<222> LOCATION: (7)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 30
cacgattagc atta                                                        14

<210> SEQ ID NO 31
<211> LENGTH: 14
<212> TYPE: DNA
<213> ORGANISM: Artificial Sequence
<220> FEATURE:
<223> OTHER INFORMATION: miR-155 mimic 12709
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (8)..(8)
```

```
<223> OTHER INFORMATION: May be locked nucleic acid adenosine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (13)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 31
cacgattagc atta                                                        14

<210> SEQ ID NO 32
<211> LENGTH: 14
<212> TYPE: DNA
<213> ORGANISM: Artificial Sequence
<220> FEATURE:
<223> OTHER INFORMATION: miR-155 mimic 12868
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 32
cacgattagc atta                                                        14

<210> SEQ ID NO 33
<211> LENGTH: 14
<212> TYPE: DNA
<213> ORGANISM: Artificial Sequence
<220> FEATURE:
<223> OTHER INFORMATION: miR-155 mimic 12869
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
```

```
<222> LOCATION: (2)..(2)
<223> OTHER INFORMATION: May be locked nucleic acid adenosine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 33
cacgattagc atta                                                14

<210> SEQ ID NO 34
<211> LENGTH: 14
<212> TYPE: DNA
<213> ORGANISM: Artificial Sequence
<220> FEATURE:
<223> OTHER INFORMATION: miR-155 mimic 12870
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 34
cacgattagc atta                                                14

<210> SEQ ID NO 35
<211> LENGTH: 14
<212> TYPE: DNA
<213> ORGANISM: Artificial Sequence
<220> FEATURE:
<223> OTHER INFORMATION: miR-155 mimic 12871
<220> FEATURE:
```

```
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (4)..(4)
<223> OTHER INFORMATION: May be locked nucleic acid guanosine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 35
cacgattagc atta                                                      14

<210> SEQ ID NO 36
<211> LENGTH: 14
<212> TYPE: DNA
<213> ORGANISM: Artificial Sequence
<220> FEATURE:
<223> OTHER INFORMATION: miR-155 mimic 12872
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (5)..(5)
<223> OTHER INFORMATION: May be locked nucleic acid adenosine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
```

```
<220> FEATURE:
<221> NAME/KEY: modified_base
<222> LOCATION: (14)..(14)
<223> OTHER INFORMATION: May be locked nucleic acid adenosine

<400> SEQUENCE: 36
cacgattagc atta                                                        14

<210> SEQ ID NO 37
<211> LENGTH: 14
<212> TYPE: DNA
<213> ORGANISM: Artificial Sequence
<220> FEATURE:
<223> OTHER INFORMATION: miR-155 mimic 12873
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (7)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 37
cacgattagc atta                                                        14

<210> SEQ ID NO 38
<211> LENGTH: 14
<212> TYPE: DNA
<213> ORGANISM: Artificial Sequence
<220> FEATURE:
<223> OTHER INFORMATION: miR-155 mimic 12874
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(6)
<223> OTHER INFORMATION: May be locked nucleic acid thymidine
<220> FEATURE:
<221> NAME/KEY: modified_base
<222> LOCATION: (9)..(9)
```

<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 38
cacgattagc atta                                                        14

<210> SEQ ID NO 39
<211> LENGTH: 14
<212> TYPE: DNA
<213> ORGANISM: Artificial Sequence
<220> FEATURE:
<223> OTHER INFORMATION: miR-155 mimic 12875
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 39
cacgattagc atta                                                        14

<210> SEQ ID NO 40
<211> LENGTH: 14
<212> TYPE: DNA
<213> ORGANISM: Artificial Sequence
<220> FEATURE:
<223> OTHER INFORMATION: miR-155 mimic 12876
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base

```
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 40
cacgattagc atta                                                      14

<210> SEQ ID NO 41
<211> LENGTH: 14
<212> TYPE: DNA
<213> ORGANISM: Artificial Sequence
<220> FEATURE:
<223> OTHER INFORMATION: miR-155 mimic 12877
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid cytidine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 41
cacgattagc atta                                                      14

<210> SEQ ID NO 42
<211> LENGTH: 14
<212> TYPE: DNA
```

```
<213> ORGANISM: Artificial Sequence
<220> FEATURE:
<223> OTHER INFORMATION: miR-155 mimic 12878
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 42
cacgattagc atta                                                       14

<210> SEQ ID NO 43
<211> LENGTH: 14
<212> TYPE: DNA
<213> ORGANISM: Artificial Sequence
<220> FEATURE:
<223> OTHER INFORMATION: miR-155 mimic 12879
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (13)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 43
cacgattagc atta                                                       14
```

<210> SEQ ID NO 44
<211> LENGTH: 14
<212> TYPE: DNA
<213> ORGANISM: Artificial Sequence
<220> FEATURE:
<223> OTHER INFORMATION: miR-155 mimic 12880
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(12)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 44
cacgattagc atta                                                       14

<210> SEQ ID NO 45
<211> LENGTH: 14
<212> TYPE: DNA
<213> ORGANISM: Artificial Sequence
<220> FEATURE:
<223> OTHER INFORMATION: miR-155 mimic 12881
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)

<223> OTHER INFORMATION: May be locked nucleic acid thymidine

<400> SEQUENCE: 45
cacgattagc atta                                                         14

<210> SEQ ID NO 46
<211> LENGTH: 14
<212> TYPE: DNA
<213> ORGANISM: Artificial Sequence
<220> FEATURE:
<223> OTHER INFORMATION: miR-155 mimic 12882
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (2)..(2)
<223> OTHER INFORMATION: May be locked nucleic acid adenosine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 46
cacgattagc atta                                                         14

<210> SEQ ID NO 47
<211> LENGTH: 14
<212> TYPE: DNA
<213> ORGANISM: Artificial Sequence
<220> FEATURE:
<223> OTHER INFORMATION: miR-155 mimic 12883
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (2)..(2)
<223> OTHER INFORMATION: May be locked nucleic acid adenosine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 47
cacgattagc atta                                                        14

<210> SEQ ID NO 48
<211> LENGTH: 14
<212> TYPE: DNA
<213> ORGANISM: Artificial Sequence
<220> FEATURE:
<223> OTHER INFORMATION: miR-155 mimic 12884
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(4)
<223> OTHER INFORMATION: May be locked nucleic acid guanosine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 48
cacgattagc atta                                                        14

<210> SEQ ID NO 49
<211> LENGTH: 14
<212> TYPE: DNA
<213> ORGANISM: Artificial Sequence
<220> FEATURE:
<223> OTHER INFORMATION: miR-155 mimic 12885
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:

```
<221> NAME/KEY: modified_base
<222> LOCATION: (5)..(5)
<223> OTHER INFORMATION: May be locked nucleic acid adenosine
<220> FEATURE:
<221> NAME/KEY: modified_base
<222> LOCATION: (7)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 49
cacgattagc atta                                                        14

<210> SEQ ID NO 50
<211> LENGTH: 14
<212> TYPE: DNA
<213> ORGANISM: Artificial Sequence
<220> FEATURE:
<223> OTHER INFORMATION: miR-155 mimic 12886
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 50
cacgattagc atta                                                        14

<210> SEQ ID NO 51
<211> LENGTH: 14
```

```
<212> TYPE: DNA
<213> ORGANISM: Artificial Sequence
<220> FEATURE:
<223> OTHER INFORMATION: miR-155 mimic 12887
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 51
cacgattagc atta                                                       14

<210> SEQ ID NO 52
<211> LENGTH: 14
<212> TYPE: DNA
<213> ORGANISM: Artificial Sequence
<220> FEATURE:
<223> OTHER INFORMATION: miR-155 mimic 12888
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid cytidine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
```

<223> OTHER INFORMATION: May be locked nucleic acid adenosine

<400> SEQUENCE: 52
cacgattagc atta                                                         14

<210> SEQ ID NO 53
<211> LENGTH: 14
<212> TYPE: DNA
<213> ORGANISM: Artificial Sequence
<220> FEATURE:
<223> OTHER INFORMATION: miR-155 mimic 12889
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid cytidine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 53
cacgattagc atta                                                         14

<210> SEQ ID NO 54
<211> LENGTH: 13
<212> TYPE: DNA
<213> ORGANISM: Artificial Sequence
<220> FEATURE:
<223> OTHER INFORMATION: miR-155 mimic 12890
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base -continued
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 54
acgattagca tta                                                        13

<210> SEQ ID NO 55
<211> LENGTH: 12
<212> TYPE: DNA
<213> ORGANISM: Artificial Sequence
<220> FEATURE:
<223> OTHER INFORMATION: miR-155 mimic 12891
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 55
cgattagcat ta                                                         12

<210> SEQ ID NO 56
<211> LENGTH: 11
<212> TYPE: DNA
<213> ORGANISM: Artificial Sequence
<220> FEATURE:
<223> OTHER INFORMATION: miR-155 mimic 12892
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:

```
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 56
gattagcatt a                                                            11

<210> SEQ ID NO 57
<211> LENGTH: 13
<212> TYPE: DNA
<213> ORGANISM: Artificial Sequence
<220> FEATURE:
<223> OTHER INFORMATION: miR-155 mimic 12893
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 57
acgattagca tta                                                          13

<210> SEQ ID NO 58
<211> LENGTH: 13
<212> TYPE: DNA
<213> ORGANISM: Artificial Sequence
<220> FEATURE:
<223> OTHER INFORMATION: miR-155 mimic 12894
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
```

```
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 58
acgattagca tta                                                       13

<210> SEQ ID NO 59
<211> LENGTH: 13
<212> TYPE: DNA
<213> ORGANISM: Artificial Sequence
<220> FEATURE:
<223> OTHER INFORMATION: miR-155 mimic 12895
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid guanosine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 59
acgattagca tta                                                       13

<210> SEQ ID NO 60
<211> LENGTH: 13
<212> TYPE: DNA
<213> ORGANISM: Artificial Sequence
<220> FEATURE:
<223> OTHER INFORMATION: miR-155 mimic 12896
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
```

```
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (4)..(4)
<223> OTHER INFORMATION: May be locked nucleic acid adenosine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 60
acgattagca tta                                                        13

<210> SEQ ID NO 61
<211> LENGTH: 13
<212> TYPE: DNA
<213> ORGANISM: Artificial Sequence
<220> FEATURE:
<223> OTHER INFORMATION: miR-155 mimic 12897
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (6)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 61
acgattagca tta                                                        13
```

<210> SEQ ID NO 62
<211> LENGTH: 13
<212> TYPE: DNA
<213> ORGANISM: Artificial Sequence
<220> FEATURE:
<223> OTHER INFORMATION: miR-155 mimic 12898
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(5)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 62
acgattagca tta                                                          13

<210> SEQ ID NO 63
<211> LENGTH: 13
<212> TYPE: DNA
<213> ORGANISM: Artificial Sequence
<220> FEATURE:
<223> OTHER INFORMATION: miR-155 mimic 12899
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid adenosine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:

```
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 63
acgattagca tta                                                        13

<210> SEQ ID NO 64
<211> LENGTH: 13
<212> TYPE: DNA
<213> ORGANISM: Artificial Sequence
<220> FEATURE:
<223> OTHER INFORMATION: miR-155 mimic 12900
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 64
acgattagca tta                                                        13

<210> SEQ ID NO 65
<211> LENGTH: 13
<212> TYPE: DNA
<213> ORGANISM: Artificial Sequence
<220> FEATURE:
<223> OTHER INFORMATION: miR-155 mimic 12901
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
```

```
<220> FEATURE:
<221> NAME/KEY: modified_base
<222> LOCATION: (9)..(9)
<223> OTHER INFORMATION: May be locked nucleic acid cytidine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 65
acgattagca tta                                                          13

<210> SEQ ID NO 66
<211> LENGTH: 13
<212> TYPE: DNA
<213> ORGANISM: Artificial Sequence
<220> FEATURE:
<223> OTHER INFORMATION: miR-155 mimic 12902
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 66
acgattagca tta                                                          13

<210> SEQ ID NO 67
<211> LENGTH: 13
<212> TYPE: DNA
<213> ORGANISM: Artificial Sequence
<220> FEATURE:
<223> OTHER INFORMATION: miR-155 mimic 12903
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
```

```
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine

<400> SEQUENCE: 67
acgattagca tta                                                          13

<210> SEQ ID NO 68
<211> LENGTH: 13
<212> TYPE: DNA
<213> ORGANISM: Artificial Sequence
<220> FEATURE:
<223> OTHER INFORMATION: miR-155 mimic 12904
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(11)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 68
acgattagca tta                                                          13

<210> SEQ ID NO 69
<211> LENGTH: 13
<212> TYPE: DNA
<213> ORGANISM: Artificial Sequence
<220> FEATURE:
<223> OTHER INFORMATION: miR-155 mimic 12905
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
```

```
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine

<400> SEQUENCE: 69
acgattagca tta                                                        13

<210> SEQ ID NO 70
<211> LENGTH: 13
<212> TYPE: DNA
<213> ORGANISM: Artificial Sequence
<220> FEATURE:
<223> OTHER INFORMATION: miR-155 mimic 12906
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (3)..(3)
<223> OTHER INFORMATION: May be locked nucleic acid guanosine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 70
acgattagca tta                                                        13

<210> SEQ ID NO 71
<211> LENGTH: 13
<212> TYPE: DNA
<213> ORGANISM: Artificial Sequence
<220> FEATURE:
<223> OTHER INFORMATION: miR-155 mimic 12907
<220> FEATURE:
```

```
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (4)..(4)
<223> OTHER INFORMATION: May be locked nucleic acid adenosine
<220> FEATURE:
<221> NAME/KEY: modified_base
<222> LOCATION: (6)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 71
acgattagca tta                                                          13

<210> SEQ ID NO 72
<211> LENGTH: 13
<212> TYPE: DNA
<213> ORGANISM: Artificial Sequence
<220> FEATURE:
<223> OTHER INFORMATION: miR-155 mimic 12908
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine
```

-continued

<400> SEQUENCE: 72
acgattagca tta                                                           13

<210> SEQ ID NO 73
<211> LENGTH: 13
<212> TYPE: DNA
<213> ORGANISM: Artificial Sequence
<220> FEATURE:
<223> OTHER INFORMATION: miR-155 mimic 12909
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid adenosine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 73
acgattagca tta                                                           13

<210> SEQ ID NO 74
<211> LENGTH: 13
<212> TYPE: DNA
<213> ORGANISM: Artificial Sequence
<220> FEATURE:
<223> OTHER INFORMATION: miR-155 mimic 12910
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (7)..(7)

```
<223> OTHER INFORMATION: May be locked nucleic acid adenosine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 74
acgattagca tta                                                          13

<210> SEQ ID NO 75
<211> LENGTH: 13
<212> TYPE: DNA
<213> ORGANISM: Artificial Sequence
<220> FEATURE:
<223> OTHER INFORMATION: miR-155 mimic 12911
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
<222> LOCATION: (2)..(2)
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid cytidine
<220> FEATURE:
<221> NAME/KEY: modified_base
<222> LOCATION: (10)..(10)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 75
acgattagca tta                                                          13

<210> SEQ ID NO 76
<211> LENGTH: 13
<212> TYPE: DNA
<213> ORGANISM: Artificial Sequence
<220> FEATURE:
<223> OTHER INFORMATION: miR-155 mimic 12912
<220> FEATURE:
<221> NAME/KEY: misc_feature
<222> LOCATION: (1)..(13)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid adenosine
<220> FEATURE:
<221> NAME/KEY: modified_base
```

```
<222> LOCATION: (2)..(2)
<223> OTHER INFORMATION: May be locked nucleic acid cytidine
<220> FEATURE:
<221> NAME/KEY: modified_base
<222> LOCATION: (5)..(6)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid cytidine
<220> FEATURE:
<221> NAME/KEY: modified_base
<222> LOCATION: (11)..(12)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid adenosine

<400> SEQUENCE: 76
acgattagca tta                                                        13

<210> SEQ ID NO 77
<211> LENGTH: 12
<212> TYPE: DNA
<213> ORGANISM: Artificial Sequence
<220> FEATURE:
<223> OTHER INFORMATION: miR-155 mimic 12913
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 77
cgattagcat ta                                                         12

<210> SEQ ID NO 78
<211> LENGTH: 12
<212> TYPE: DNA
<213> ORGANISM: Artificial Sequence
<220> FEATURE:
<223> OTHER INFORMATION: miR-155 mimic 12914
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
```

```
<221> NAME/KEY: modified_base
<222> LOCATION: (2)..(2)
<223> OTHER INFORMATION: May be locked nucleic acid guanosine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 78
cgattagcat ta                                                     12

<210> SEQ ID NO 79
<211> LENGTH: 12
<212> TYPE: DNA
<213> ORGANISM: Artificial Sequence
<220> FEATURE:
<223> OTHER INFORMATION: miR-155 mimic 12915
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid adenosine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 79
cgattagcat ta                                                     12

<210> SEQ ID NO 80
<211> LENGTH: 12
<212> TYPE: DNA
<213> ORGANISM: Artificial Sequence
<220> FEATURE:
<223> OTHER INFORMATION: miR-155 mimic 12916
```

```
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (5)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 80
cgattagcat ta                                                          12

<210> SEQ ID NO 81
<211> LENGTH: 12
<212> TYPE: DNA
<213> ORGANISM: Artificial Sequence
<220> FEATURE:
<223> OTHER INFORMATION: miR-155 mimic 12917
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(4)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 81
cgattagcat ta                                                          12

<210> SEQ ID NO 82
<211> LENGTH: 12
<212> TYPE: DNA
<213> ORGANISM: Artificial Sequence
<220> FEATURE:
```

```
<223> OTHER INFORMATION: miR-155 mimic 12918
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid adenosine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 82
cgattagcat ta                                                         12

<210> SEQ ID NO 83
<211> LENGTH: 12
<212> TYPE: DNA
<213> ORGANISM: Artificial Sequence
<220> FEATURE:
<223> OTHER INFORMATION: miR-155 mimic 12919
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 83
cgattagcat ta                                                         12

<210> SEQ ID NO 84
<211> LENGTH: 12
<212> TYPE: DNA
<213> ORGANISM: Artificial Sequence
```

```
<220> FEATURE:
<223> OTHER INFORMATION: miR-155 mimic 12920
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid cytidine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 84
cgattagcat ta                                                        12

<210> SEQ ID NO 85
<211> LENGTH: 12
<212> TYPE: DNA
<213> ORGANISM: Artificial Sequence
<220> FEATURE:
<223> OTHER INFORMATION: miR-155 mimic 12921
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 85
cgattagcat ta                                                        12

<210> SEQ ID NO 86
<211> LENGTH: 12
<212> TYPE: DNA
```

```
<213> ORGANISM: Artificial Sequence
<220> FEATURE:
<223> OTHER INFORMATION: miR-155 mimic 12922
<220> FEATURE:
<221> NAME/KEY: misc_feature
<222> LOCATION: (1)..(16)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (11)..(12)
<223> OTHER INFORMATION: May be locked nucleic acid thymidine

<400> SEQUENCE: 86
cgattagcat ta                                                          12

<210> SEQ ID NO 87
<211> LENGTH: 12
<212> TYPE: DNA
<213> ORGANISM: Artificial Sequence
<220> FEATURE:
<223> OTHER INFORMATION: miR-155 mimic 12923
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(10)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 87
cgattagcat ta                                                          12

<210> SEQ ID NO 88
<211> LENGTH: 12
<212> TYPE: DNA
<213> ORGANISM: Artificial Sequence
<220> FEATURE:
<223> OTHER INFORMATION: miR-155 mimic 12924
```

```
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine

<400> SEQUENCE: 88
cgattagcat ta                                                          12

<210> SEQ ID NO 89
<211> LENGTH: 12
<212> TYPE: DNA
<213> ORGANISM: Artificial Sequence
<220> FEATURE:
<223> OTHER INFORMATION: miR-155 mimic 12925
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (2)..(2)
<223> OTHER INFORMATION: May be locked nucleic acid guanosine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 89
cgattagcat ta                                                          12

<210> SEQ ID NO 90
<211> LENGTH: 12
<212> TYPE: DNA
<213> ORGANISM: Artificial Sequence
<220> FEATURE:
<223> OTHER INFORMATION: miR-155 mimic 12926
<220> FEATURE:
<221> NAME/KEY: misc_feature
<222> LOCATION: (1)..(12)
```

```
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid adenosine
<220> FEATURE:
<221> NAME/KEY: modified_base
<222> LOCATION: (5)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 90
cgattagcat ta                                                        12

<210> SEQ ID NO 91
<211> LENGTH: 12
<212> TYPE: DNA
<213> ORGANISM: Artificial Sequence
<220> FEATURE:
<223> OTHER INFORMATION: miR-155 mimic 12927
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid adenosine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 91
cgattagcat ta                                                        12
```

```
<210> SEQ ID NO 92
<211> LENGTH: 12
<212> TYPE: DNA
<213> ORGANISM: Artificial Sequence
<220> FEATURE:
<223> OTHER INFORMATION: miR-155 mimic 12928
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid adenosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 92
cgattagcat ta                                                        12

<210> SEQ ID NO 93
<211> LENGTH: 12
<212> TYPE: DNA
<213> ORGANISM: Artificial Sequence
<220> FEATURE:
<223> OTHER INFORMATION: miR-155 mimic 12929
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid cytidine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 93
cgattagcat ta                                                        12
```

<210> SEQ ID NO 94
<211> LENGTH: 12
<212> TYPE: DNA
<213> ORGANISM: Artificial Sequence
<220> FEATURE:
<223> OTHER INFORMATION: miR-155 mimic 12930
<220> FEATURE:
<221> NAME/KEY: misc_feature
<222> LOCATION: (1)..(12)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(5)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid cytidine
<220> FEATURE:
<221> NAME/KEY: modified_base
<222> LOCATION: (10)..(11)
<223> OTHER INFORMATION: May be locked nucleic acid thymidine
<220> FEATURE:
<221> NAME/KEY: modified_base
<222> LOCATION: (12)..(12)
<223> OTHER INFORMATION: May be locked nucleic acid adenosine

<400> SEQUENCE: 94
cgattagcat ta                                                          12

<210> SEQ ID NO 95
<211> LENGTH: 11
<212> TYPE: DNA
<213> ORGANISM: Artificial Sequence
<220> FEATURE:
<223> OTHER INFORMATION: miR-155 mimic 12931
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 95
gattagcatt a                                                           11

<210> SEQ ID NO 96
<211> LENGTH: 11

```
<212> TYPE: DNA
<213> ORGANISM: Artificial Sequence
<220> FEATURE:
<223> OTHER INFORMATION: miR-155 mimic 12932
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (2)..(2)
<223> OTHER INFORMATION: May be locked nucleic acid adenosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 96
gattagcatt a                                                           11

<210> SEQ ID NO 97
<211> LENGTH: 11
<212> TYPE: DNA
<213> ORGANISM: Artificial Sequence
<220> FEATURE:
<223> OTHER INFORMATION: miR-155 mimic 12933
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (4)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 97
```
gattagcatt a          11

<210> SEQ ID NO 98
<211> LENGTH: 11
<212> TYPE: DNA
<213> ORGANISM: Artificial Sequence
<220> FEATURE:
<223> OTHER INFORMATION: miR-155 mimic 12934
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(3)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 98
gattagcatt a          11

<210> SEQ ID NO 99
<211> LENGTH: 11
<212> TYPE: DNA
<213> ORGANISM: Artificial Sequence
<220> FEATURE:
<223> OTHER INFORMATION: miR-155 mimic 12935
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (5)..(5)
<223> OTHER INFORMATION: May be locked nucleic acid adenosine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base -continued
<222> LOCATION: (11)..(11)
<223> OTHER INFORMATION: May be locked nucleic acid adenosine

<400> SEQUENCE: 99
gattagcatt a          11

<210> SEQ ID NO 100
<211> LENGTH: 11
<212> TYPE: DNA
<213> ORGANISM: Artificial Sequence
<220> FEATURE:
<223> OTHER INFORMATION: miR-155 mimic 12936
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 100
gattagcatt a          11

<210> SEQ ID NO 101
<211> LENGTH: 11
<212> TYPE: DNA
<213> ORGANISM: Artificial Sequence
<220> FEATURE:
<223> OTHER INFORMATION: miR-155 mimic 12937
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (7)..(7)
<223> OTHER INFORMATION: May be locked nucleic acid cytidine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine
<220> FEATURE:

<221> NAME/KEY: modified_base
<222> LOCATION: (11)..(11)
<223> OTHER INFORMATION: May be locked nucleic acid adenosine

<400> SEQUENCE: 101
gattagcatt a                    11

<210> SEQ ID NO 102
<211> LENGTH: 11
<212> TYPE: DNA
<213> ORGANISM: Artificial Sequence
<220> FEATURE:
<223> OTHER INFORMATION: miR-155 mimic 12938
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 102
gattagcatt a                    11

<210> SEQ ID NO 103
<211> LENGTH: 11
<212> TYPE: DNA
<213> ORGANISM: Artificial Sequence
<220> FEATURE:
<223> OTHER INFORMATION: miR-155 mimic 12939
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (10)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 103
gattagcatt a                                                                  11

<210> SEQ ID NO 104
<211> LENGTH: 11
<212> TYPE: DNA
<213> ORGANISM: Artificial Sequence
<220> FEATURE:
<223> OTHER INFORMATION: miR-155 mimic 12940
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(9)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 104
gattagcatt a                                                                  11

<210> SEQ ID NO 105
<211> LENGTH: 11
<212> TYPE: DNA
<213> ORGANISM: Artificial Sequence
<220> FEATURE:
<223> OTHER INFORMATION: miR-155 mimic 12941
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine

<400> SEQUENCE: 105
gattagcatt a                                                                11

<210> SEQ ID NO 106
<211> LENGTH: 11
<212> TYPE: DNA
<213> ORGANISM: Artificial Sequence
<220> FEATURE:
<223> OTHER INFORMATION: miR-155 mimic 12942
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (2)..(2)
<223> OTHER INFORMATION: May be locked nucleic acid adenosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 106
gattagcatt a                                                                11

<210> SEQ ID NO 107
<211> LENGTH: 11
<212> TYPE: DNA
<213> ORGANISM: Artificial Sequence
<220> FEATURE:
<223> OTHER INFORMATION: miR-155 mimic 12943
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (2)..(2)
<223> OTHER INFORMATION: May be locked nucleic acid adenosine
<220> FEATURE:
<221> NAME/KEY: modified_base
<222> LOCATION: (4)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 107
gattagcatt a                                                                 11

<210> SEQ ID NO 108
<211> LENGTH: 11
<212> TYPE: DNA
<213> ORGANISM: Artificial Sequence
<220> FEATURE:
<223> OTHER INFORMATION: miR-155 mimic 12944
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(3)
<223> OTHER INFORMATION: May be locked nucleic acid thymidine
<220> FEATURE:
<221> NAME/KEY: modified_base
<222> LOCATION: (5)..(5)
<223> OTHER INFORMATION: May be locked nucleic acid adenosine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 108
gattagcatt a                                                                 11

<210> SEQ ID NO 109
<211> LENGTH: 11
<212> TYPE: DNA
<213> ORGANISM: Artificial Sequence
<220> FEATURE:
<223> OTHER INFORMATION: miR-155 mimic 12945
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (5)..(5)
<223> OTHER INFORMATION: May be locked nucleic acid adenosine
<220> FEATURE:
<221> NAME/KEY: modified_base
<222> LOCATION: (8)..(8)
<223> OTHER INFORMATION: May be locked nucleic acid adenosine
<220> FEATURE:

<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 109
gattagcatt a                                                                11

<210> SEQ ID NO 110
<211> LENGTH: 11
<212> TYPE: DNA
<213> ORGANISM: Artificial Sequence
<220> FEATURE:
<223> OTHER INFORMATION: miR-155 mimic 12946
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be locked nucleic acid cytidine
<220> FEATURE:
<221> NAME/KEY: modified_base
<222> LOCATION: (8)..(8)
<223> OTHER INFORMATION: May be locked nucleic acid adenosine
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 110
gattagcatt a                                                                11

<210> SEQ ID NO 111
<211> LENGTH: 11
<212> TYPE: DNA
<213> ORGANISM: Artificial Sequence
<220> FEATURE:
<223> OTHER INFORMATION: miR-155 mimic 12947
<220> FEATURE:
<221> NAME/KEY: misc_feature
<222> LOCATION: (1)..(11)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid guanosine
<220> FEATURE:
<221> NAME/KEY: modified_base
<222> LOCATION: (3)..(4)
<223> OTHER INFORMATION: May be locked nucleic acid thymidine
<220> FEATURE:
<221> NAME/KEY: modified_base
<222> LOCATION: (6)..(6)
<223> OTHER INFORMATION: May be locked nucleic acid guanosine
<220> FEATURE:
<221> NAME/KEY: modified_base
<222> LOCATION: (7)..(7)
<223> OTHER INFORMATION: May be locked nucleic acid cytidine

```
<220> FEATURE:
<221> NAME/KEY: modified_base
<222> LOCATION: (9)..(10)
<223> OTHER INFORMATION: May be locked nucleic acid thymidine
<220> FEATURE:
<221> NAME/KEY: modified_base
<222> LOCATION: (11)..(11)
<223> OTHER INFORMATION: May be locked nucleic acid adenosine

<400> SEQUENCE: 111
gattagcatt a                                                              11

<210> SEQ ID NO 112
<211> LENGTH: 14
<212> TYPE: DNA
<213> ORGANISM: Artificial Sequence
<220> FEATURE:
<223> OTHER INFORMATION: miR-155 mimic 12954
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be  ethylene-bridged cytidine
<220> FEATURE:
<221> NAME/KEY: modified_base
<222> LOCATION: (3)..(3)
<223> OTHER INFORMATION: May be ethylene-bridged cytidine
<220> FEATURE:
<221> NAME/KEY: modified_base
<222> LOCATION: (6)..(7)
<223> OTHER INFORMATION: May be ethylene-bridged thymidine
<220> FEATURE:
<221> NAME/KEY: modified_base
<222> LOCATION: (9)..(9)
<223> OTHER INFORMATION: May be ethylene-bridged guanosine
<220> FEATURE:
<221> NAME/KEY: modified_base
<222> LOCATION: (11)..(11)
<223> OTHER INFORMATION: May be ethylene-bridged adenosine
<220> FEATURE:
<221> NAME/KEY: modified_base
<222> LOCATION: (12)..(13)
<223> OTHER INFORMATION: May be ethylene-bridged thymidine
<220> FEATURE:
<221> NAME/KEY: modified_base
<222> LOCATION: (14)..(14)
<223> OTHER INFORMATION: May be ethylene-bridged adenosine

<400> SEQUENCE: 112
cacgattagc atta                                                           14

<210> SEQ ID NO 113
<211> LENGTH: 14
<212> TYPE: DNA
<213> ORGANISM: Artificial Sequence
<220> FEATURE:
<223> OTHER INFORMATION: miR-155 mimic 12955
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
```

```
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be ethylene-bridged adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be ethylene-bridged adenosine

<400> SEQUENCE: 113
cacgattagc atta                                                           14

<210> SEQ ID NO 114
<211> LENGTH: 14
<212> TYPE: DNA
<213> ORGANISM: Artificial Sequence
<220> FEATURE:
<223> OTHER INFORMATION: miR-155 mimic 12956
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be  ethylene-bridged cytidine
<220> FEATURE:
<221> NAME/KEY: modified_base
<222> LOCATION: (3)..(3)
<223> OTHER INFORMATION: May be ethylene-bridged cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 114
cacgattagc atta                                                           14

<210> SEQ ID NO 115
<211> LENGTH: 14
<212> TYPE: DNA
<213> ORGANISM: Artificial Sequence
<220> FEATURE:
<223> OTHER INFORMATION: miR-155 mimic 12957
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
```

```
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be ethylene-bridged guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 115
cacgattagc atta                                                        14

<210> SEQ ID NO 116
<211> LENGTH: 14
<212> TYPE: DNA
<213> ORGANISM: Artificial Sequence
<220> FEATURE:
<223> OTHER INFORMATION: miR-155 mimic 12958
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be ethylene-bridged thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be ethylene-bridged thymidine
<220> FEATURE:
<221> NAME/KEY: modified_base
<222> LOCATION: (14)..(14)
<223> OTHER INFORMATION: May be locked nucleic acid adenosine

<400> SEQUENCE: 116
cacgattagc atta                                                        14

<210> SEQ ID NO 117
<211> LENGTH: 14
<212> TYPE: DNA
```

```
<213> ORGANISM: Artificial Sequence
<220> FEATURE:
<223> OTHER INFORMATION: miR-155 mimic 12959
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(6)
<223> OTHER INFORMATION: May be locked nucleic acid thymidine
<220> FEATURE:
<221> NAME/KEY: modified_base
<222> LOCATION: (7)..(7)
<223> OTHER INFORMATION: May be ethylene-bridged thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be locked nucleic acid adenosine

<400> SEQUENCE: 117
cacgattagc atta                                                      14

<210> SEQ ID NO 118
<211> LENGTH: 14
<212> TYPE: DNA
<213> ORGANISM: Artificial Sequence
<220> FEATURE:
<223> OTHER INFORMATION: miR-155 mimic 12960
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be locked nucleic acid adenosine
<220> FEATURE:
<221> NAME/KEY: modified_base
<222> LOCATION: (12)..(12)
<223> OTHER INFORMATION: May be locked nucleic acid thymidine
```

```
<220> FEATURE:
<221> NAME/KEY: modified_base
<222> LOCATION: (13)..(13)
<223> OTHER INFORMATION: May be ethylene-bridged thymidine
<220> FEATURE:
<221> NAME/KEY: modified_base
<222> LOCATION: (14)..(14)
<223> OTHER INFORMATION: May be locked nucleic acid adenosine

<400> SEQUENCE: 118
cacgattagc atta                                                         14

<210> SEQ ID NO 119
<211> LENGTH: 14
<212> TYPE: DNA
<213> ORGANISM: Artificial Sequence
<220> FEATURE:
<223> OTHER INFORMATION: miR-155 mimic 12961
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (3)..(3)
<223> OTHER INFORMATION: May be locked nucleic acid cytidine
<220> FEATURE:
<221> NAME/KEY: modified_base
<222> LOCATION: (6)..(7)
<223> OTHER INFORMATION: May be locked nucleic acid thymidine
<220> FEATURE:
<221> NAME/KEY: modified_base
<222> LOCATION: (9)..(9)
<223> OTHER INFORMATION: May be locked nucleic acid guanosine
<220> FEATURE:
<221> NAME/KEY: modified_base
<222> LOCATION: (11)..(11)
<223> OTHER INFORMATION: May be amino-2'-C-bridged bicyclic adenosine
<220> FEATURE:
<221> NAME/KEY: modified_base
<222> LOCATION: (12)..(13)
<223> OTHER INFORMATION: May be locked nucleic acid thymidine
<220> FEATURE:
<221> NAME/KEY: modified_base
<222> LOCATION: (14)..(14)
<223> OTHER INFORMATION: May be amino-2'-C-bridged bicyclic adenosine

<400> SEQUENCE: 119
cacgattagc atta                                                         14

<210> SEQ ID NO 120
<211> LENGTH: 14
<212> TYPE: DNA
<213> ORGANISM: Artificial Sequence
<220> FEATURE:
<223> OTHER INFORMATION: miR-155 mimic 12552
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be amino-2'-C-bridged bicyclic cytidine
<220> FEATURE:
<221> NAME/KEY: modified_base
<222> LOCATION: (3)..(3)
<223> OTHER INFORMATION: May be amino-2'-C-bridged bicyclic cytidine
<220> FEATURE:
<221> NAME/KEY: modified_base
<222> LOCATION: (6)..(7)
```

-continued

<223> OTHER INFORMATION: May be amino-2'-C-bridged bicyclic thymidine
<220> FEATURE:
<221> NAME/KEY: modified_base
<222> LOCATION: (9)..(9)
<223> OTHER INFORMATION: May be amino-2'-C-bridged bicyclic guanosine
<220> FEATURE:
<221> NAME/KEY: modified_base
<222> LOCATION: (11)..(11)
<223> OTHER INFORMATION: May be amino-2'-C-bridged bicyclic adenosine
<220> FEATURE:
<221> NAME/KEY: modified_base
<222> LOCATION: (12)..(13)
<223> OTHER INFORMATION: May be amino-2'-C-bridged bicyclic thymidine
<220> FEATURE:
<221> NAME/KEY: modified_base
<222> LOCATION: (14)..(14)
<223> OTHER INFORMATION: May be amino-2'-C-bridged bicyclic adenosine

<400> SEQUENCE: 120
cacgattagc atta                                                         14

<210> SEQ ID NO 121
<211> LENGTH: 23
<212> TYPE: RNA
<213> ORGANISM: Artificial Sequence
<220> FEATURE:
<223> OTHER INFORMATION: Dharmacon miRIDIAN microRNA Human hsa-miR-
      155-5p mimic

<400> SEQUENCE: 121
uuaaugcuaa ucgugauagg ggu                                               23

<210> SEQ ID NO 122
<211> LENGTH: 14
<212> TYPE: DNA
<213> ORGANISM: Artificial Sequence
<220> FEATURE:
<223> OTHER INFORMATION: miR-155 control oligo 11317
<220> FEATURE:
<221> NAME/KEY: misc_feature
<222> LOCATION: (1)..(14)
<223> OTHER INFORMATION: May be joined through phosphorothioate bonds
<220> FEATURE:
<221> NAME/KEY: modified_base
<222> LOCATION: (1)..(1)
<223> OTHER INFORMATION: May be locked nucleic acid cytidine
<220> FEATURE:
<221> NAME/KEY: modified_base
<222> LOCATION: (4)..(4)
<223> OTHER INFORMATION: May be locked nucleic acid guanosine
<220> FEATURE:
<221> NAME/KEY: modified_base
<222> LOCATION: (6)..(6)
<223> OTHER INFORMATION: May be locked nucleic acid adenosine
<220> FEATURE:
<221> NAME/KEY: modified_base
<222> LOCATION: (8)..(8)
<223> OTHER INFORMATION: May be locked nucleic acid guanosine
<220> FEATURE:
<221> NAME/KEY: modified_base
<222> LOCATION: (9)..(9)
<223> OTHER INFORMATION: May be locked nucleic acid adenosine
<220> FEATURE:
<221> NAME/KEY: modified_base
<222> LOCATION: (11)..(11)
<223> OTHER INFORMATION: May be locked nucleic acid thymidine
<220> FEATURE:
<221> NAME/KEY: modified_base
<222> LOCATION: (13)..(13)
<223> OTHER INFORMATION: May be locked nucleic acid guanosine
<220> FEATURE:

```
<221> NAME/KEY: modified_base
<222> LOCATION: (14)..(14)
<223> OTHER INFORMATION: May be locked nucleic acid adenosine

<400> SEQUENCE: 122
ctagaaagag taga                                              14
```

OLIGONUCLEOTIDE COMPOSITIONS AND USES THEREOF

CROSS REFERENCE TO RELATED APPLICATIONS

The present application is a continuation of Ser. No. 15/714,671, filed on Sep. 25, 2017, now U.S. Pat. No. 9,994,852, which is a continuation of PCT Application No. PCT/US2016/035865, filed on Jun. 3, 2016, which claims the benefit of priority to U.S. Provisional Application No. 62/171,758, filed on Jun. 5, 2015, the contents of each of which are hereby incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_051_04US_SeqList_ST25.txt, date recordeed May 10, 2018, file size 112 KB).

FIELD OF THE INVENTION

The present invention relates to oligonucleotide inhibitors of miR-155 and compositions thereof. The invention also provides methods for treating or preventing cancer in a subject in need thereof by administering an oligonucleotide inhibitor of miR-155. The activity or function of miR-155 is reduced in cancer cells of the subject following administration of the oligonucleotide inhibitor.

BACKGROUND

MicroRNAs (miRNAs) are small, endogenous, noncoding RNAs that act as posttranscriptional repressors of gene expression. MiRNAs act as repressors of target mRNAs by promoting their degradation, when their sequences are perfectly complementary, or by inhibiting translation, when their sequences contain mismatches.

MiRNAs are transcribed by RNA polymerase II (pol II) or RNA polymerase III (pol III; see Qi et al. (2006) *Cellular & Molecular Immunology*, Vol. 3:411-419) and arise from initial transcripts, termed primary miRNA transcripts (pri-miRNAs), that are generally several thousand bases long. Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA. The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

MicroRNAs have been implicated in several diseases including cancer. For example, human miRNA genes miR15a and miR16-1 are deleted or down-regulated in approximately 60% of B-cell chronic lymphocytic leukemia (CLL) cases (Calin et al., Proc Natl Acad Sci, 2002; 99:15524-15529). Similarly, dysregulation of miR-155-5p has been linked to signaling events that are implicated in the pathogenesis of cutaneous T cell lymphoma (CTCL). It has been shown that malignant T-cells constitutively express an IL-2 receptor complex and associated Janus kinases (JAKs) that activate transcription via signal transducers and activators of transcription (STAT) proteins. Chromatin immunoprecipitation experiments showed that STAT-5 was associated with the promoter of MIR155HG, a host gene for miR-155-5p. This suggests that miR-155-5p may regulate the STAT-5 signaling pathway in CTCL malignant T-cells. Inhibition of the JAK/STAT pathway resulted in the down-regulation of miR-155-5p expression whereas treatment of cells with cytokines that activate STAT-5 resulted in increased miR-155-5p levels (Kopp et al. 2013). These results suggest that miR-155-5p may play a role in the pathogenesis of CTCL.

Currently there are no therapies that cure or prolong the survival of late-stage CTCL patients (Prince et al., 2009). Treatments for CTCL patients at an early-stage of disease are palliative and non-aggressive with careful physician monitoring. More advanced-stage CTCL patients are typically treated with systemic drugs, such as retinoids (bexarotene) or histone deacetylase inhibitors (vorinostat). Radiotherapy is typically the last line of defense and can result in partial disease regression but not full eradication. Many treatments have serious side effects or result in resistance over time. Thus, there remains an unmet medical need for new therapies to treat cutaneous T-cell lymphoma.

SUMMARY OF THE INVENTION

The present invention provides oligonucleotide inhibitors for modulating the activity or function of miR-155 in cells of a subject. In one embodiment, administration of an oligonucleotide inhibitor of miR-155 down-regulates the activity or function of miR-155 in cancer cells of the subject following administration. In certain embodiments, cancer cells are malignant T cells including cutaneous T cell lymphoma (CTCL) cells, CD4$^+$ T cells, CD8$^+$ T cells, αβ T cells, γδ T cells and memory T cells.

In one embodiment, the oligonucleotide inhibitor of miR-155 comprises a sequence of 11 to 16 nucleotides, wherein the oligonucleotide inhibitor is fully complementary to a mature sequence of miR-155 and has a full phosphorothioate backbone; and wherein at least the first three nucleotides from the 3' end of the oligonucleotide inhibitor are locked nucleotides and at least the second nucleotide from the 5' end of the oligonucleotide inhibitor is a deoxyribonucleic acid (DNA) nucleotide. In some of these embodiments, the fourth nucleotide from the 3' end of the oligonucleotide inhibitor is also a locked nucleotide. In some of these embodiments, the first nucleotide from the 5' end of the oligonucleotide inhibitor is a locked nucleotide.

In another embodiment, the oligonucleotide inhibitor of miR-155 comprises a sequence of 11 to 14 nucleotides, wherein the oligonucleotide inhibitor is fully complementary to a mature sequence of miR-155 and has a full phosphorothioate backbone; and wherein at least the first three nucleotides from the 3' end of said oligonucleotide inhibitor are modified nucleotides and at least the second nucleotide from the 5' end of the oligonucleotide inhibitor is a deoxyribonucleic acid (DNA) nucleotide. In these embodiments, the oligonucleotide inhibitor may contain at least 5, 6, 7, 8, 9, or 10 modified nucleotides. In some of these embodiments, the oligonucleotide inhibitor contains 7, 8, 9, or 10 modified nucleotides. In some of these embodiments, 7, 8, 9, or 10 modified nucleotides present in the oligonucleotide inhibitor are all locked nucleotides. In yet some other embodiments, 7, 8, 9, or 10 modified nucleotides present in the oligonucleotide inhibitor are a combination of locked nucleotides and other modifications such as ethylene-bridged nucleotides, 2'-C-bridged bicyclic nucleotides, and sugar modifications such as 2'-substituted nucleotides. In some of these embodiments, the second DNA nucleotide from the 5' end of the oligonucleotide inhibitor could be an unmodified DNA nucleotide. In some of these embodiments, the first three modified nucleotides from the 3' end of the oligonucleotide inhibitor are locked nucleotides.

In yet another embodiment, the oligonucleotide inhibitor of miR-155 comprises a sequence of 11 to 14 nucleotides, wherein the oligonucleotide inhibitor is fully complementary to a mature sequence of miR-155 and has a full phosphorothioate backbone; and wherein at least 7 nucleotides of said oligonucleotide inhibitor are modified nucleotides and at least the second nucleotide from the 5' end of the oligonucleotide inhibitor is a deoxyribonucleic acid (DNA) nucleotide. In these embodiments, the oligonucleotide inhibitor may contain at least 7, 8, 9, or 10 modified nucleotides. In some of these embodiments, 7, 8, 9, or 10 modified nucleotides present in the oligonucleotide inhibitor are all locked nucleotides. In yet some other embodiments, 7, 8, 9, or 10 modified nucleotides present in the oligonucleotide inhibitor are a combination of locked nucleotides and other modifications such as ethylene-bridged nucleotides, 2'-C-bridged bicyclic nucleotides, and sugar modifications such as 2'-substituted nucleotides. In some of these embodiments, the first three nucleotides from the 3' end of the oligonucleotide inhibitor are modified nucleotides. In some of these embodiments, the first three modified nucleotides from the 3' end of the oligonucleotide inhibitor are locked nucleotides. In some of these embodiments, the second or the third nucleotide from the 3' end of the oligonucleotide inhibitor is a DNA nucleotide. In some of these embodiments, the second DNA nucleotide from the 5' end of the oligonucleotide inhibitor could be an unmodified DNA nucleotide.

In yet another embodiment, the oligonucleotide inhibitor of miR-155 comprises a sequence of 11 to 14 nucleotides, wherein the oligonucleotide inhibitor is fully complementary to a mature sequence of miR-155 and has a full phosphorothioate backbone; and wherein at least the first three nucleotides from 3' end of said oligonucleotide inhibitor are modified nucleotides and at least the fourth and fifth nucleotides from the 5' end of the oligonucleotide inhibitor are deoxyribonucleic acid (DNA) nucleotides. In these embodiments, the oligonucleotide inhibitor may contain at least 7, 8, 9, or 10 modified nucleotides. In some of these embodiments, 7, 8, 9, or 10 modified nucleotides present in the oligonucleotide inhibitor are all locked nucleotides. In some of these embodiments, the first three modified nucleotides from the 3' end of the oligonucleotide inhibitor are locked nucleotides. In some of these embodiments, the fourth and/or the fifth DNA nucleotide from the 5' end of the oligonucleotide inhibitor could be an unmodified DNA nucleotide.

The modified nucleotides that may be present in the oligonucleotide inhibitors of the present invention include, but are not limited to, locked nucleotides, ethylene-bridged nucleotides, 2'-C-bridged bicyclic nucleotides, 2'-substituted nucleotides, and other sugar and/or base modifications described herein. In some embodiments, all modified nucleotides present in the oligonucleotide inhibitors of the present invention are locked nucleotides. In some other embodiments, modified nucleotides present in the oligonucleotide inhibitors are a combination of locked nucleotides and other modifications such as ethylene-bridged nucleotides, 2'-C-bridged bicyclic nucleotides, and 2'-substituted nucleotides, and other sugar and/or base modifications described herein.

In one embodiment, the oligonucleotide inhibitor of miR-155 has a length of 12 to 14 nucleotides. In some embodiments, the oligonucleotide inhibitor contains at least 5, 6, 7, 8, 9 or 10 locked nucleotides. In some other embodiments, the oligonucleotide inhibitor contains at least 1, 2, 3, 4, 5, or more DNA nucleotides. In certain embodiments, at least the second nucleotide from the 5' end of the oligonucleotide inhibitor is a DNA nucleotide. In certain additional embodiments, at least the second and fourth nucleotides from the 5' end of the oligonucleotide inhibitor are DNA nucleotides. In further embodiments, at least the sixth and/or the eighth nucleotide from the 5' end of the oligonucleotide inhibitor is a DNA nucleotide. In yet further embodiments, the oligonucleotide inhibitor comprises DNA nucleotides at the second, sixth, and the eighth position from the 5' end.

In some embodiments, the oligonucleotide inhibitor of miR-155 has a sequence selected from SEQ ID NOs: 3-27 and 29-120. In an exemplary embodiment, the oligonucleotide inhibitor of miR-155 has a sequence of SEQ ID NO: 25. In another exemplary embodiment, the oligonucleotide inhibitor of miR-155 has a sequence of SEQ ID NO: 22 or 23. In yet another exemplary embodiment, the oligonucleotide inhibitor of miR-155 has a sequence selected from SEQ ID NO: 33, 39, 43, 44, 47, 58, 84, 99, 111, 115, and 120.

In one embodiment, oligonucleotide inhibitors of miR-155 according to the present invention reduce or inhibit proliferation of cancer cells and/or induce apoptosis of cancer cells. In another embodiment, oligonucleotide inhibitors up-regulate one or more target genes of miR-155 in cancer cells.

The present invention also provides compositions comprising oligonucleotide inhibitors of miR-155 and uses thereof. In one embodiment, the invention provides methods for treating cancer in a subject in need thereof, comprising administering to the subject a therapeutically effective amount of an oligonucleotide inhibitor of miR-155 of the present invention. The activity or function of miR-155 is reduced in cancer cells following administration of the oligonucleotide inhibitor. In one embodiment, the cancer is a cutaneous T cell lymphoma (CTCL). In some embodiments, methods for treating cancer comprise administering to a subject a therapeutically effective amount of an oligonucleotide inhibitor of miR-155 of the invention and a therapeutically effective amount of a second therapeutic agent such as a retinoid or a histone deacetylase (HDAC) inhibitor.

In one embodiment, the invention provides methods for reducing or inhibiting the proliferation of malignant T cells, comprising administering the oligonucleotide inhibitor of miR-155 according to the invention. The activity or function of miR-155 is reduced in malignant T cells following administration of the oligonucleotide inhibitor.

BRIEF DESCRIPTION OF THE DRAWINGS

FIG. 3A shows a fold-change in the expression of four miR-155 target genes in response to treatment with 2 μM antimiR-155 compounds for 72 hours in HuT102 cells. FIG. 3B shows a fold-change in the expression of four miR-155 target genes in response to treatment with 10 μM antimiR-155 compounds for 72 hours in HuT102 cells. FIG. 3C shows a fold-change in the expression of four miR-155 target genes in response to treatment with 50 μM antimiR-155 compounds for 72 hours in HuT102 cells. FIG. 3D shows a fold-change in the expression of four miR-155 target genes in response to treatment with 2 μM antimiR-155 compounds for 96 hours in HuT102 cells. FIG. 3E shows a fold-change in the expression of four miR-155 target genes in response to treatment with 10 μM antimiR-155 compounds for 96 hours in HuT102 cells. FIG. 3F shows a fold-change in the expression of four miR-155 target genes in response to treatment with 50 μM antimiR-155 compounds for 96 hours in HuT102 cells. * p-value<0.0001 compared to untreated by nonparametric Mann-Whitney test.

FIG. 4A shows a fold-change in the expression of four miR-155 target genes in response to treatment with 2 μM antimiR-155 compounds for 72 hours in MJ cells. FIG. 4B shows a fold-change in the expression of four miR-155 target genes in response to treatment with 10 μM antimiR-155 compounds for 72 hours in MJ cells. FIG. 4C shows a fold-change in the expression of four miR-155 target genes in response to treatment with 50 μM antimiR-155 compounds for 72 hours in MJ cells. FIG. 4D shows a fold-change in the expression of four miR-155 target genes in response to treatment with 2 μM antimiR-155 compounds for 96 hours in MJ cells. FIG. 4E shows a fold-change in the expression of four miR-155 target genes in response to treatment with 10 μM antimiR-155 compounds for 96 hours in MJ cells. FIG. 4F shows a fold-change in the expression of four miR-155 target genes in response to treatment with 50 μM antimiR-155 compounds for 96 hours in MJ cells. * p-value<0.0001 compared to untreated by nonparametric Mann-Whitney test.

FIG. 5A shows a fold-change in the expression of four miR-155 target genes in response to treatment with 2 μM antimiR-155 compounds for 72 hours in HH cells. FIG. 5B shows a fold-change in the expression of four miR-155 target genes in response to treatment with 10 μM antimiR-155 compounds for 72 hours in HH cells. FIG. 5C shows a fold-change in the expression of four miR-155 target genes in response to treatment with 50 μM antimiR-155 compounds for 72 hours in HH cells. FIG. 5D shows a fold-change in the expression of four miR-155 target genes in response to treatment with 2 μM antimiR-155 compounds for 96 hours in HH cells. FIG. 5E shows a fold-change in the expression of four miR-155 target genes in response to treatment with 10 μM antimiR-155 compounds for 96 hours in HH cells. FIG. 5F shows a fold-change in the expression of four miR-155 target genes in response to treatment with 50 μM antimiR-155 compounds for 96 hours in HH cells. * p-value<0.0001 compared to untreated by nonparametric Mann-Whitney test.

FIG. 7A shows a fold-change in the expression of four miR-155 target genes in response to treatment with 2 μM antimiR-155 compounds for 72 hours in HuT78 cells. FIG. 7B shows a fold-change in the expression of four miR-155 target genes in response to treatment with 10 μM antimiR-155 compounds for 72 hours in HuT78 cells. FIG. 7C shows a fold-change in the expression of four miR-155 target genes in response to treatment with 50 μM antimiR-155 compounds for 72 hours in HuT78 cells. FIG. 7D shows a fold-change in the expression of four miR-155 target genes in response to treatment with 2 μM antimiR-155 compounds for 96 hours in HuT78 cells. FIG. 7E shows a fold-change in the expression of four miR-155 target genes in response to treatment with 10 μM antimiR-155 compounds for 96 hours in HuT78 cells. FIG. 7F shows a fold-change in the expression of four miR-155 target genes in response to treatment with 50 μM antimiR-155 compounds for 96 hours in HuT78 cells.

DETAILED DESCRIPTION

Figure 1:
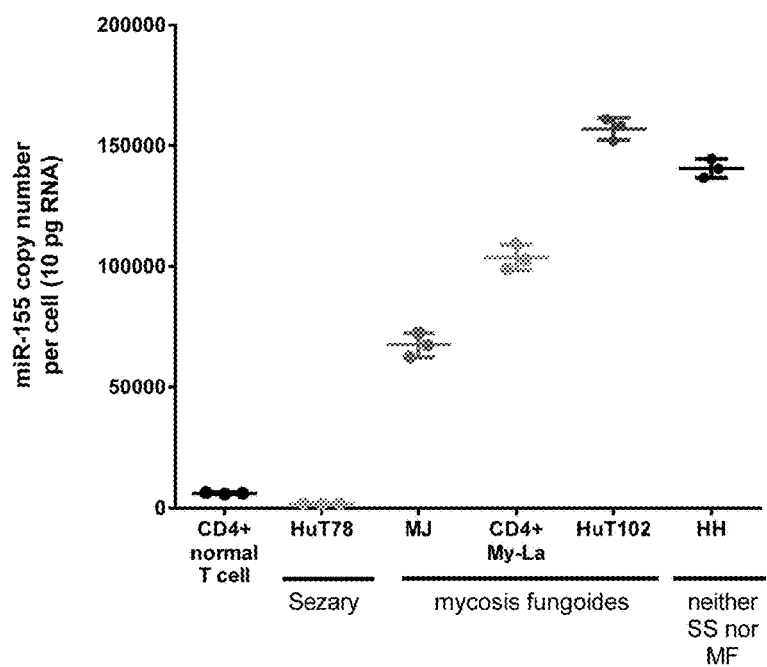
FIG. 1 shows the absolute expression of miR-155-5p in various CTCL cell lines compared to normal peripheral CD4$^+$ T helper cells as measured by quantitative real time PCR.

All patent and non-patent documents referenced throughout this disclosure are incorporated by reference herein in their entirety.

The present invention provides oligonucleotide inhibitors that inhibit the activity or function of miR-155 in cancer cells. In humans, miR-155 is encoded by the MIR155 host gene or MIR155HG and is located on human chromosome 21. Since both arms of pre-miR-155 can give rise to mature miRNAs, processing products of pre-miR-155 are designated as miR-155-5p (from the 5' arm) and miR-155-3p (from the 3' arm). The mature sequences for human miR-155-5p and miR-155-3p are given below:

```
Human mature miR-155-5p
                                   (SEQ ID NO: 1)
5'-UUAAUGCUAAUCGUGAUAGGGGU-3'

Human mature miR-155-3p
                                   (SEQ ID NO: 2)
5'-CUCCUACAUAUUAGCAUUAACA-3'
``` miR-155-5p is expressed in hematopoietic cells including B-cells, T-cells, monocytes and granulocytes (Landgraf et al. 2007). miR-155-5p is an essential molecule in the control of both myelopoiesis and erythropoiesis. This miRNA is highly expressed in hematopoietic stem-progenitor cells at an early stem-progenitor stage, and blocks their differentiation into a more mature hematopoietic cell (e.g., lymphocyte, erythrocyte). miR-155-5p expression progressively decreases as cells mature along these lineages, and is ~200-fold lower in mature hematopoietic cells (Masaki et al. 2007; Gerloff et al. 2015).

miR-155-5p plays an important role in mediating inflammatory and immune responses. Mice lacking miR-155-5p show normal number and distribution of T- and B-lymphocyte subpopulations, but display a deficient immune response, specifically in regulating T helper cell differentiation and the germinal center reaction to produce an optimal T-cell dependent antibody response (Rodriguez et al. 2007; Thai et al. 2007). miR-155-5p controls differentiation of CD4+ T-cells into the T helper type 1 (Th1), Th2, and Th17 subsets of T helper cells, and affects the development of regulatory T-cells (Treg) (Baumjohann and Ansel 2013). miR-155-5p also regulates effector and memory CD8+ T-cell responses to viral infection (Dudda et al. 2013; Gracias et al. 2013), as well as normal B-cell differentiation and antibody production. In humans, miR-155-5p expression is low in nonlymphoid organs as well as in resting, naïve CD4+ T-cells. miR-155-5p expression is greatly enhanced by antigen receptor stimulation of B- and T-cells (Tam 2001; Haasch et al. 2002; van den Berg et al. 2003; Rodriguez et al. 2007; Thai et al. 2007; Vigorito et al. 2007; Banerjee et al. 2010), and by Toll-like receptor agonist stimulation of macrophages and dendritic cells (Taganov et al. 2006; O'Connell et al. 2007; Ceppi et al. 2009; Mao et al. 2011). MIR155HG activation involves both API- and NF-κB-mediated mechanisms.

Cutaneous plaques or tumors in patients diagnosed with mycosis fungoides (MF) subtype of CTCL, have elevated levels of miR-155-5p. Increased miR-155-5p in MF patient skin biopsies compared to control skin biopsies has been reported by several groups (van Kester et al. 2011; Maj et al. 2012; Kopp et al. 2013b; Moyal et al. 2013). In one study, miR-155-5p levels were 4.16-fold higher in tumor-stage biopsies compared to early MF biopsies (Moyal et al. 2013), suggesting that miR-155-5p levels may be correlated with disease progression. In a second study directed to identifying specific cell types that express miR-155-5p, the miRNA was found to be expressed in both malignant and non-malignant T-cells in the CTCL lesions (Kopp et al. 2013b).

Mycosis fungoides (MF) is the most prevalent sub-type of CTCL, accounting for 50-70% of all primary cutaneous lymphomas. The second most prevalent sub-type is Sézary syndrome (SS), comprising 15% of CTCL cases. MF is characterized by proliferation of atypical small- to medium-sized T lymphocytes with cerebriform nuclei that form patches, plaques, or nodular tumors in the epidermis. MF typically affects older adults (median age of diagnosis: 55-60) and has an indolent clinical course where patches and plaques precede or are concurrent with the formation of tumors. In some late tumor-stage cases, lymph node and visceral organ involvment are observed. During tumor-stage MF, the dermal infiltrates become more diffuse and the epidermotropism of the atypical T-cells may be lost. In contrast, SS is a more aggressive, leukemic form of CTCL, characterized by widespread redness and scaling of the skin (erythroderma), enlarged lymph nodes, and malignant cells in the peripheral circulation (Yamashita et al., 2012; Jawed et al. 2014).

Molecular analyses of tumor stage MF have revealed significant changes in gene expression compared to normal skin, inflamed skin and normal T-cells (van Kester et al. 2012), although the genetic or epigenetic origin of these differences in gene expression are unknown. Early skin lesions contain numerous inflammatory cells, including T cells with a normal phenotype as well as a smaller population of T cells with an abnormal morphology and a malignant phenotype. The infiltrate primarily consists of non-malignant Th1 cells, regulatory T cells, and cytotoxic CD8+ T cells. The malignant T cells are typically CD4+ memory T cells of clonal origin. During disease development, epidermotropism is gradually lost, comcomitant with an increase in malignant CD4+ T cells and a decrease in non-malignant CD8+ T cells.

CTCL is characterized by aberrant expression and function of transcription factors and regulators of signal transduction. It has been hypothesized that dysfunctional regulation of signal molecules and cytokines plays a key role in the malignant transformation and pathogenesis of CTCL (Girardi et al., 2004; Zhang et al., 2006; van Doom et al., 2009; Kadin and Vonderheid, 2010). Significant differences in the gene expression profiles of MF and SS cells have been observed, consistent with a distinct pathogenesis for these variants of CTCL (van Doom et al., 2009; Campbell et al., 2010). Recently, microRNAs (miRNAs) have been reported to be differentially expressed and potentially involved in the pathogenesis of CTCL. miR-155-5p is among the miRNAs most up-regulated in mycosis fungoides (Kopp et al, 2013a; Kopp et al., 2013b), while a distinct subset of dysregulated miRNAs distinguishes Sezary syndrome, and miR-155-5p is not up-regulated in this subtype of CTCL (Ballabio et al., 2010).

The present invention provides oligonucleotide inhibitors that reduce or inhibit the activity or function of human miR-155. In the context of the present invention, the term "oligonucleotide inhibitor", "antimiR" (e.g., antimiR-155), "antagonist", "antisense oligonucleotide or ASO", "oligomer", "anti-microRNA oligonucleotide or AMO", or "mixmer" is used broadly and encompasses an oligomer comprising ribonucleotides, deoxyribonucleotides, modified ribonucleotides, modified deoxyribonucleotides or a combination thereof, that inhibits the activity or function of the target microRNA (miRNA) by fully or partially hybridizing to the miRNA thereby repressing the function or activity of the target miRNA.

The term "miR-155" as used herein includes pri-miR-155, pre-miR-155, miR-155-5p, and hsa-miR-155-5p.

In one embodiment, the present invention provides an oligonucleotide inhibitor of miR-155 that has a length of 11 to 16 nucleotides. In some other embodiments, the present invention provides an oligonucleotide inhibitor of miR-155 that has a length of 11 to 14 nucleotides. In various embodiments, the oligonucleotide inhibitor targeting miR-155 is 11, 12, 13, 14, 15, or 16 nucleotides in length. In one embodiment, the oligonucleotide inhibitor of miR-155 has a length of 12 nucleotides. In another embodiment, the oligonucleotide inhibitor of miR-155 has a length of 14 nucleotides.

The sequence of an oligonucleotide inhibitor of miR-155 according to the invention is sufficiently complementary to a mature sequence of miR-155-5p to hybridize to miR-155-5p under physiological conditions and inhibit the activity or function of miR-155-5p in the cells of a subject. For instance, in some embodiments, oligonucleotide inhibitors comprise a sequence that is at least partially complementary to a mature sequence of miR-155-5p, e.g. at least about 75%, 80%, 85%, 90%, 95%, 96%, 97%, 98%, or 99% complementary to a mature sequence of miR-155-5p. In some embodiments, the oligonucleotide inhibitor can be substantially complementary to a mature sequence of miR-155-5p, that is at least about 90%, 95%, 96%, 97%, 98%, or 99% complementary to a mature sequence of miR-155-5p. In one embodiment, the oligonucleotide inhibitor comprises a sequence that is 100% or fully complementary to a mature sequence of miR-155-5p. It is understood that the sequence of the oligonucleotide inhibitor is considered to be complementary to miR-155 even if the oligonucleotide sequence includes a modified nucleotide instead of a naturally-occurring nucleotide. For example, if a mature sequence of miR-155 comprises a guanosine nucleotide at a specific position, the oligonucleotide inhibitor may comprise a modified cytidine nucleotide, such as a locked cytidine nucleotide or 2'-fluoro-cytidine, at the corresponding position.

The term "about" as used herein encompasses variations of +/−10% and more preferably +/−5%, as such variations are appropriate for practicing the present invention.

In some embodiments, the entire sequence of the oligonucleotide inhibitor of miR-155 is fully complementary to a mature sequence of human miR-155-5p. In various embodiments, the mature sequence of human miR-155-5p to which the sequence of the oligonucleotide inhibitor of the present invention is partially, substantially, or fully complementary to includes nucleotides 1-17, or nucleotides 2-17, or nucleotides 2-16, or nucleotides 2-15, or nucleotides 2-14, or nucleotides 2-13, or nucleotides 2-12 from the 5' end of SEQ ID NO: 1. In one embodiment, the mature sequence of human miR-155-5p to which the sequence of the oligonucleotide inhibitor of the present invention is partially, substantially, or fully complementary to includes nucleotides 2-15 from the 5' end of SEQ ID NO: 1. In another embodiment, the mature sequence of human miR-155-5p to which the sequence of the oligonucleotide inhibitor of the present invention is partially, substantially, or fully complementary to includes nucleotides 2-13 from the 5' end of SEQ ID NO: 1.

In one embodiment, the oligonucleotide inhibitor of miR-155 contains at least one backbone modification, such as at least one phosphorothioate, morpholino, or phosphonocarboxylate internucleotide linkage (see, for example, U.S. Pat. Nos. 6,693,187 and 7,067,641, which are herein incorporated by reference in their entireties). In certain embodiments, the oligonucleotide inhibitor of miR-155 is fully phosphorothioate-linked.

In one embodiment, the oligonucleotide inhibitor of miR-155 contains at least one modified nucleotide. In some embodiments, the oligonucleotide inhibitor contains at least 5, 6, 7, 8, 9, 10, or more modified nucleotides. The term "modified nucleotide" as used herein encompasses nucleotides with sugar, base, and/or backbone modifications. Examples of modified nucleotides include, but are not limited to, locked nucleotides (LNA), ethylene-bridged nucleotides (ENA), 2'-C-bridged bicyclic nucleotide (CBBN), 2', 4'-constrained ethyl nucleic acid called S-cEt or cEt, 2'-4'-carbocyclic LNA, and 2' substituted nucleotides.

The terms "locked nucleotide," "locked nucleic acid unit," "locked nucleic acid residue," or "LNA unit" may be used interchangeably throughout the disclosure and refer to a bicyclic nucleoside analogue. For instance, suitable oligonucleotide inhibitors can be comprised of one or more "conformationally constrained" or bicyclic sugar nucleoside modifications (BSN) that confer enhanced thermal stability to complexes formed between the oligonucleotide containing BSN and their complementary target strand. In one embodiment, the oligonucleotide inhibitors contain locked nucleotides or LNAs containing the 2'-O, 4'-C-methylene ribonucleoside (structure A) wherein the ribose sugar moiety is in a "locked" conformation. In another embodiment, the oligonucleotide inhibitors contain at least one 2'-C, 4'-C-bridged 2' deoxyribonucleoside (structure B). See, e.g., U.S. Pat. No. 6,403,566 and Wang et al. (1999) Bioorganic and Medicinal Chemistry Letters, Vol. 9: 1147-1150, both of which are herein incorporated by reference in their entireties. In yet another embodiment, the oligonucleotide inhibitors contain at least one modified nucleoside having the structure shown in structure C. The oligonucleotide inhibitors targeting miR-155 can contain combinations of BSN (LNA, 2'-C, 4'-C-bridged 2' deoxyribonucleoside, and the like) or other modified nucleotides, and ribonucleotides or deoxyribonucleotides.

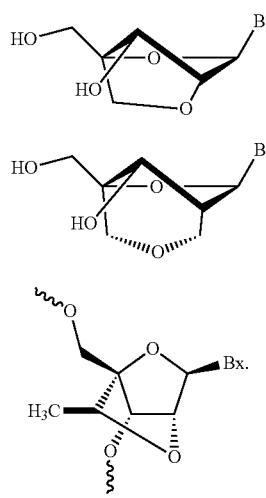

The terms "non-LNA nucleotide", and "non-LNA modification" as used herein refer to a nucleotide different from a LNA nucleotide, i.e. the terms include a DNA nucleotide, an RNA nucleotide as well as a modified nucleotide where a base and/or sugar is modified except that the modification is not a LNA modification.

In some embodiments, the oligonucleotide inhibitor of miR-155 contains at least one nucleotide containing a non-LNA modification. For example, in one embodiment, the oligonucleotide inhibitor of miR-155 contains at least one 2'-C-bridged bicyclic nucleotide (CBBN) as described in U.S. Pre-Grant Publication No. 2016/0010090A1 ("the '090 publication"), which is hereby incorporated by reference herein in its entirety. The '090 publication describes a variety of CBBN modifications such as 2'-CBBN, oxoCBBN, amino CBBN, thioCBBN, etc. All CBBN modifications described in the '090 publications could be used in the oligonucleotide inhibitors of the present invention. In another embodiment, the non-LNA modification present in the oligonucleotide inhibitor of miR-155 could be an ethylene-bridged nucleic acid (ENA) modification. For example, in one embodiment, the oligonucleotide inhibitor of miR-155 contains at least one ethylene-bridged nucleic acid (ENA), also referred to herein as ethylene-bridged nucleotide. Other bridged modifications include 2', 4'-constrained ethyl nucleic acid called S-cEt or cEt and 2'-4'-carbocyclic LNA (carba-LNA).

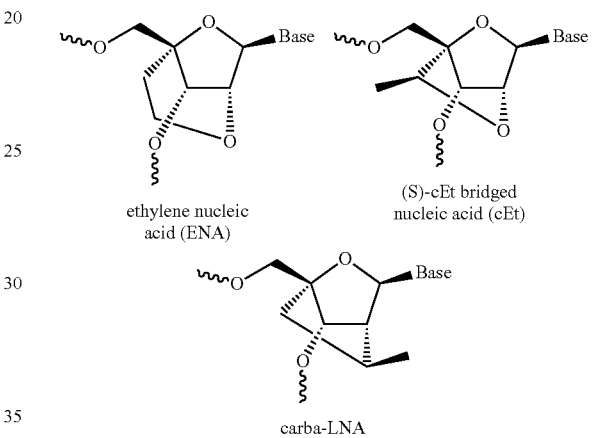

When referring to substituting a DNA or RNA nucleotide by its corresponding locked nucleotide in the context of the present invention, the term "corresponding locked nucleotide" is intended to mean that the DNA/RNA nucleotide has been replaced by a locked nucleotide containing the same naturally-occurring nitrogenous base as the DNA/RNA nucleotide that it has replaced or the same nitrogenous base that is chemically modified. For example, the corresponding locked nucleotide of a DNA nucleotide containing the nitrogenous base C may contain the same nitrogenous base C or the same nitrogenous base C that is chemically modified, such as 5-methylcytosine.

In certain embodiments, the oligonucleotide inhibitor of miR-155 contains at least 5, 6, 7, 8, 9, 10, or 11 locked nucleotides. In one embodiment, the oligonucleotide inhibitor of miR-155 contains at least 7, 8, 9, or 10 locked nucleotides. In one embodiment, at least the first three nucleotides from the 3' end of the oligonucleotide inhibitor are locked nucleotides. In another embodiment, at least the first four nucleotides from the 3' end of the oligonucleotide inhibitor are locked nucleotides. In yet another embodiment, the first nucleotide from the 5' end of the oligonucleotide inhibitor is a locked nucleotide.

In certain embodiments, the oligonucleotide inhibitor contains at least 1, at least 2, at least 3, at least 4, or at least 5 DNA nucleotides. In one embodiment, at least the second nucleotide from the 5' end of the oligonucleotide inhibitor is a DNA nucleotide. In another embodiment, at least the second and fourth nucleotides from the 5' end of the oligonucleotide inhibitor are DNA nucleotides.

Oligonucleotide inhibitors of the present invention may include modified nucleotides that have a base modification or substitution. The natural or unmodified bases in RNA are the purine bases adenine (A) and guanine (G), and the pyrimidine bases cytosine (C) and uracil (U) (DNA has thymine (T)). Modified bases, also referred to as heterocyclic base moieties, include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (including 5-bromo, 5-trifluoromethyl and other 5-substituted uracils and cytosines), 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. In certain embodiments, oligonucleotide inhibitors targeting miR-155 comprise one or more BSN modifications in combination with a base modification (e.g. 5-methylcytosine).

Oligonucleotide inhibitors of the present invention may include nucleotides with modified sugar moieties. Representative modified sugars include carbocyclic or acyclic sugars, sugars having substituent groups at one or more of their 2', 3' or 4' positions and sugars having substituents in place of one or more hydrogen atoms of the sugar. In certain embodiments, the sugar is modified by having a substituent group at the 2' position. In additional embodiments, the sugar is modified by having a substituent group at the 3' position. In other embodiments, the sugar is modified by having a substituent group at the 4' position. It is also contemplated that a sugar may have a modification at more than one of those positions, or that an oligonucleotide inhibitor may have one or more nucleotides with a sugar modification at one position and also one or more nucleotides with a sugar modification at a different position.

Sugar modifications contemplated in the oligonucleotide inhibitors of the present invention include, but are not limited to, a substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted with $C_1$ to $C_{10}$ alkyl or $C_2$ to $C_{10}$ alkenyl and alkynyl. In one embodiment, the modification includes 2'-methoxyethoxy (2'-O—$CH_2CH_2OCH_3$, which is also known as 2'-O-(2-methoxyethyl) or 2'-MOE), that is, an alkoxyalkoxy group. Another modification includes 2'-dimethylaminooxyethoxy, that is, a O($CH_2$)$_2$ON($CH_3$)$_2$ group, also known as 2'-DMAOE and 2'-dimethylaminoethoxyethoxy (also known in the art as 2'-O-dimethylamino-ethoxy-ethyl or 2'-DMAEOE), that is, 2'-O—$CH_2$—O—$CH_2$—N($CH_3$)$_2$.

Additional sugar substituent groups include allyl (—$CH_2$—CH=$CH_2$), —O-allyl, methoxy (—O—$CH_3$), aminopropoxy (—O$CH_2CH_2CH_2NH_2$), and fluoro (F). Sugar substituent groups on the 2' position (2'-) may be in the arabino (up) position or ribo (down) position. One 2'-arabino modification is 2'-F. Other similar modifications may also be made at other positions on the sugar moiety, particularly the 3' position of the sugar on the 3' terminal nucleoside or in 2'-5' linked oligonucleotides and the 5' position of 5' terminal nucleotide. In certain embodiments, the sugar modification is a 2'-O-alkyl (e.g. 2'-O-methyl, 2'-O-methoxyethyl), 2'-halo (e.g., 2'-fluoro, 2'-chloro, 2'-bromo), and 4' thio modifications.

Other modifications of oligonucleotide inhibitors to enhance stability and improve efficacy, such as those described in U.S. Pat. No. 6,838,283, which is herein incorporated by reference in its entirety, are known in the art and are suitable for use in the methods of the invention. For instance, to facilitate in vivo delivery and stability, the oligonucleotide inhibitor can be linked to a steroid, such as cholesterol moiety, a vitamin, a fatty acid, a carbohydrate or glycoside, a peptide, or other small molecule ligand at its 3' end.

In some embodiments, the oligonucleotide inhibitors of the present invention may be conjugated to a carrier molecule such as a steroid (cholesterol). The carrier molecule is attached to the 3' or 5' end of the oligonucleotide inhibitor either directly or through a linker or a spacer group. In various embodiments, the carrier molecule is cholesterol, a cholesterol derivative, cholic acid or a cholic acid derivative. The use of carrier molecules disclosed in U.S. Pat. No. 7,202,227, which is incorporated by reference herein in its entirety, is also envisioned. In certain embodiments, the carrier molecule is cholesterol and it is attached to the 3' or 5' end of the oligonucleotide inhibitor through at least a six carbon linker. In some embodiments, the carrier molecule is attached to the 3' or 5' end of the oligonucleotide inhibitor through a six or nine carbon linker. In some embodiments, the linker is a cleavable linker. In various embodiments, the linker comprises a substantially linear hydrocarbon moiety. The hydrocarbon moiety may comprise from about 3 to about 15 carbon atoms and may be conjugated to cholesterol through a relatively non-polar group such as an ether or a thioether linkage. In certain embodiments, the hydrocarbon linker/spacer comprises an optionally substituted C2 to C15 saturated or unsaturated hydrocarbon chain (e.g. alkylene or alkenylene). A variety of linker/spacer groups described in U.S. Pre-grant Publication No. 2012/0128761, which is incorporated by reference herein in its entirety, can be used in the present invention.

In one embodiment, the oligonucleotide inhibitor of miR-155 comprises a sequence of 11 to 16 nucleotides, wherein the oligonucleotide inhibitor is fully complementary to a mature sequence of miR-155 and has a full phosphorothioate backbone; and wherein at least the first three nucleotides from the 3' end of the oligonucleotide inhibitor are locked nucleotides and at least the second nucleotide from the 5' end of the oligonucleotide inhibitor is a deoxyribonucleic acid (DNA) nucleotide. In some of these embodiments, the fourth nucleotide from the 3' end of the oligonucleotide inhibitor is also a locked nucleotide. In some of these embodiments, at least the second and fourth nucleotides from the 5' end of the oligonucleotide inhibitor are DNA nucleotides. In certain embodiments, the oligonucleotide inhibitor of miR-155 has a length of 12 or 14 nucleotides. In some embodiments, the oligonucleotide inhibitor contains at least 5, 6, 7, 8, 9, or 10 locked nucleotides. In further embodiments, at least the sixth and/or the eighth nucleotide from the 5' end of the oligonucleotide inhibitor is a DNA nucleotide. In yet further embodiments, the oligonucleotide inhibitor comprises DNA nucleotides at the second, sixth, and the eighth position from the 5' end.

In another embodiment, the oligonucleotide inhibitor of miR-155 comprises a sequence of 11 to 14 nucleotides, wherein the oligonucleotide inhibitor is fully complementary to a mature sequence of miR-155 and has a full phosphorothioate backbone; and wherein at least the first three nucleotides from the 3' end of said oligonucleotide inhibitor are modified nucleotides and at least the second nucleotide from the 5' end of the oligonucleotide inhibitor is a modified or an unmodified deoxyribonucleic acid (DNA) nucleotide.

In yet another embodiment, the oligonucleotide inhibitor of miR-155 comprises a sequence of 11 to 14 nucleotides, wherein the oligonucleotide inhibitor is fully complementary to a mature sequence of miR-155 and has a full phosphorothioate backbone; wherein at least 7 nucleotides of said oligonucleotide inhibitor are modified nucleotides and at least the second nucleotide from the 5' end of the oligonucleotide inhibitor is a modified or an unmodified deoxyribonucleic acid (DNA) nucleotide.

In yet another embodiment, the oligonucleotide inhibitor of miR-155 comprises a sequence of 11 to 14 nucleotides, wherein the oligonucleotide inhibitor is fully complementary to a mature sequence of miR-155 and has a full phosphorothioate backbone; and wherein at least the first three nucleotides from 3' end of said oligonucleotide inhibitor are modified nucleotides and at least the fourth and fifth nucleotides from the 5' end of the oligonucleotide inhibitor are modified or unmodified deoxyribonucleic acid (DNA) nucleotides. In some of these embodiments, the fourth and/or the fifth DNA nucleotide from the 5' end of the oligonucleotide inhibitor are unmodified DNA nucleotides.

In some embodiments where the oligonucleotide inhibitor is 11 to 14 nucleotides long, said inhibitor contains at least 5, 6, 7, 8, 9, or 10 modified nucleotides. In some of these embodiments, the oligonucleotide inhibitor contains 7, 8, 9, or 10 modified nucleotides. In some embodiments where the oligonucleotide inhibitor is 11 to 14 nucleotides long, at least the first three nucleotides from the 3' end of said oligonucleotide inhibitor are modified nucleotides. In some embodiments, all modified nucleotides are locked nucleotides. In some embodiments, the 5, 6, 7, 8, 9, or 10 modified nucleotides present in the oligonucleotide inhibitors are a combination of locked nucleotides and nucleotides containing non-LNA modifications such as ethylene-bridged nucleotides, 2'-C-bridged bicyclic nucleotides, 2'-substituted nucleotides, and other sugar and/or base modifications described herein.

In some embodiments, the second nucleotide from the 5' end of the oligonucleotide inhibitor is an unmodified deoxyribonucleic acid (DNA) nucleotide.

In one embodiment, the oligonucleotide inhibitor of miR-155 comprises a sequence of SEQ ID NO: 25. In another embodiment, the oligonucleotide inhibitor of miR-155 comprises a sequence of SEQ ID NO: 22. In yet another embodiment, the oligonucleotide inhibitor of miR-155 comprises a sequence of SEQ ID NO: 23.

In some other embodiments, the oligonucleotide inhibitor of miR-155 comprises a sequence selected from the group consisting of SEQ ID NOs: 33, 39, 43, 44, 47, 58, 84, 99, 111, 115, and 120.

In various embodiments, the oligonucleotide inhibitor of miR-155-5p has a sequence selected from Table 1.

TABLE 1

| SEQ ID NO. | Sequence (5'-3') with modifications[1] |
|---|---|
| SEQ ID NO: 3 | 5'-lAs.dTs.dCs.dAs.lCs.lGs.dAs.lTs.dTs.lAs.lGs.dCs.lAs.dTs.lTs.lA-3' |
| SEQ ID NO: 4 | 5'-lAs.dTs.dCs.dAs.lCs.lGs.dAs.dTs.lTs.lAs.lGs.dCs.lAs.dTs.lTs.lA-3' |
| SEQ ID NO: 5 | 5'-lAs.lTs.dCs.dAs.dCs.lGs.dAs.lTs.dTs.lAs.lGs.dCs.lAs.dTs.lTs.lA-3' |
| SEQ ID NO: 6 | 5'-lAs.lTs.dCs.dAs.dCs.lGs.lAs.dTs.dTs.lAs.lGs.lCs.dAs.lTs.dTs.lA-3' |
| SEQ ID NO: 7 | 5'-lAs.dTs.dCs.dAs.lCs.lGs.dAs.lTs.dTs.lAs.lGs.dCs.lAs.lTs.dTs.lA-3' |
| SEQ ID NO: 8 | 5'-lAs.lTs.dCs.dAs.lCs.dGs.dAs.dTs.lTs.lAs.dGs.lCs.lAs.dTs.lTs.lA-3' |
| SEQ ID NO: 9 | 5'-lAs.dTs.dCs.dAs.lCs.dGs.lAs.dTs.lTs.lAs.dGs.lCs.lAs.dTs.lTs.lA-3' |
| SEQ ID NO: 10 | 5'-lAs.dTs.dCs.lAs.dCs.dGs.lAs.lTs.dTs.lAs.lGs.dCs.lAs.dTs.lTs.lA-3' |
| SEQ ID NO: 11 | 5'-lAs.dTs.lCs.dAs.dCs.lGs.dAs.lTs.lTs.dAs.dGs.lCs.lAs.dTs.lTs.lA-3' |
| SEQ ID NO: 12 | 5'-lAs.lTs.dCs.lAs.lCs.dGs.dAs.dTs.lTs.lAs.dGs.lCs.lAs.dTs.dTs.lA-3' |
| SEQ ID NO: 13 | 5'-lAs.dTs.lCs.dAs.dCs.dGs.lAs.dTs.lTs.lAs.dGs.lCs.lAs.dTs.lTs.lA-3' |
| SEQ ID NO: 14 | 5'-lAs.dTs.lCs.dAs.lCs.dGs.lAs.dTs.lTs.dAs.lGs.dCs.lAs.dTs.lTs.lA-3' |
| SEQ ID NO: 15 | 5'-lTs.dCs.dAs.lCs.dGs.dAs.lTs.dTs.dAs.lGs.dCs.lAs.lTs.dTs.lA-3' |
| SEQ ID NO: 16 | 5'-lTs.dCs.lAs.dCs.dGs.lAs.lTs.dTs.dAs.lGs.dCs.lAs.dTs.lTs.lA-3' |
| SEQ ID NO: 17 | 5'-lTs.dCs.dAs.dCs.lGs.lAs.lTs.dTs.dAs.lGs.dCs.lAs.dTs.lTs.lA-3' |
| SEQ ID NO: 18 | 5'-lTs.lCs.lAs.dCs.lGs.dAs.dTs.lTs.lAs.dGs.lCs.dAs.dTs.lTs.lA-3' |
| SEQ ID NO: 19 | 5'-lTs.dCs.dAs.lCs.dGs.dAs.dTs.lTs.lAs.lGs.lCs.lAs.lTs.lTs.lA-3' |
| SEQ ID NO: 20 | 5'-lTs.dCs.lAs.dCs.lGs.lAs.lTs.dTs.dAs.lGs.lCs.lAs.dTs.lTs.lA-3' |
| SEQ ID NO: 21 | 5'-lGs.lAs.lTs.lTs.lAs.lGs.dCs.lAs.lTs.dTs.lA-3' |
| SEQ ID NO: 22 | 5'-lCs.dGs.lAs.lTs.lTs.lAs.lGs.dCs.lAs.lTs.lTs.lA-3' |
| SEQ ID NO: 23 | 5'-lCs.dGs.lAs.lTs.lTs.dAs.lGs.dCs.lAs.lTs.lTs.lA-3' |

TABLE 1-continued

| SEQ ID NO. | Sequence (5'-3') with modifications[1] |
|---|---|
| SEQ ID NO: 24 | 5'-lCs.lAs.dCs.lGs.dAs.lTs.lTs.dAs.lGs.dCs.lAs.lTs.lTs.lA-3' |
| SEQ ID NO: 25 | 5'-lCs.dAs.lCs.dGs.dAs.lTs.lTs.dAs.lGs.dCs.lAs.lTs.lTs.lA-3' |
| SEQ ID NO: 26 | 5'-lTs.dCs.lAs.mdCs.lGs.lAs.lTs.dTs.dAs.lGs.lCs.lAs.dTs.lTs.lA-3' |
| SEQ ID NO: 27 | 5'-lTs.lAs.lGs.lCs.lAs.lTs.lTs.lA-3' |
| SEQ ID NO: 29 | 5'-lCs.dAs.lCs.dGs.lAs.lTs.lTs.dAs.lGs.dCs.lAs.lTs.lTs.lA-3' |
| SEQ ID NO: 30 | 5'-lCs.dAs.lCs.dGs.lAs.dTs.lTs.dAs.lGs.dCs.lAs.lTs.lTs.lA-3' |
| SEQ ID NO: 31 | 5'-lCs.dAs.lCs.dGs.dAs.lTs.lTs.lAs.lGs.dCs.lAs.dTs.lTs.lA-3' |
| SEQ ID NO: 32 | 5'-dCs.dAs.lCs.dGs.dAs.lTs.lTs.dAs.lGs.dCs.lAs.lTs.lTs.lA-3' |
| SEQ ID NO: 33 | 5'-lCs.lAs.lCs.dGs.dAs.lTs.lTs.dAs.lGs.dCs.lAs.lTs.lTs.lA-3' |
| SEQ ID NO: 34 | 5'-lCs.dAs.dCs.dGs.dAs.lTs.lTs.dAs.lGs.dCs.lAs.lTs.lTs.lA-3' |
| SEQ ID NO: 35 | 5'-lCs.dAs.lCs.lGs.dAs.lTs.lTs.dAs.lGs.dCs.lAs.lTs.lTs.lA-3' |
| SEQ ID NO: 36 | 5'-lCs.dAs.lCs.dGs.lAs.lTs.lTs.dAs.lGs.dCs.lAs.lTs.lTs.lA-3' |
| SEQ ID NO: 37 | 5'-lCs.dAs.lCs.dGs.dAs.dTs.lTs.dAs.lGs.dCs.lAs.lTs.lTs.lA-3' |
| SEQ ID NO: 38 | 5'-lCs.dAs.lCs.dGs.dAs.lTs.dTs.dAs.lGs.dCs.lAs.lTs.lTs.lA-3' |
| SEQ ID NO: 39 | 5'-lCs.dAs.lCs.dGs.dAs.lTs.lTs.lAs.lGs.dCs.lAs.lTs.lTs.lA-3' |
| SEQ ID NO: 40 | 5'-lCs.dAs.lCs.dGs.dAs.lTs.lTs.dAs.dGs.dCs.lAs.lTs.lTs.lA-3' |
| SEQ ID NO: 41 | 5'-lCs.dAs.lCs.dGs.dAs.lTs.lTs.dAs.lGs.lCs.lAs.lTs.lTs.lA-3' |
| SEQ ID NO: 42 | 5'-lCs.dAs.lCs.dGs.dAs.lTs.lTs.dAs.lGs.dCs.dAs.lTs.lTs.lA-3' |
| SEQ ID NO: 43 | 5'-lCs.dAs.lCs.dGs.dAs.lTs.lTs.dAs.lGs.dCs.lAs.dTs.lTs.lA-3' |
| SEQ ID NO: 44 | 5'-lCs.dAs.lCs.dGs.dAs.lTs.lTs.dAs.lGs.dCs.lAs.lTs.dTs.lA-3' |
| SEQ ID NO: 45 | 5'-lCs.dAs.lCs.dGs.dAs.lTs.lTs.dAs.lGs.dCs.lAs.lTs.lTs.dA-3' |
| SEQ ID NO: 46 | 5'-dCs.lAs.lCs.dGs.dAs.lTs.lTs.dAs.lGs.dCs.lAs.lTs.lTs.lA-3' |
| SEQ ID NO: 47 | 5'-lCs.lAs.dCs.dGs.dAs.lTs.lTs.dAs.lGs.dCs.lAs.lTs.lTs.lA-3' |
| SEQ ID NO: 48 | 5'-lCs.dAs.dCs.lGs.dAs.lTs.lTs.dAs.lGs.dCs.lAs.lTs.lTs.lA-3' |
| SEQ ID NO: 49 | 5'-lCs.dAs.lCs.dGs.lAs.dTs.lTs.dAs.lGs.dCs.lAs.lTs.lTs.lA-3' |
| SEQ ID NO: 50 | 5'-lCs.dAs.lCs.dGs.dAs.lTs.dTs.lAs.lGs.dCs.lAs.lTs.lTs.lA-3' |
| SEQ ID NO: 51 | 5'-lCs.dAs.lCs.dGs.dAs.lTs.lTs.lAs.dGs.dCs.lAs.lTs.lTs.lA-3' |
| SEQ ID NO: 52 | 5'-lCs.dAs.lCs.dGs.dAs.lTs.lTs.dAs.dGs.lCs.lAs.lTs.lTs.lA-3' |
| SEQ ID NO: 53 | 5'-lCs.dAs.lCs.dGs.dAs.lTs.lTs.dAs.lGs.lCs.dAs.lTs.lTs.lA-3' |
| SEQ ID NO: 54 | 5'-lAs.lCs.dGs.dAs.lTs.lTs.dAs.lGs.dCs.lAs.lTs.lTs.lA-3' |
| SEQ ID NO: 55 | 5'-lCs.dGs.dAs.lTs.lTs.dAs.lGs.dCs.lAs.lTs.lTs.lA-3' |
| SEQ ID NO: 56 | 5'-lGs.dAs.lTs.lTs.dAs.lGs.dCs.lAs.lTs.lTs.lA-3' |
| SEQ ID NO: 57 | 5'-dAs.lCs.dGs.dAs.lTs.lTs.dAs.lGs.dCs.lAs.lTs.lTs.lA-3' |
| SEQ ID NO: 58 | 5'-lAs.dCs.dGs.dAs.lTs.lTs.dAs.lGs.dCs.lAs.lTs.lTs.lA-3' |
| SEQ ID NO: 59 | 5'-lAs.lCs.lGs.dAs.lTs.lTs.dAs.lGs.dCs.lAs.lTs.lTs.lA-3' |
| SEQ ID NO: 60 | 5'-lAs.lCs.dGs.lAs.lTs.lTs.dAs.lGs.dCs.lAs.lTs.lTs.lA-3' |
| SEQ ID NO: 61 | 5'-lAs.lCs.dGs.dAs.dTs.lTs.dAs.lGs.dCs.lAs.lTs.lTs.lA-3' |
| SEQ ID NO: 62 | 5'-lAs.lCs.dGs.dAs.lTs.dTs.dAs.lGs.dCs.lAs.lTs.lTs.lA-3' |
| SEQ ID NO: 63 | 5'-lAs.lCs.dGs.dAs.lTs.lTs.lAs.lGs.dCs.lAs.lTs.lTs.lA-3' |

TABLE 1-continued

| SEQ ID NO. | Sequence (5'-3') with modifications[1] |
|---|---|
| SEQ ID NO: 64 | 5'-lAs.lCs.dGs.dAs.lTs.lTs.dAs.dGs.dCs.lAs.lTs.lTs.lA-3' |
| SEQ ID NO: 65 | 5'-lAs.lCs.dGs.dAs.lTs.lTs.dAs.lGs.lCs.lAs.lTs.lTs.lA-3' |
| SEQ ID NO: 66 | 5'-lAs.lCs.dGs.dAs.lTs.lTs.dAs.lGs.dCs.dAs.lTs.lTs.lA-3' |
| SEQ ID NO: 67 | 5'-lAs.lCs.dGs.dAs.lTs.lTs.dAs.lGs.dCs.lAs.dTs.lTs.lA-3' |
| SEQ ID NO: 68 | 5'-lAs.lCs.dGs.dAs.lTs.lTs.dAs.lGs.dCs.lAs.lTs.dTs.lA-3' |
| SEQ ID NO: 69 | 5'-lAs.lCs.dGs.dAs.lTs.lTs.dAs.lGs.dCs.lAs.lTs.lTs.dA-3' |
| SEQ ID NO: 70 | 5'-lAs.dCs.lGs.dAs.lTs.lTs.dAs.lGs.dCs.lAs.lTs.lTs.lA-3' |
| SEQ ID NO: 71 | 5'-lAs.lCs.dGs.lAs.dTs.lTs.dAs.lGs.dCs.lAs.lTs.lTs.lA-3' |
| SEQ ID NO: 72 | 5'-lAs.lCs.dGs.dAs.lTs.lTs.dAs.lGs.dCs.lAs.lTs.lTs.lA-3' |
| SEQ ID NO: 73 | 5'-lAs.lCs.dGs.dAs.lTs.dTs.lAs.lGs.dCs.lAs.lTs.lTs.lA-3' |
| SEQ ID NO: 74 | 5'-lAs.lCs.dGs.dAs.lTs.lTs.lAs.dGs.dCs.lAs.lTs.lTs.lA-3' |
| SEQ ID NO: 75 | 5'-lAs.lCs.dGs.dAs.lTs.lTs.dAs.dGs.lCs.lAs.lTs.lTs.lA-3' |
| SEQ ID NO: 76 | 5'-lAs.lCs.dGs.dAs.lTs.lTs.dAs.lGs.lCs.dAs.lTs.lTs.lA-3' |
| SEQ ID NO: 77 | 5'-dCs.dGs.dAs.lTs.lTs.dAs.lGs.dCs.lAs.lTs.lTs.lA-3' |
| SEQ ID NO: 78 | 5'-lCs.lGs.dAs.lTs.lTs.dAs.lGs.dCs.lAs.lTs.lTs.lA-3' |
| SEQ ID NO: 79 | 5'-lCs.dGs.lAs.lTs.lTs.dAs.lGs.dCs.lAs.lTs.lTs.lA-3' |
| SEQ ID NO: 80 | 5'-lCs.dGs.dAs.dTs.lTs.dAs.lGs.dCs.lAs.lTs.lTs.lA-3' |
| SEQ ID NO: 81 | 5'-lCs.dGs.dAs.lTs.dTs.dAs.lGs.dCs.lAs.lTs.lTs.lA-3' |
| SEQ ID NO: 82 | 5'-lCs.dGs.dAs.lTs.lTs.lAs.lGs.dCs.lAs.lTs.lTs.lA-3' |
| SEQ ID NO: 83 | 5'-lCs.dGs.dAs.lTs.lTs.dAs.dGs.dCs.lAs.lTs.lTs.lA-3' |
| SEQ ID NO: 84 | 5'-lCs.dGs.dAs.lTs.lTs.dAs.lGs.lCs.lAs.lTs.lTs.lA-3' |
| SEQ ID NO: 85 | 5'-lCs.dGs.dAs.lTs.lTs.dAs.lGs.dCs.dAs.lTs.lTs.lA-3' |
| SEQ ID NO: 86 | 5'-lCs.dGs.dAs.lTs.lTs.dAs.lGs.dCs.lAs.dTs.lTs.lA-3' |
| SEQ ID NO: 87 | 5'-lCs.dGs.dAs.lTs.lTs.dAs.lGs.dCs.lAs.lTs.dTs.lA-3' |
| SEQ ID NO: 88 | 5'-lCs.dGs.dAs.lTs.lTs.dAs.lGs.dCs.lAs.lTs.lTs.dA-3' |
| SEQ ID NO: 89 | 5'-dCs.lGs.dAs.lTs.lTs.dAs.lGs.dCs.lAs.lTs.lTs.lA-3' |
| SEQ ID NO: 90 | 5'-lCs.dGs.lAs.dTs.lTs.dAs.lGs.dCs.lAs.lTs.lTs.lA-3' |
| SEQ ID NO: 91 | 5'-lCs.dGs.dAs.lTs.dTs.lAs.lGs.dCs.lAs.lTs.lTs.lA-3' |
| SEQ ID NO: 92 | 5'-lCs.dGs.dAs.lTs.lTs.lAs.dGs.dCs.lAs.lTs.lTs.lA-3' |
| SEQ ID NO: 93 | 5'-lCs.dGs.dAs.lTs.lTs.dAs.dGs.lCs.lAs.lTs.lTs.lA-3' |
| SEQ ID NO: 94 | 5'-lCs.dGs.dAs.lTs.lTs.dAs.lGs.lCs.dAs.lTs.lTs.lA-3' |
| SEQ ID NO: 95 | 5'-dGs.dAs.lTs.lTs.dAs.lGs.dCs.lAs.lTs.lTs.lA-3' |
| SEQ ID NO: 96 | 5'-lGs.lAs.lTs.lTs.dAs.lGs.dCs.lAs.lTs.lTs.lA-3' |
| SEQ ID NO: 97 | 5'-lGs.dAs.dTs.lTs.dAs.lGs.dCs.lAs.lTs.lTs.lA-3' |
| SEQ ID NO: 98 | 5'-lGs.dAs.lTs.dTs.dAs.lGs.dCs.lAs.lTs.lTs.lA-3' |
| SEQ ID NO: 99 | 5'-lGs.dAs.lTs.lTs.lAs.lGs.dCs.lAs.lTs.lTs.lA-3' |
| SEQ ID NO: 100 | 5'-lGs.dAs.lTs.lTs.dAs.dGs.dCs.lAs.lTs.lTs.lA-3' |
| SEQ ID NO: 101 | 5'-lGs.dAs.lTs.lTs.dAs.lGs.lCs.lAs.lTs.lTs.lA-3' |
| SEQ ID NO: 102 | 5'-lGs.dAs.lTs.lTs.dAs.lGs.dCs.dAs.lTs.lTs.lA-3' |

TABLE 1-continued

| SEQ ID NO. | Sequence (5'-3') with modifications[1] |
|---|---|
| SEQ ID NO: 103 | 5'-lGs.dAs.lTs.lTs.dAs.lGs.dCs.lAs.dTs.lTs.lA-3' |
| SEQ ID NO: 104 | 5'-lGs.dAs.lTs.lTs.dAs.lGs.dCs.lAs.lTs.dTs.lA-3' |
| SEQ ID NO: 105 | 5'-lGs.dAs.lTs.lTs.dAs.lGs.dCs.lAs.lTs.lTs.dA-3' |
| SEQ ID NO: 106 | 5'-dGs.lAs.lTs.lTs.dAs.lGs.dCs.lAs.lTs.lTs.lA-3' |
| SEQ ID NO: 107 | 5'-lGs.lAs.dTs.lTs.dAs.lGs.dCs.lAs.lTs.lTs.lA-3' |
| SEQ ID NO: 108 | 5'-lGs.dAs.lTs.dTs.lAs.lGs.dCs.lAs.lTs.lTs.lA-3' |
| SEQ ID NO: 109 | 5'-lGs.dAs.lTs.lTs.lAs.dGs.dCs.lAs.lTs.lTs.lA-3' |
| SEQ ID NO: 110 | 5'-lGs.dAs.lTs.lTs.dAs.dGs.lCs.lAs.lTs.lTs.lA-3' |
| SEQ ID NO: 111 | 5'-lGs.dAs.lTs.lTs.dAs.lGs.lCs.dAs.lTs.lTs.lA-3' |
| SEQ ID NO: 112 | 5'-eCs.dAs.eCs.dGs.dAs.eTs.eTs.dAs.eGs.dCs.eAs.eTs.eTs.eA-3' |
| SEQ ID NO: 113 | 5'-lCs.dAs.lCs.dGs.dAs.lTs.lTs.dAs.lGs.dCs.eAs.lTs.lTs.eA-3' |
| SEQ ID NO: 114 | 5'-eCs.dAs.eCs.dGs.dAs.lTs.lTs.dAs.lGs.dCs.lAs.lTs.lTs.lA-3' |
| SEQ ID NO: 115 | 5'-lCs.dAs.lCs.dGs.dAs.lTs.lTs.dAs.eGs.dCs.lAs.lTs.lTs.lA-3' |
| SEQ ID NO: 116 | 5'-lCs.dAs.lCs.dGs.dAs.eTs.eTs.dAs.lGs.dCs.lAs.eTs.eTs.lA-3' |
| SEQ ID NO: 117 | 5'-lCs.dAs.lCs.dGs.dAs.lTs.eTs.dAs.lGs.dCs.lAs.lTs.lTs.lA-3' |
| SEQ ID NO: 118 | 5'-lCs.dAs.lCs.dGs.dAs.lTs.lTs.dAs.lGs.dCs.lAs.lTs.eTs.lA-3' |
| SEQ ID NO: 119 | 5'-lCs.dAs.lCs.dGs.dAs.lTs.lTs.dAs.lGs.dCs.abAs.lTs.lTs.abA-3' |
| SEQ ID NO: 120 | 5'-abCs.dAs.abCs.dGs.dAs.abTs.abTs.dAs.abGs.dCs.abAs.abTs.abTs.abA-3' |

[1] l = locked nucleic acid modification; d = deoxyribonucleotide; s = phosphorothioate linkage; md = 5-Methylcytosine; e = ethylene-bridged nucleotide (ENA); ab = amino-2'-C-Bridged Bicyclic Nucleotide (CBBN).

Administration of an oligonucleotide inhibitor of the present invention to a subject reduces or inhibits the activity or function of miR-155 in cells of the subject. In one embodiment, the oligonucleotide inhibitor inhibits the activity or function of miR-155 in cancer cells, cells of the immune system including B and T lymphocytes, monocytes, macrophages, microglia, NK cells, and inflammatory cells. In one embodiment, the cancer cells are malignant T cells. Malignant T cells that can be treated with oligonucleotide inhibitors of the invention include cutaneous T cell lymphoma (CTCL) cells, CD4+ T cells, CD8+ T cells, αβ T cells, γδ T cells and memory T cells. In one embodiment, the malignant T cells are cutaneous T cell lymphoma (CTCL) cells.

In some embodiments, certain oligonucleotide inhibitors of the present invention may show a greater inhibition of the activity or function of miR-155 in cancer cells, such as malignant T cells, compared to other miR-155 inhibitors. The term "other miR-155 inhibitors" includes nucleic acid inhibitors such as antisense oligonucleotides, antimiRs, antagomiRs, mixmers, gapmers, aptamers, ribozymes, small interfering RNAs, or small hairpin RNAs; antibodies or antigen binding fragments thereof; and/or drugs, which inhibit the activity or function of miR-155. It is possible that a particular oligonucleotide inhibitor of the present invention may show a greater inhibition of miR-155 in cancer cells, such as malignant T cells, compared to other oligonucleotide inhibitors of the present invention. The term "greater" as used herein refers to quantitatively more or statistically significantly more.

Administration of an oligonucleotide inhibitor of the present invention up-regulates the expression or activity of miR-155 target genes in cells of the subject. Target genes for miR-155 include, but are not limited to, INPP50/SHIP1, Jarid2, Picalm, Bach1, Wee1, CUX1, Cebpb, SPIB/PU.1, and IL7R. In one embodiment, oligonucleotide inhibitors of the present invention up-regulate the expression or activity of at least four target genes of miR-155 in cancer cells, cells of the immune system including B and T lymphocytes, monocytes, macrophages, microglia, NK cells, and inflammatory cells. In some embodiments, four target genes up-regulated by oligonucleotide inhibitors of the present invention include Bach1, Jarid2, Picalm, and SHIP1. The invention encompasses using the changes in the expression of these four genes (gene expression signature) as means to determine the activity of miR-155 inhibitors. In some embodiments, there is about 1.25-fold, 1.5-fold, 2-fold, 3-fold, 4-fold, 5-fold, 6-fold, 7-fold, or 8-fold, including values therebetween, change in the expression or activity of miR-155 target genes upon administration of oligonucleotide inhibitors of the present invention. In one embodiment, there is at least about 2-fold, 3-fold, 4-fold, or 5-fold, including values therebetween, change in the expression or activity of miR-155 target genes upon administration of oligonucleotide inhibitors of the present invention.

In one embodiment, the oligonucleotide inhibitor of the present invention shows a greater up-regulation of miR-155 target genes in cancer cells, such as malignant T cells, compared to other miR-155 inhibitors. In certain embodiments, the oligonucleotide inhibitors of the present invention show a greater up-regulation of at least four target genes of miR-155 in cancer cells compared to other miR-155 inhibitors. In one embodiment, the oligonucleotide inhibitors of the present invention show a greater up-regulation of the expression or activity of four genes, namely, Bach1, Jarid2, Picalm, and SHIP1, in cancer cells compared to other miR-155 inhibitors. In various embodiments, "greater up-regulation" includes about 2-fold, 3-fold, 4-fold, or 5-fold, including values therebetween, increase in the expression or activity of miR-155 target genes compared to other miR-155 inhibitors.

In some embodiments, oligonucleotide inhibitors of the present invention reduce or inhibit proliferation of cancer cells and/or induce apoptosis of cancer cells, such as malignant T cells including cutaneous T cell lymphoma (CTCL) cells. Administration of oligonucleotide inhibitors of the present invention may provide up to about 5%, 10%, 15%, 20%, 25%, 30%, 35%, 40%, 45%, 50%, 55%, 60%, 65%, 70%, 80%, 90% or 100%, including values therebetween, reduction in the number of cancer cells. In some embodiments, oligonucleotide inhibitors of the present invention may provide at least about 5%, 10%, 15%, 20%, 25%, 30%, 35%, 40%, 45%, or 50%, including values therebetween, reduction in the number of cancer cells.

In some embodiments, oligonucleotide inhibitors of the present invention may show a greater inhibition of proliferation of cancer cells and/or a greater induction in apoptosis of cancer cells compared to other miR-155 inhibitors. For example, an oligonucleotide inhibitor of the present invention may show up to about 10%, 15%, 20%, 25%, 30%, 35%, or 40%, including values therebetween, more reduction in the number of cancer cells compared to other miR-155 inhibitors.

The present invention provides methods for treating cancer in a subject in need thereof, comprising administering to the subject an oligonucleotide inhibitor of miR-155 according to the invention. The activity or function of miR-155 is reduced in cancer cells of the subject following administration of the oligonucleotide inhibitor.

In one embodiment, the method for treating cancer comprises administering an oligonucleotide inhibitor of miR-155 that has a sequence of 11 to 16 nucleotides, wherein the oligonucleotide inhibitor is fully complementary to a mature sequence of miR-155 and has a full phosphorothioate backbone; and wherein at least the first three nucleotides from the 3' end of said oligonucleotide inhibitor are locked nucleotides and at least the second nucleotide from the 5' end of the oligonucleotide inhibitor is a deoxyribonucleic acid (DNA) nucleotide.

In another embodiment, the method for treating cancer comprises administering an oligonucleotide inhibitor of miR-155 that has a sequence of 11 to 14 nucleotides, wherein the oligonucleotide inhibitor is fully complementary to a mature sequence of miR-155 and has a full phosphorothioate backbone; and wherein at least the first three nucleotides from the 3' end of said oligonucleotide inhibitor are modified nucleotides and at least the second nucleotide from the 5' end of the oligonucleotide inhibitor is a deoxyribonucleic acid (DNA) nucleotide.

In another embodiment, the method for treating cancer comprises administering an oligonucleotide inhibitor of miR-155 that has a sequence of 11 to 14 nucleotides, wherein the oligonucleotide inhibitor is fully complementary to a mature sequence of miR-155 and has a full phosphorothioate backbone; and wherein at least 7 nucleotides of said oligonucleotide inhibitor are modified nucleotides and at least the second nucleotide from the 5' end of the oligonucleotide inhibitor is a deoxyribonucleic acid (DNA) nucleotide.

In yet another embodiment, the method for treating cancer comprises administering an oligonucleotide inhibitor of miR-155 that has a sequence of 11 to 14 nucleotides, wherein the oligonucleotide inhibitor is fully complementary to a mature sequence of miR-155 and has a full phosphorothioate backbone; and wherein at least the first three nucleotides from 3' end of said oligonucleotide inhibitor are modified nucleotides and at least the fourth and fifth nucleotides from the 5' end of the oligonucleotide inhibitor are deoxyribonucleic acid (DNA) nucleotides.

Cancers that can be treated according to the invention include lymphomas including a T cell lymphoma, such as cutaneous T cell lymphoma (CTCL), and a B cell lymphoma and a skin cancer. In certain embodiments, the method for treating cancer comprises administering an oligonucleotide inhibitor of miR-155 selected from the group consisting of SEQ ID NO: 22, SEQ ID NO: 23, and SEQ ID NO: 25. In some other embodiments, the method for treating cancer comprises administering an oligonucleotide inhibitor of miR-155 selected from the group consisting of SEQ ID NOs: 33, 39, 43, 44, 47, 58, 84, 99, 111, 115, and 120.

In one embodiment, the invention provides methods for treating the mycosis fungoides (MF) form of CTCL by administering to the subject an oligonucleotide inhibitor of miR-155 according to the invention. In one embodiment, the method for treating the MF form of CTCL comprises administering an oligonucleotide inhibitor of miR-155 that has a sequence of 11 to 16 nucleotides, wherein the oligonucleotide inhibitor is fully complementary to a mature sequence of miR-155 and has a full phosphorothioate backbone; and wherein at least the first three nucleotides from the 3' end of said oligonucleotide inhibitor are locked nucleotides and at least the second nucleotide from the 5' end of the oligonucleotide inhibitor is a deoxyribonucleic acid (DNA) nucleotide.

In another embodiment, the invention provides methods for treating the mycosis fungoides (MF) form of CTCL comprising administering an oligonucleotide inhibitor of miR-155 that has a sequence of 11 to 14 nucleotides, wherein the oligonucleotide inhibitor is fully complementary to a mature sequence of miR-155 and has a full phosphorothioate backbone; and wherein at least the first three nucleotides from the 3' end of said oligonucleotide inhibitor are modified nucleotides and at least the second nucleotide from the 5' end of the oligonucleotide inhibitor is a deoxyribonucleic acid (DNA) nucleotide.

In another embodiment, the invention provides methods for treating the mycosis fungoides (MF) form of CTCL comprising administering an oligonucleotide inhibitor of miR-155 that has a sequence of 11 to 14 nucleotides, wherein the oligonucleotide inhibitor is fully complementary to a mature sequence of miR-155 and has a full phosphorothioate backbone; and wherein at least 7 nucleotides of said oligonucleotide inhibitor are modified nucleotides and at least the second nucleotide from the 5' end of the oligonucleotide inhibitor is a deoxyribonucleic acid (DNA) nucleotide.

In yet another embodiment, the invention provides methods for treating the mycosis fungoides (MF) form of CTCL comprising administering an oligonucleotide inhibitor of miR-155 that has a sequence of 11 to 14 nucleotides, wherein the oligonucleotide inhibitor is fully complementary to a mature sequence of miR-155 and has a full phosphorothioate backbone; and wherein at least the first three nucleotides from 3' end of said oligonucleotide inhibitor are modified nucleotides and at least the fourth and fifth nucleotides from the 5' end of the oligonucleotide inhibitor are deoxyribonucleic acid (DNA) nucleotides.

In certain embodiments, the method for treating the MF form of CTCL comprises administering an oligonucleotide inhibitor of miR-155 selected from the group consisting of SEQ ID NO: 22, SEQ ID NO: 23, and SEQ ID NO: 25. In some other embodiments, the method for treating the MF form of CTCL comprises administering an oligonucleotide inhibitor of miR-155 selected from the group consisting of SEQ ID NOs: 33, 39, 43, 44, 47, 58, 84, 99, 111, 115, and 120.

The invention also encompasses methods for treating CTCL comprising administering an oligonucleotide inhibitor of miR-155 according to the invention in combination with a second therapeutic agent. Current treatments for CTCL include skin-directed therapies such as topical steroids, topical nitrogen mustard (mechlorethamine HCL), topical retinoids, phototherapy, ultraviolet light treatment, psoralen ultraviolet light treatment, radiotherapy, electron beam therapy, etc. and systemic therapies such as administration of histone deacetylase (HDAC) inhibitors, retinoids (bexarotene), interferon, and low dose antifolates (e.g. methotrexate and pralatrexate). Additional treatment options such as anti-CD30 antibody (e.g. Brentuximab), anti-CCR4 antibody (e.g. mogamulizumab), and anti-PD-1 or anti-PD-L1 antibody are currently being tested. The second therapeutic agent generally comprises an agent or a therapy selected from one of these treatments. For example, the invention encompasses methods for treating CTCL by administering the oligonucleotide inhibitor of miR-155 in combination with a second therapy such as treatment with HDAC inhibitors, retinoids, interferon, antifolates, topical steroids, topical retinoids, topical nitrogen mustard, phototherapy, ultraviolet light, psoralen and ultraviolet light, radiotherapy, electron beam therapy, anti-CD30 antibody (e.g. Brentuximab), anti-CCR4 antibody (e.g. mogamulizumab), and anti-PD-1 or anti-PD-L1 antibody.

A variety of HDAC inhibitors are known, some of which are approved by FDA for clinical use and some are being tested in clinical trials. The methods for treating cancer according to the invention encompass the use of HDAC inhibitors including, but not limited to, vorinostat, romidepsin, panobinostat (LBH589), mocetinostat, belinostat (PXD101), abexinostat, CI-994 (tacedinaline), and MS-275 (entinostat). In embodiments where a second therapy/agent is included, the second therapy/agent may be administered at different times prior to or after administration of the oligonucleotide inhibitor of miR-155. Prior administration includes, for instance, administration of the first agent within the range of about one week to up to 30 minutes prior to administration of the second agent. Prior administration may also include, for instance, administration of the first agent within the range of about 2 weeks to up to 30 minutes prior to administration of the second agent. After or later administration includes, for instance, administration of the second agent within the range of about one week to up to 30 minutes after administration of the first agent. After or later administration may also include, for instance, administration of the second agent within the range of about 2 weeks to up to 30 minutes after administration of the first agent.

The invention also provides methods for reducing or inhibiting proliferation of cancer cells, particularly malignant T cells, by administering an oligonucleotide inhibitor of miR-155 that has a sequence of 11 to 16 nucleotides, wherein the oligonucleotide inhibitor is fully complementary to a mature sequence of miR-155 and has a full phosphorothioate backbone; and wherein at least the first three nucleotides from the 3' end of said oligonucleotide inhibitor are locked nucleotides and at least the second nucleotide from the 5' end of the oligonucleotide inhibitor is a deoxyribonucleic acid (DNA) nucleotide.

In another embodiment, the invention provides methods for reducing or inhibiting proliferation of cancer cells, particularly malignant T cells, comprising administering an oligonucleotide inhibitor of miR-155 that has a sequence of 11 to 14 nucleotides, wherein the oligonucleotide inhibitor is fully complementary to a mature sequence of miR-155 and has a full phosphorothioate backbone; and wherein at least the first three nucleotides from the 3' end of said oligonucleotide inhibitor are modified nucleotides and at least the second nucleotide from the 5' end of the oligonucleotide inhibitor is a deoxyribonucleic acid (DNA) nucleotide.

In another embodiment, the invention provides methods for reducing or inhibiting proliferation of cancer cells, particularly malignant T cells, comprising administering an oligonucleotide inhibitor of miR-155 that has a sequence of 11 to 14 nucleotides, wherein the oligonucleotide inhibitor is fully complementary to a mature sequence of miR-155 and has a full phosphorothioate backbone; and wherein at least 7 nucleotides of said oligonucleotide inhibitor are modified nucleotides and at least the second nucleotide from the 5' end of the oligonucleotide inhibitor is a deoxyribonucleic acid (DNA) nucleotide.

In yet another embodiment, the invention provides methods for reducing or inhibiting proliferation of cancer cells, particularly malignant T cells, comprising administering an oligonucleotide inhibitor of miR-155 that has a sequence of 11 to 14 nucleotides, wherein the oligonucleotide inhibitor is fully complementary to a mature sequence of miR-155 and has a full phosphorothioate backbone; and wherein at least the first three nucleotides from 3' end of said oligonucleotide inhibitor are modified nucleotides and at least the fourth and fifth nucleotides from the 5' end of the oligonucleotide inhibitor are deoxyribonucleic acid (DNA) nucleotides.

In certain embodiments, methods for reducing or inhibiting proliferation of cancer cells, particularly malignant T cells, comprises administering an oligonucleotide inhibitor of miR-155 selected from the group consisting of SEQ ID NO: 22, SEQ ID NO: 23, and SEQ ID NO: 25. In some other embodiments, methods for reducing or inhibiting proliferation of cancer cells, particularly malignant T cells, comprises administering an oligonucleotide inhibitor of miR-155 selected from the group consisting of SEQ ID NOs: 33, 39, 43, 44, 47, 58, 84, 99, 111, 115, and 120.

Malignant T cells include cutaneous T cell lymphoma (CTCL) cells, CD4$^+$ T cells and memory T cells. Administration of an oligonucleotide inhibitor of the present invention reduces the activity or function of miR-155 and/or up-regulates one or more target genes of miR-155 in malignant T cells following administration. Methods for reducing or inhibiting proliferation of cancer cells also include the use of second therapy/agents described above along with administration of the present oligonucleotide inhibitors.

In certain embodiments, the methods encompassed by the invention comprise administering 18.75, 37.5, or 75 mg of the oligonucleotide inhibitor of the invention per skin lesion of the patient. In other embodiments, the methods of the invention comprise systemically administering a total of about 37.5, 75, 150, 300, 600, 900, or 1200 mg, including values therebetween, of the oligonucleotide inhibitor of the invention to the patient. In yet some other embodiments, the methods of the invention comprise systemically administering a total of about 350, 700, 1050, 1400, 1750, 2100, 2450, 2800, 3150, or 3500 mg, including values therebetween, of the oligonucleotide inhibitor of the invention to the patient.

Preferably, administration of an oligonucleotide inhibitor of the present invention to the subject results in the improvement of one or more symptoms or pathologies associated with cancer. For instance, in one embodiment, administration of an oligonucleotide inhibitor of the present invention alone or in combination with a second therapeutic agent such as a HDAC inhibitor reduces the number of skin lesions; number of red, itchy patches or plaques on skin; and/or formation of new skin lesions/patches/plaques associated with CTCL. In one embodiment, administration of an oligonucleotide inhibitor of the present invention alone or in combination with a second therapeutic agent such as a HDAC inhibitor reduces or inhibits migration of malignant T lymphocytes to the skin. In another embodiment, administration of an oligonucleotide inhibitor of the present invention alone or in combination with a second therapeutic agent reduces total malignant T lymphocytes in the skin. In yet another embodiment, administration of an oligonucleotide inhibitor of the present invention alone or in combination with a second therapeutic agent reduces the number of malignant T cells that may escape or migrate from the skin into the periphery.

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human.

Any of the oligonucleotide inhibitors of miR-155 described herein can be delivered to the target cell (e.g. malignant T cells) by delivering to the cell an expression vector encoding the miR-155 oligonucleotide inhibitor. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. In one particular embodiment, the viral vector is a lentiviral vector or an adenoviral vector. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing an oligonucleotide inhibitor of miR-155 comprises a promoter operably linked to a polynucleotide sequence encoding the oligonucleotide inhibitor. The phrase "operably linked" or "under transcriptional control" as used herein means that the promoter is in the correct location and orientation in relation to a polynucleotide to control the initiation of transcription by RNA polymerase and expression of the polynucleotide.

As used herein, a "promoter" refers to a DNA sequence recognized by the synthetic machinery of the cell, or introduced synthetic machinery, required to initiate the specific transcription of a gene. Suitable promoters include, but are not limited to RNA pol I, pol II, pol III, and viral promoters (e.g. human cytomegalovirus (CMV) immediate early gene promoter, the SV40 early promoter, and the Rous sarcoma virus long terminal repeat). In one embodiment, the promoter is a T-cell specific promoter such as the proximal and distal promoters of the lck gene or promoter and enhancer sequences of the CD4 gene, etc.

In certain embodiments, the promoter operably linked to a polynucleotide encoding a miR-155 oligonucleotide inhibitor can be an inducible promoter. Inducible promoters are known in the art and include, but are not limited to, tetracycline promoter, metallothionein IIA promoter, heat shock promoter, steroid/thyroid hormone/retinoic acid response elements, the adenovirus late promoter, and the inducible mouse mammary tumor virus LTR.

Methods of delivering expression constructs and nucleic acids to cells are known in the art and can include, for example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

The present invention also provides methods for diagnosing CTCL and methods for monitoring clinical status of a patient undergoing the treatment for CTCL. The invention shows that administration of antimiR-155 compounds of the invention up-regulates and/or down-regulates a unique set of genes in all three MF cell lines (HuT102, MJ, and MyLa) compared to control-treated cells or Sezary syndrome cells. The invention contemplates using a gene expression signature based on this unique set of genes to diagnose MF subtype of CTCL as well to monitor progress of the CTCL treatment with miR-155 inhibitors. For instance, the invention shows that a set of genes listed in Table 2 are up-regulated or down-regulated in all three MF cell lines in response to antimiR-155 compounds of the invention. In one embodiment, the invention provides methods for diagnosing CTCL by measuring the expression levels of one or more genes listed in Table 2 in a subject suspected of suffering from CTCL, comparing the expression levels to reference levels (e.g. expression levels in a healthy subject or expression levels in non-cancer cells of the CTCL subject), and diagnosing the subject as having CTCL if the expression levels in the subject are down-regulated or up-regulated compared to reference levels.

TABLE 2

List of genes significantly up-regulated or down-regulated in all three MF cell lines in response to present antimiR-155 compounds

| CFLAR | GALC | SMARCA2 | HIF1A | FSD1L | CLINT1 |
|---|---|---|---|---|---|
| CIAPIN1 | TAB2 | OSTM1 | CCNB1IP1 | TLE4 | SUB1 |
| GCFC2 | TRAF1 | UBA5 | BRMS1L | GATA3 | ST8SIA4 |
| LAMP2 | RC3H2 | APLP2 | TM9SF1 | OBFC1 | GNPDA1 |

TABLE 2-continued

List of genes significantly up-regulated or down-regulated in all three MF cell lines in response to present antimiR-155 compounds

| | | | | | |
|---|---|---|---|---|---|
| KDM7A | PITHD1 | SCAMP1 | NELFCD | DNAJC12 | H2AFY |
| GGCT | SLC2A3 | WDFY1 | PRPF6 | TSPAN14 | SMAD5 |
| JARID2 | ASUN | DIMT1 | TCFL5 | RAD51C | CSNK1A1 |
| MBTD1 | IPO5 | SEPHS1 | AHCY | DHX40 | NIT2 |
| COX15 | DGKA | ZFAND6 | DNTTIP1 | RPS6KB1 | KPNA1 |
| ZMYND11 | FAM107B | UIMC1 | TIMP1 | PIGL | TUSC2 |
| ZDHHC6 | TRMT11 | GMCL1 | NDFIP2 | CPD | NCBP2 |
| BIRC3 | SP100 | KLHL42 | SLC25A15 | PEX12 | HEMK1 |
| DEPDC1 | TRAM1 | DNM1L | ARL2BP | RAB5C | MAPKAPK3 |
| NR1H3 | CBFB | TGDS | HSDL1 | MLX | COMMD2 |
| TBPL1 | TGFBR3 | FKBP1A | USP10 | UNC119 | ACTR1B |
| PIAS1 | GBA2 | TRMT6 | TSC2 | TMEM33 | GTF3C2 |
| TBC1D23 | HLTF | PEBP1 | EIF3J | CLCN3 | GCA |
| GOPC | MPP5 | GANAB | OIP5 | GALNT7 | STAT1 |
| VAMP3 | PDE8A | MAEA | BLOC1S6 | KLHL5 | MOB4 |
| HOMER3 | PTGS2 | GLG1 | NCALD | ZPR1 | GORASP2 |
| AKR7A2 | PICALM | pk | TSTA3 | HIPK3 | SLC1A4 |
| AP5M1 | NUAK1 | GEMIN2 | ASAH1 | SLC35F2 | NFE2L2 |
| KIF1B | DPP8 | RFFL | RELB | ELK3 | PLEKHA3 |
| FAM168A | SRI | CDC7 | FAM32A | VPS29 | EDEM3 |
| FOXO3 | TUBA3D | ERMP1 | TBCB | COPS7A | CD58 |
| UCHL3 | EXOSC7 | HSD17B7P2 | PRKD2 | BTN3A3 | WARS2 |
| ITGB1BP1 | TPD52 | CIRBP | CDC37 | ASF1A | SLAMF1 |
| CPSF3 | TOP2B | MAPK1 | ARRDC2 | STK38 | SSX2IP |
| TRIM32 | TM9SF3 | MFNG | NAMPT | MRPL18 | NENF |
| PPP6C | UBE2T | KIAA0930 | WDR91 | ALDH5A1 | RCN2 |
| HSDL2 | DYNC1I2 | CSF2RB | GARS | ACOT13 | CTSD |
| VPS4B | UBE2K | SDR39U1 | RPA3 | GMNN | KMT2A |
| RBM25 | C12orf5 | CNIH1 | GLCCI1 | TRIM38 | PLAGL1 |
| SLC17A5 | KEAP1 | TIMM9 | PSMA2 | PHACTR2 | MYB |
| TAF12 | RAB21 | CEP128 | RHEB | KIF20A | TMEM5 |
| HSPH1 | RBCK1 | IMPA1 | FAM8A1 | ATG12 | MSI2 |
| DUSP4 | RRBP1 | RRAS2 | SDCBP | DDX46 | ZUFSP |
| NAA50 | PDCD2L | SARAF | FXYD2 | G3BP1 | PITPNC1 |
| CD80 | RAP1B | ARL8B | TUBGCP4 | FARS2 | FAM69A |
| LRIF1 | SMARCA4 | NAPG | ADAM10 | MUT | BTG3 |
| FYTTD1 | TST | NARS | HADHB | DYNLT1 | XPC |
| ACOT9 | CALU | CCNH | ATAD1 | WTAP | ATP6V1C1 |
| CDK2 | MTX2 | DDB2 | ABI2 | C7orf55-LUC7L2 | SAMSN1 |
| FAM199X | GAD1 | ETS1 | BMP2K | SH3KBP1 | SLC26A2 |
| LPGAT1 | SNRPN | RFK | FAM60A | TERF1 | DCK |
| FAM210B | PSMG2 | UBQLN1 | ZCRB1 | AUH | BACH1 |
| SDC4 | EIF2AK4 | ANXA1 | COMMD4 | STOM | SFXN2 |
| CSE1L | CALML4 | HILPDA | SCAPER | POLE3 | EEF1A1 |
| TMEM189-UBE2V1 | PSMA1 | TES | FANCI | GLUD1 | WDYHV1 |
| STAU1 | DCTD | MAP3K7 | TXNL4B | ADD3 | BUB1B |
| XPO5 | CDKN2D | PRADC1 | RANBP10 | BTBD10 | GATAD1 |
| OARD1 | PARP2 | NTPCR | RPRD1A | SSRP1 | PINK1 |
| GLO1 | ARHGEF6 | TAF5L | ITGB3BP | CELF1 | RAPGEF6 |
| RIOK1 | ZSWIM6 | SP110 | CTTNBP2NL | TMEM138 | MRPL10 |
| SLC35B3 | ATXN10 | MRPS9 | PSMA5 | EI24 | CCDC117 |
| ATXN1 | UBE2M | VPS36 | ALDH9A1 | PDCD4 | GNE |
| RAP2A | LRRC47 | BORA | CREG1 | ITPR1 | CALM3 |
| CLPP | COX7B | PHF11 | RGL1 | TMEM263 | TMPRSS3 |
| ATP1A1 | SH3BP5 | NUDT15 | PYCR2 | TWF1 | SQSTM1 |
| PRKCI | NDFIP1 | IL6 | CHAC2 | SRFBP1 | CYB561A3 |
| AIM2 | VIMP | TTC5 | CIAO1 | GUF1 | EXTL2 |
| EIF5A2 | CHSY1 | VEZF1 | TPRKB | TMEM123 | DENND2D |
| SNHG16 | ACTR10 | RPS6KC1 | RALB | GPD1L | IER5 |
| COX18 | DNAJB1 | C9orf78 | ZC3H8 | PELO | BPNT1 |
| GYG1 | TBC1D14 | STX17 | KIAA1715 | CENPH | TYW5 |
| ZMYM6 | HRSP12 | ATP6V1G1 | SUMF1 | ANAPC1 | H3F3A |
| TKT | SYT11 | ENPP2 | FAM134A | CETN3 | RNF149 |
| ZNF691 | SERINC3 | APTX | ARL6IP5 | RASSF3 | CDC42EP3 |
| METAP1 | RFXAP | TCF19 | KLHL8 | RPIA | S100A11 |
| RNF123 | CSNK1G2 | FLOT1 | TBCK | ARFIP1 | CCNYL1 |
| ABCE1 | BAG5 | TBCA | PRKRA | YRDC | CCPG1 |
| MOCS2 | WBP1L | RNASEH1 | SLC26A11 | C6orf106 | NUDCD2 |
| WDR41 | AKIP1 | PRNP | FRAT2 | SLC39A10 | CHCHD7 |
| GRPEL2 | ATMIN | ZNF217 | YIPF6 | WDR45 | AC093323.3 |
| SLC35A1 | TMEM41B | KRCC1 | C5orf24 | GMFB | FEZ2 |
| CAMLG | WEE1 | MRPL13 | DEXI | IGF2R | PPID |
| HEY1 | AP1G1 | ISG20 | P2RY8 | PSMD12 | SEPW1 |
| CTSB | FAM96A | RASGRP1 | C8orf33 | FAR1 | TMTC2 |
| RAD21 | TMEM194A | MIR4435-1HG | ADI1 | MRPL42 | TCAIM |

TABLE 2-continued

List of genes significantly up-regulated or down-regulated in all three MF cell lines in response to present antimiR-155 compounds

| | | | | | |
|---|---|---|---|---|---|
| C7orf55 | HDHD2 | TADA2B | ANXA2 | TUBA3C | PACS2 |
| YWHAZ | GPX4 | NOC3L | SRPR | MAK16 | SEPHS2 |
| KIAA0196 | TSR1 | SSSCA1 | DAZAP2 | TCAF1 | FAM72B |
| NFIL3 | FTH1 | CXorf23 | BCOR | TXNRD1 | ARID2 |
| GKAP1 | RAB4A | RBM4B | TMEM186 | STK39 | BLOC1S2 |
| MID1IP1 | DDIT4 | FBXO45 | RAD51D | GRK5 | ACADSB |
| PMPCA | IRF2BP2 | DENND4A | SDHAP1 | PRC1 | SUPT3H |
| HPRT1 | BMI1 | AKIRIN1 | BRWD1 | C1orf174 | ATXN1L |
| TRUB1 | ARF4 | KIAA1551 | MORF4L1 | COX20 | RP11-175O19.4 |
| FRAT1 | CMAHP | SRP72 | LAMP1 | MICB | MCTS1 |
| PTPLA | POLR3D | DENND6A | BICD2 | TRIM27 | AC093673.5 |
| ARL5B | STAT3 | PDE12 | POLR1D | ZBTB10 | LINC00657 |
| IKBIP | LDLRAD4 | YIF1A | MKL2 | LIN52 | HNRNPA3 |
| ASH1L-AS1 | SNTB2 | CCNE2 | TAF9B | DNAJC19 | NT5DC1 |
| PLGLA | MAP2K1 | RAB6A | SECISBP2 | ANKRD28 | DCUN1D3 |
| AP001258.4 | CSNK1G1 | CDC26 | SEMA4D | SACM1L | KANSL1-AS1 |
| CCDC71L | NMD3 | EID2 | ZFP69B | TSN | PTGER4 |
| OTUD6B-AS1 | CRADD | DNAJC30 | EIF4EBP1 | ARHGAP19 | IARS |
| CUX1 | ARL13B | RPS6KA3 | TPRG1 | IRF9 | |

In additional embodiments, the invention provides a method for selecting a subject for treatment of CTCL comprising determining a level of expression of one or more genes in CTCL cells of the subject, wherein the one or more genes are selected from a set of genes modulated in all MF cells, e.g. Table 2; comparing the level of the one or more genes in the CTCL cells of the subject to a reference level of the one or more genes; and selecting a subject having an increase or a decrease in the level of the one or more genes in the CTCL cells compared to the reference level for treatment of CTCL. In another embodiment, a method for selecting a subject for treatment of CTCL comprises determining a level of expression of 4 or more genes selected from the group consisting of INPP50/SHIP1, Jarid2, Picalm, Bach1, Wee1, CUX1, Cebpb, SPIB/PU.1, and IL7R, in CTCL cells of the subject; comparing the level of the 4 or more genes in the CTCL cells of the subject to a reference level of the 4 or more genes; and selecting a subject having a decrease in the level of the 4 or more genes in the CTCL cells compared to the reference level for treatment of CTCL. In one embodiment, the method for selecting a subject for treatment of CTCL comprises determining the level of 4 genes, Bach1, Jarid2, Picalm, and SHIP1, in CTCL cells of the subject in comparison to a reference level of the 4 genes. In certain embodiments, the method for selecting a subject for treatment of CTCL comprises determining the level of 4 genes, Bach1, Jarid2, Picalm, and SHIP1, in CTCL cells of the subject in comparison to a reference level of the 4 genes; and selecting a subject having at least 2-fold decrease in the level of the 4 genes in the CTCL cells compared to the reference level for treatment of CTCL. In one embodiment, the reference level is the level of expression of the same genes in control oligonucleotide-treated cells. In another embodiment, the reference level is the level of expression of the same genes in Sézary syndrome cells. In yet another embodiment, the reference level is the level of expression of the same genes in a healthy subject (e.g., a subject that does not present with two or more symptoms of a skin cancer, a subject that has not been diagnosed with a skin cancer, and/or a subject that has no family history of skin cancer).

The invention also provides methods for assessing the efficacy of a treatment with antimiR-155 compounds comprising determining a level of expression of one or more genes in cells of a subject prior to the treatment with antimiR-155 compounds, wherein the one or more genes are selected from a set of genes modulated in all MF cells, e.g. Table 2; determining the level of expression of the same one or more genes in cells of the subject after treatment with antimiR-155 compounds; and determining the treatment to be effective, less effective, or not effective based on the expression levels prior to and after the treatment. That is, in one embodiment, the genes listed in Table 2 serve as a biomarker for clinical efficacy of the antimiR-155 treatment.

In some embodiments, the invention provides methods of diagnosing CTCL by measuring the level of miR-155 in a subject suspected of suffering from CTCL in comparison to a reference level, wherein the higher expression of miR-155 in the subject indicates the subject is suffering from CTCL. The level of expression of miR-155 in the subject suspected of suffering from CTCL may be determined using cells isolated from skin lesions of the subject, plasma, serum, white blood cells, or PBMCs. In certain embodiments, the invention provides methods of diagnosing mycosis fungoides form of CTCL by measuring the level of miR-155 in a subject in comparison to a reference level, wherein the higher expression of miR-155 in the subject indicates the subject is suffering from the MF form of CTCL. In some other embodiments, the invention provides methods for assessing the response to an antimiR-155 treatment by determining a level of expression of miR-155 in the subject undergoing the treatment in comparison to a reference level of miR-155. The reference level can be the level of miR-155 in a healthy subject or the mean or median level of miR-155 from a group of healthy subjects or the level of miR-155 in a subject having Sézary syndrome.

The present invention also provides pharmaceutical compositions comprising an oligonucleotide inhibitor of miR-155 as disclosed herein and a pharmaceutically acceptable carrier or excipient. In one embodiment, the pharmaceutical composition comprises an effective dose of an oligonucleotide inhibitor of miR-155 having a sequence of 11 to 16 nucleotides, wherein the oligonucleotide inhibitor is fully complementary to a mature sequence of miR-155 and has a full phosphorothioate backbone; and wherein at least the first three nucleotides from the 3' end of the oligonucleotide inhibitor are locked nucleotides and at least the second nucleotide from the 5' end of the oligonucleotide inhibitor is a deoxyribonucleic acid (DNA) nucleotide.

In another embodiment, the pharmaceutical composition comprises an effective dose of an oligonucleotide inhibitor of miR-155 that has a sequence of 11 to 14 nucleotides, wherein the oligonucleotide inhibitor is fully complementary to a mature sequence of miR-155 and has a full phosphorothioate backbone; and wherein at least the first three nucleotides from the 3' end of said oligonucleotide inhibitor are modified nucleotides and at least the second nucleotide from the 5' end of the oligonucleotide inhibitor is a deoxyribonucleic acid (DNA) nucleotide.

In another embodiment, the pharmaceutical composition comprises an effective dose of an oligonucleotide inhibitor of miR-155 that has a sequence of 11 to 14 nucleotides, wherein the oligonucleotide inhibitor is fully complementary to a mature sequence of miR-155 and has a full phosphorothioate backbone; and wherein at least 7 nucleotides of said oligonucleotide inhibitor are modified nucleotides and at least the second nucleotide from the 5' end of the oligonucleotide inhibitor is a deoxyribonucleic acid (DNA) nucleotide.

In yet another embodiment, the pharmaceutical composition comprises an effective dose of an oligonucleotide inhibitor of miR-155 that has a sequence of 11 to 14 nucleotides, wherein the oligonucleotide inhibitor is fully complementary to a mature sequence of miR-155 and has a full phosphorothioate backbone; and wherein at least the first three nucleotides from 3' end of said oligonucleotide inhibitor are modified nucleotides and at least the fourth and fifth nucleotides from the 5' end of the oligonucleotide inhibitor are deoxyribonucleic acid (DNA) nucleotides.

In certain embodiments, pharmaceutical compositions comprise an effective dose of an oligonucleotide inhibitor having a sequence selected from the group consisting of SEQ ID NO: 22, SEQ ID NO: 23, and SEQ ID NO: 25. In some other embodiments, pharmaceutical compositions comprise an effective dose of an oligonucleotide inhibitor having a sequence selected from the group consisting of SEQ ID NOs: 33, 39, 43, 44, 47, 58, 84, 99, 111, 115, and 120. In yet other embodiments, the pharmaceutical composition comprises an oligonucleotide inhibitor having a sequence selected from the sequences listed in Table 1.

An "effective dose" is an amount sufficient to effect a beneficial or desired clinical result. An effective dose of an oligonucleotide inhibitor of miR-155 of the invention may be from about 1 mg/kg to about 100 mg/kg, about 2.5 mg/kg to about 50 mg/kg, or about 5 mg/kg to about 25 mg/kg. In some embodiments, an effective dose may be about 18.75, 37.5, or 75 mg of the oligonucleotide inhibitor per skin lesion of the patient. The precise determination of what would be considered an effective dose may be based on factors individual to each patient, including their size, age, type of disorder, and form of inhibitor (e.g. naked oligonucleotide or an expression construct etc.). Therefore, dosages can be readily ascertained by those of ordinary skill in the art from this disclosure and the knowledge in the art.

In certain embodiments, the invention contemplates the use of a HDAC inhibitor in combination with the oligonucleotide inhibitors of the invention. In embodiments where a HDAC inhibitor is included, the HDAC inhibitor may be administered concurrently but in separate formulations or sequentially. In other embodiments, the HDAC inhibitor may be administered at different times prior to or after administration of a miR-155 inhibitor. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

In one embodiment, the invention provides topical compositions comprising the oligonucleotide inhibitors of miR-155 and one or more cosmetically or pharmaceutically acceptable carriers or excipients. The term "cosmetically acceptable" as used herein means that the carriers or excipients are suitable for use in contact with tissues (e.g., the skin) without undue toxicity, incompatibility, instability, irritation, allergic response, and the like.

Cosmetic or pharmaceutical carriers or excipients can be liquids, such as water and oils, including those of petroleum, animal, vegetable or synthetic origin, such as peanut oil, soybean oil, mineral oil, sesame oil and the like. Topical compositions often comprise an oil-in-water or a water-in-oil emulsion. The invention encompasses using such emulsions for preparing topical composition of antimiR-155 compounds. Suitable pharmaceutical carriers are described in "Remington's Pharmaceutical Sciences" by E. W. Martin. Suitable cosmetic carriers are described below.

In one embodiment, the cosmetically acceptable topical carrier is from about 50% to about 99.99%, by weight, of the composition (e.g., from about 80% to about 99%, by weight, of the composition). The topical compositions include, but are not limited to, solutions, lotions, creams, gels, sticks, sprays, ointments, cleansing liquid washes, solid bars, shampoos, pastes, foams, powders, mousses, shaving creams, wipes, patches, nail lacquers, wound dressing, adhesive bandages, hydrogels, and films. These product types may comprise several types of cosmetically acceptable topical carriers including, but not limited to solutions, emulsions (e.g., microemulsions and nanoemulsions), gels, solids and liposomes. Certain non-limitative examples of such carriers are set forth hereinbelow. Other suitable carriers may be formulated by those of ordinary skill in the art.

Topical compositions useful in the present invention may be formulated as a solution comprising an emollient. Such compositions preferably contain from about 1% to about 50% of an emollient(s). As used herein, the term "emollient" refers to materials used for the prevention or relief of dryness, as well as for the protection of the skin. A number of suitable emollients are known and may be used in the present invention. For example, Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997) (hereinafter "ICI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72-73 (1972) and the ICI Handbook pp. 1693-1697.

The topical compositions useful in the present invention may be formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, in McCutcheon's Detergents and Emulsifiers, North American Edition, pp. 317-324 (1986), and the ICI Handbook, pp. 1673-1686.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well known in the cosmetic art and are useful in the present invention. Multiphase emulsion compositions, for example the water-in-oil-in-water type, as disclosed in U.S. Pat. Nos. 4,254,105 and 4,960,764, may also be useful in the present invention. In general, such single or multiphase emulsions contain water, emollients, and emulsifiers as essential ingredients.

The topical compositions of this invention can also be formulated as a gel (e.g., an aqueous, alcohol, alcohol/water, or oil gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprise between about 0.1% and 5%, by weight, of such gelling agents.

Liposomal formulations are also useful compositions of the subject invention. In one embodiment, the oligonucleotides are contained within the liposome. Examples of liposomes are unilamellar, multilamellar, and paucilamellar liposomes, which may or may not contain phospholipids. Such compositions can be prepared by combining the oligonucleotide inhibitor with a phospholipid, such as dipalmitoylphosphatidyl choline, cholesterol and water. Commercially available fat emulsions that may be suitable for delivering the nucleic acids of the invention to cancer cells or the skin tissue include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are herein incorporated by reference in their entireties.

The liposome preparation may then be incorporated into one of the above carriers (e.g., a gel or an oil-in-water emulsion) in order to produce the liposomal formulation. Other compositions and uses of topically applied liposomes are described in Mezei, M., "Liposomes as a Skin Drug Delivery System", Topics in Pharmaceutical Sciences (D. Breimer and P. Speiser, eds.), Elsevier Science Publishers B. V., New York, N.Y., 1985, pp. 345-358, PCT Patent Application No. WO96/31194, Niemiec, et al., 12 Pharm. Res. 1184-88 (1995), and U.S. Pat. No. 5,260,065.

In one embodiment, the liposomes are present in the topical composition in an amount, based upon the total volume of the composition, of from about 5 mg/ml to about 100 mg/ml such as from about 10 mg/ml to about 50 mg/ml.

In addition to the above carriers and excipients, other emollients and surface active agents can be incorporated in the emulsions, including glycerol trioleate, acetylated sucrose distearate, sorbitan trioleate, polyoxyethylene (1) monostearate, glycerol monooleate, sucrose distearate, polyethylene glycol (50) monostearate, octylphenoxypoly (ethyleneoxy) ethanol, decaglycerin penta-isostearate, sorbitan sesquioleate, hydroxylated lanolin, lanolin, triglyceryl diisostearate, polyoxyethylene (2) oleyl ether, calcium stearoyl-2-lactylate, methyl glucoside sesquistearate, sorbitan monopalmitate, methoxy polyethylene glycol-22/dodecyl glycol copolymer (Elfacos E200), polyethylene glycol-45/dodecyl glycol copolymer (Elfacos ST9), polyethylene glycol 400 distearate, and lanolin derived sterol extracts, glycol stearate and glycerol stearate; alcohols, such as cetyl alcohol and lanolin alcohol; myristates, such as isopropyl myristate; cetyl palmitate; cholesterol; stearic acid; propylene glycol; glycerine, sorbitol and the like.

In certain embodiments, liposomes used for delivery are amphoteric liposomes such SMARTICLES® (Marina Biotech, Inc.) which are described in detail in U.S. Pre-grant Publication No. 20110076322. The surface charge on the SMARTICLES® is fully reversible which make them particularly suitable for the delivery of nucleic acids. SMARTICLES® can be delivered via injection, remain stable, and aggregate free and cross cell membranes to deliver the nucleic acids.

One will generally desire to employ appropriate salts and buffers to render delivery vehicles stable and allow for uptake by target cells. Pharmaceutical compositions of the present invention comprise an effective amount of the delivery vehicle comprising the inhibitor polynucleotides (e.g. liposomes or other complexes or expression vectors) dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The active compositions of the present invention may include classic pharmaceutical preparations. Administration of these compositions according to the present invention may be via any common route so long as the target tissue is available via that route. This includes oral, topical, parenteral, intradermal, subcutaneous, or intravenous injection. In another embodiment, compositions comprising oligonucleotide inhibitors of miR-155 as described herein may be formulated in the form suitable for a topical application such as a cream, ointment, paste, lotion, or gel.

The active compounds may also be administered parenterally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids), or from organic acids (e.g., acetic, oxalic, tartaric, mandelic, and the like). Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, compositions are preferably administered in a manner compatible with the dosage formulation and in such amount as is therapeutically effective. The formulations may easily be administered in a variety of dosage forms such as injectable solutions, cream, ointment, paste, lotion, or gel and the like. For parenteral administration in an aqueous solution, for example, the solution generally is suitably buffered and the liquid diluent first rendered isotonic for example with sufficient saline or glucose. Such aqueous solutions may be used, for example, for intravenous, subcutaneous, and intradermal administration. Preferably, sterile aqueous media are employed as is known to those of skill in the art, particularly in light of the present disclosure. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by regulatory agencies.

In certain embodiments of the invention, the pharmaceutical compositions of the invention are packaged with or stored within a device for administration. Devices for injectable formulations include, but are not limited to, pre-filled syringes, injection ports, autoinjectors, injection pumps, and injection pens. Devices for aerosolized or powder formulations include, but are not limited to, inhalers, insufflators, aspirators, and the like. Devices for dermal delivery of compositions of the present invention also include dermal microneedle injection or patches. Thus, the present invention includes administration devices comprising a pharmaceutical composition of the invention for treating or preventing one or more of the disorders described herein.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1: Oligonucleotide Inhibitors of miR-155 ("antimiR-155") are Active in Mycosis Fungoides Cell Lines which Show Increased miR-155 Expression To characterize miR-155-5p expression in cell lines derived from CTCL patients, the absolute levels of miR-155-5p in mycosis fungoides (MF), Sézary syndrome (SS), and a CTCL cell line classified as neither MF nor SS were measured. The cellular, pathological, and molecular characteristics of the cell lines examined are shown in Table 3.

TABLE 3

Characteristics of CTCL Cell Lines

| Name | Disease | Age | Tissue source | Expressed Antigens | Molecular Characteristics |
|---|---|---|---|---|---|
| HuT78 | Sézary syndrome | 53 | Peripheral blood | CD4+ | HTLV− |
| MJ | Mycosis fungoides | 50 | Peripheral blood | CD4+, CD3+, CD2+ | HTLV+ |
| My-La | Mycosis fungoides | 82 | Skin plaque | CD4+, CD3+, CD2+ | HTLV− |
| HuT102 | Mycosis fungoides | 26 | Lymph node | CD4+ | HTLV+ |

TABLE 3-continued

Characteristics of CTCL Cell Lines

| Name | Disease | Age | Tissue source | Expressed Antigens | Molecular Characteristics |
|------|---------|-----|---------------|--------------------|---------------------------|
| HH | Neither mycosis fungoides nor Sézary syndrome | 61 | Peripheral blood | CD4+, CD3+, CD2+, CD30+ | HTLV– |

The absolute expression of miR-155-5p in the CTCL cell lines compared to normal peripheral CD4+ helper T-cells was measured by real time PCR, using total RNA isolated from each cell type as a template. Standard curves correlating Ct value to miR-155-5p copy number were generated using a synthetic miR-155-5p RNA template. The copy number per cell of miR-155-5p was extrapolated from the Ct values determined for CTCL RNA samples or normal CD4+ T-cell RNA sample using the standard curve generated with the synthetic template, assuming 10 pg of total RNA per cell (FIG. 1). The mycosis fungoides cell lines (HuT102, MJ, and My-La), as well as the idiopathic cell line (HH), showed high expression of miR-155-5p compared to normal CD4+ T-cells, while the cell line derived from a Sézary syndrome patient (HuT78) did not overexpress miR-155-5p.

Figure 2:
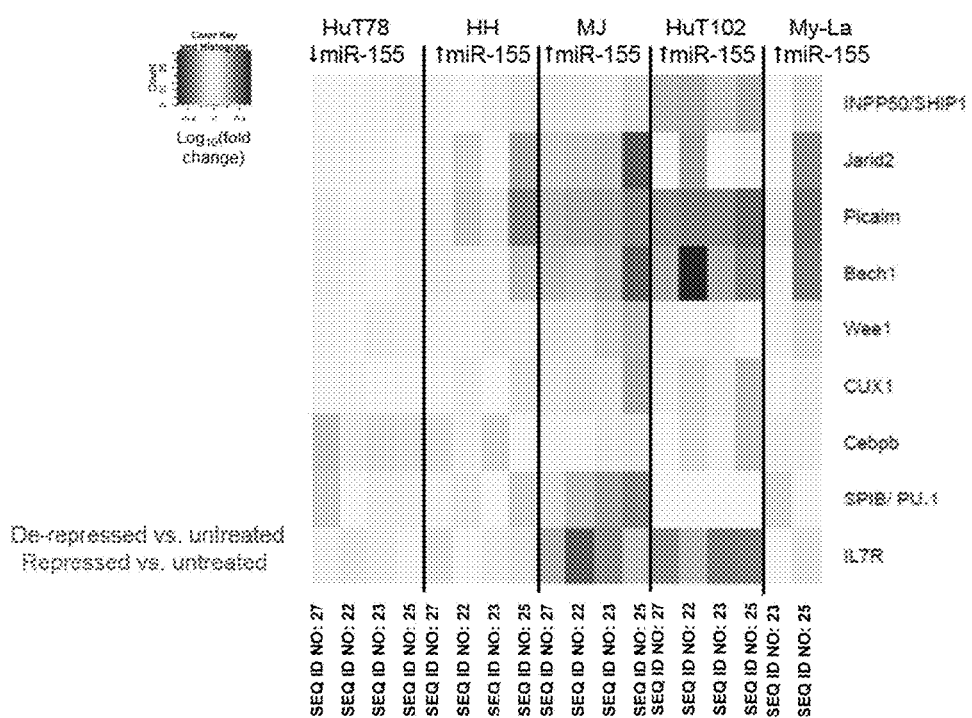
FIG. 2 shows a "heat map" representation of gene expression changes in 9 target genes of miR-155 in various CTCL cells in response to treatment with 10 µM of one of four antimiR-155 compounds for 72 hours.
Figure 6A:
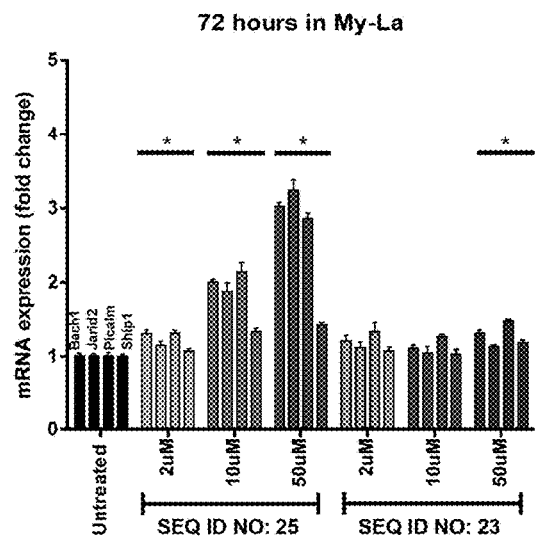
FIG. 6A shows a fold-change in the expression of four miR-155 target genes in response to treatment with 2, 10, and 50 μM antimiR-155 compounds for 72 hours in My-LA cells.
Figure 6B:
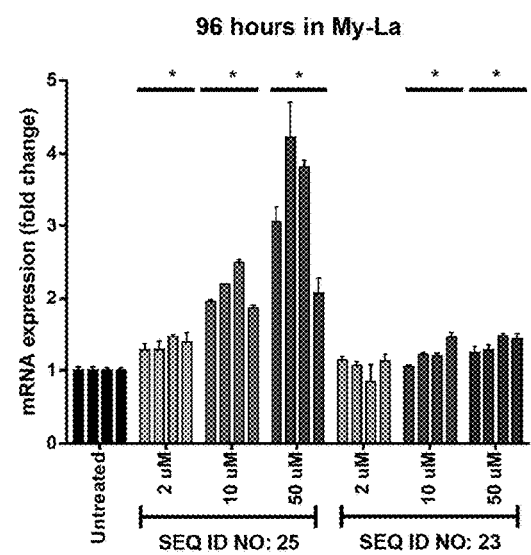
FIG. 6B shows a fold-change in the expression of four miR-155 target genes in response to treatment with 2, 10, and 50 μM antimiR-155 compounds for 96 hours in My-La cells. * p-value<0.0001 compared to untreated by nonparametric Mann-Whitney test.

CTCL cell lines were cultured in complete growth medium with the addition of antimiR-155 compound 1 (SEQ ID NO: 27), compound 2 (SEQ ID NO: 22), compound 3 (SEQ ID NO: 23), and compound 4 (SEQ ID NO: 25) at concentrations ranging from 2 µM to 50 µM. The antimiRs were added to the medium without any additional components to enhance cellular uptake. Cells were harvested after 72 hours of treatment and total RNA was purified. Real time PCR was performed for 13 direct gene targets of miR-155 (Worm et al. 2009; O'Connell et al. 2010; Zhang et al. 2012; and miRagen unpublished data). The relative fold-change in the expression of the 13 genes in the antimiR-treated cells compared to the untreated cells was calculated. FIG. 2 shows a "heat map" representation of gene expression changes in response to 72 hours of treatment with 10 µM of the indicated antimiR. Four predicted direct targets that lacked expression in at least one cell line were omitted. The gene expression fold-changes were log 10-transformed, plotted on a grayscale, representing the highest relative increase in gene expression, and conversely, the greatest reduction in gene expression. The heat map showed that the expression of several of the miR-155-5p target genes was modulated upon exposure to the miR-155-5p antagonists in three mycosis fungoides cell lines (MJ, HuT102, and My-La). Similar, but more modest gene expression changes were observed in the idiopathic cell line (HH) that expresses high levels of miR-155-5p. In contrast, expression of these genes was not significantly altered in the Sézary syndrome cell line (HuT78) that expresses low levels of miR-155-5p, indicating that the changes in the gene expression levels in mycosis fungoides cell lines and HH cell line are mediated by antagonism of miR-155-5p.

Example 2: AntimiR-155 Compounds 2 (SEQ ID NO: 22) and 4 (SEQ ID NO: 25) Show Greater Activity in Mycosis Fungoides Cells Lines Compared to Other antimiR Compounds Four direct gene targets of miR-155-5p (Bach1, Jarid2, Picalm, and Shipl) were chosen for additional analysis, as these four genes were modulated by antimiR-155 in all three mycosis fungoides cell lines (MJ, HuT102, and My-La). These genes were chosen to represent the gene expression signature for antimiR activity in vitro. Additionally, the four-gene signature was used to compare the activity of the antimiR compounds. These gene changes were reproducible over three independent experiments with cells of varying passage numbers. FIGS. 3, 4, 5, 6, and 7 show the fold-change results of this four-gene signature in the HuT102, MJ, HH, My-La, and Hut78 cell lines, respectively. * p-value<0.0001 vs untreated by nonparametric Mann-Whitney test. The Mann-Whitney test was chosen because the variances are unequal between the treatments compared to untreated cells.

The cumulative data across three doses (2 µM, 10 µM, and 50 µM) and three mycosis fungoides cell lines showed that compounds 2 (SEQ ID NO: 22) and 4 (SEQ ID NO: 25) were more active than compounds 1 (SEQ ID NO: 27) and 3 (SEQ ID NO: 23). As shown in FIG. 7, all four antimiR-155-5p compounds showed no statistically significant activity in the Sezary syndrome line (HuT78), which is consistent with the lower expression levels of miR-155 in this cell line as shown in FIG. 1.

Example 3: Gene Expression Changes Induced by antimiR-155 Treatment are Specific to the Inhibition of miR-155

Figure 8A:
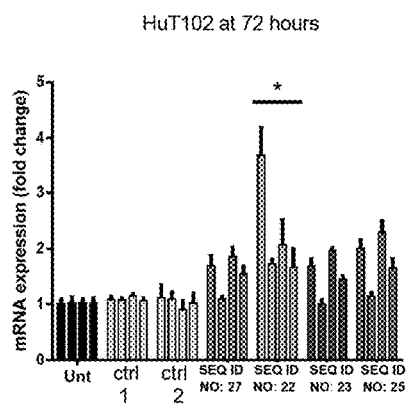
FIG. 8A shows a fold-change in the expression of four miR-155 target genes in response to treatment with 10 μM antimiR-155 compounds or control oligos in HuT102 cells.
Figure 8B:
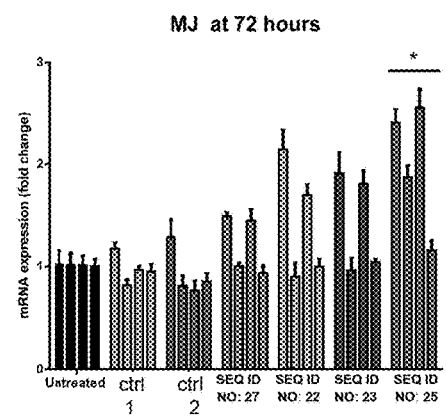
FIG. 8B shows a fold-change in the expression of four miR-155 target genes in response to treatment with 10 μM antimiR-155 compounds or control oligos in MJ cells. * p-value<0.0001 compared to untreated by nonparametric Mann-Whitney test.

To test the specificity of the gene expression changes induced by antimiR-155 compounds of the invention, mycosis fungoides cell lines were treated with oligos that do not target miR-155 (control oligos). The control oligonucleotide was a 14-nucleotide antimiR targeting a *C. elegans* miRNA not expressed in mammals (control 1). The second oligo is a scramble of the 14-nucleotide sequence of antimiR-155 compound 4 (control 2). The MJ and HuT102 cell lines were incubated with 10 µM antimiR-155 compounds 3 (SEQ ID NO: 23) or 4 (SEQ ID NO: 25) or the two control oligos for 72 hours. FIG. 8 shows the fold-change in gene expression for the four direct targets of miR-155-5p as measured by PCR. The gene expression signature in cells treated with antimiR-155 compounds 3 (SEQ ID NO: 23) or 4 (SEQ ID NO: 25) was statistically significantly different from that of untreated cells. In contrast, gene expression in cells treated with control compounds was not different from that of untreated cells. These results show that the miR-155 direct targets were de-repressed in response to the miR-155 inhibition, and not due to non-specific effects of oligo treatment. * p-value<0.0001 vs untreated by nonparametric Mann-Whitney test.

Example 4: Whole Genome Expression Profiling of CTCL Cell Lines Treated with antimiR-155 Confirm Target Engagement and Provide Mechanistic Insight To gain a more complete understanding of the molecular consequences of miR-155 inhibition in mycosis fungoides cell lines, whole genome transcriptome profiling was performed on MJ and HuT102 cell lines treated with antimiR-155 compounds 3 (SEQ ID NO: 23) or 4 (SEQ ID NO: 25) for 4 days (96 hours) or 8 days. The statistically-significant gene expression signature was defined by one-way ANOVA for antimiR-treated cells compared to untreated cells at the same time point. Data were filtered for genes that were significantly changed with a false discovery rate corrected p-value of ≤0.05. The fold-change results are shown in FIGS. 9 and 10 as heat maps, as described for FIG. 2.

Figure 9:
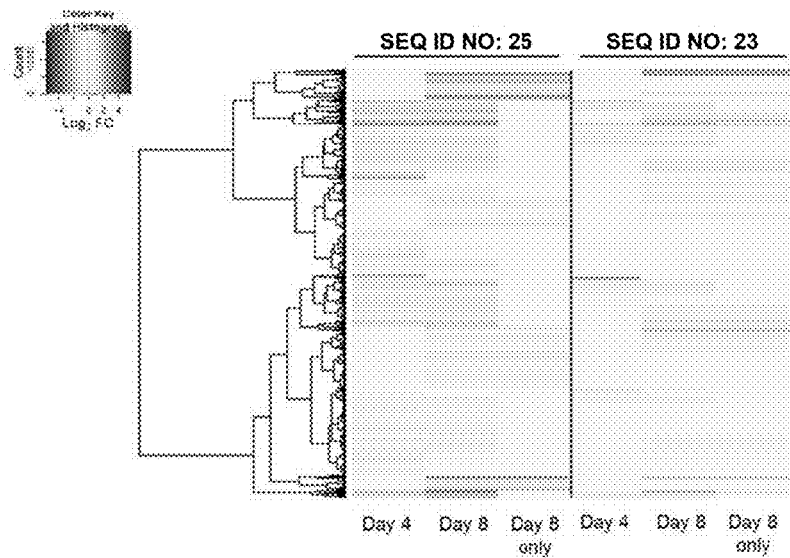
FIG. 9 shows a heat map of the differential gene expression signature in MJ cells treated with antimiR-155 compounds for 4 or 8 days. MJ cells treated with antimiR-155 were subjected to whole genome expression profiling. The differential expression signature was filtered for genes that were significantly changed with a false discovery rate corrected p-value of ≤0.05.
Figure 10:
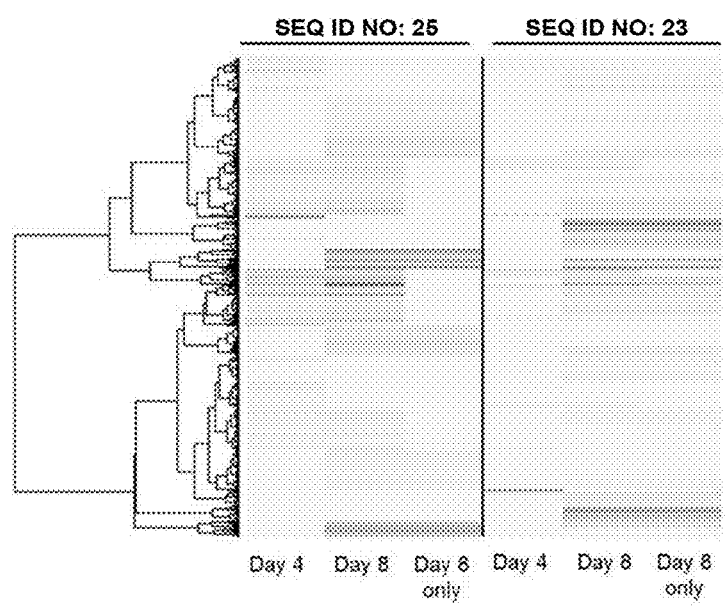
FIG. 10 shows a heat map of the differential gene expression signature in HuT102 cells treated with antimiR-155 compounds for 4 or 8 days. HuT102 cells treated with antimiR-155 were subjected to whole genome expression profiling. The differential expression signature was filtered for genes that were significantly changed with a false discovery rate corrected p-value of ≤0.05.

Examination of the global gene expression signatures at Day 4 and Day 8 suggested a time course for the gene expression changes in response to the antimiR-155 treatment: unique gene sets were identified that were regulated at the early time point (4 days), or at the late time point (8 days), as well as some genes that were changed at both time points (FIG. 9 for the MJ profile, FIG. 10 for the HuT102 profile). Furthermore, the expression profiling identified unique gene sets regulated in each cell line, as well as some genes regulated in both cell lines. Compound 4 (SEQ ID NO: 25) demonstrated a greater magnitude of gene regulation in both cell lines and at both time points, as demonstrated by the greater intensity across the Compound 4 (SEQ ID NO: 25) heat map.

Figure 11A:
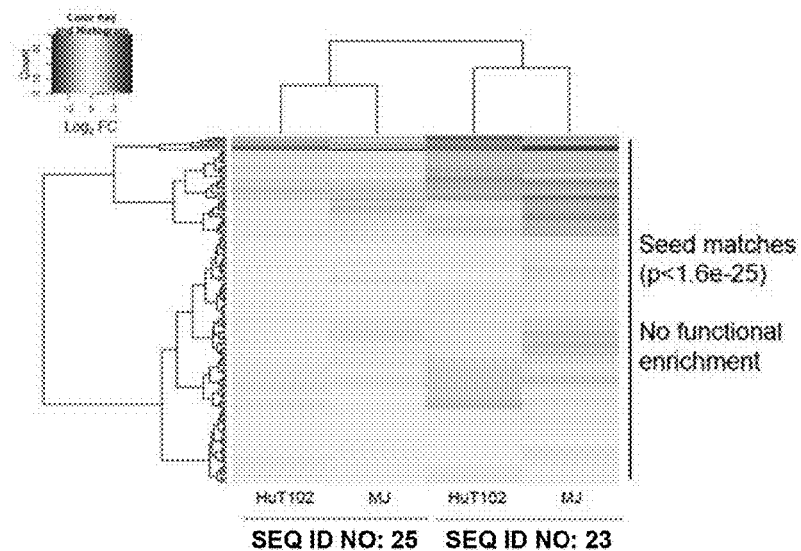
FIG. 11A shows the annotation of the gene expression profile of genes upregulated in response to antimiRs-155 in both MJ and HuT102 cells. The gene signature is enriched for miR-155 seed-matched direct targets with a hypergeometric p-value for enrichment of 1.6e-25. The genes identified here were significantly changed with antimiR-155 treatment compared to the untreated group with a false discovery rate corrected p-value of ≤0.05.
Figure 11B:
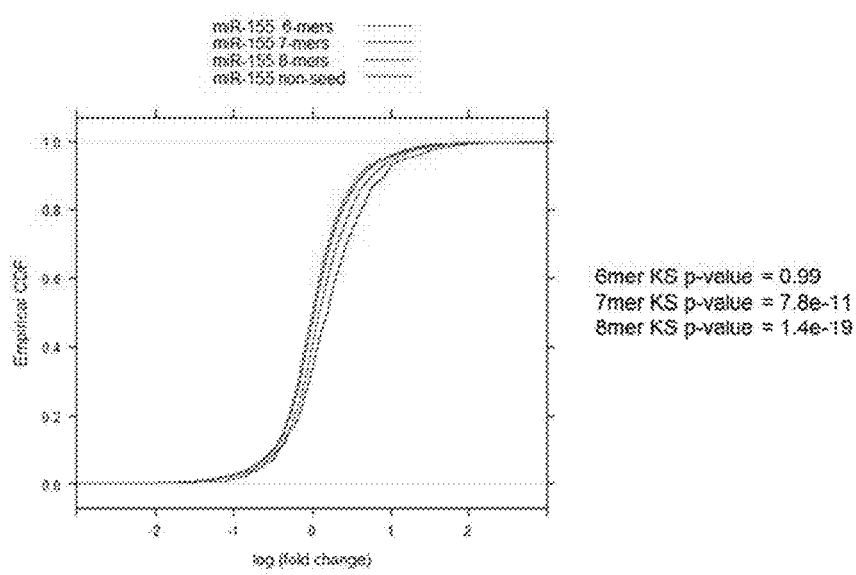
FIG. 11B shows a cumulative distribution function graph of the differential expression of miR-155 direct target genes containing 8-, 7-, or 6-nucleotide seeds sequences, compared to non-seed containing transcripts. The p-values shown are the result of the Kolmogorov-Smirnov test to determine the significant difference between two datasets.

The gene expression profile common to both cell lines and both compounds at Day 4 was analyzed for the enrichment of miR-155-5p seed-matched gene targets (8-, 7-, and 6-nucleotide binding sites). The fold-change of these genes is represented in a heat map in FIG. 11. This signature of 150 up-regulated genes was significantly enriched for miR-155-5p seed-matched targets (8-, 7-, and 6-nucleotide binding sites), with a hypergeometric p-value of $1.6 \times 10^{-25}$ (FIG. 11A). Analysis by cumulative distribution function confirmed enrichment for seed-matched targets, and demonstrated enrichment for 8mer>7mer>6mer binding sites (FIG. 11B). The gene signature was also analyzed using the DAVID bioinformatic resource for functional gene annotation enrichment (Huang da et al., 2009). There was no significant enrichment of Gene Ontology database terms as defined by a Benjamini-corrected p-value of ≤0.01.

Figure 12:
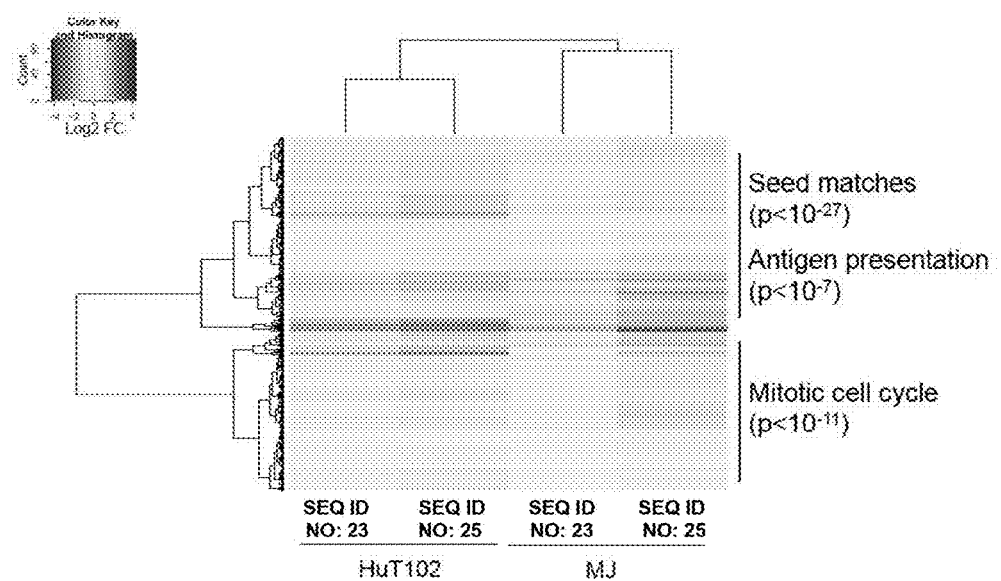
FIG. 12 shows an annotated gene expression profile of genes up-regulated or down-regulated in response to treatment with antimiR-155 compounds for 8 days in both MJ and HuT102 cells.

The gene expression signature common to both cell lines and both compounds at Day 8 (677 genes in total) was subjected to analysis for enrichment of seed-matched gene targets and for functional gene annotation. The up-regulated gene signature was significantly enriched for seed-matched targets with a hypergeometric p-value of $<10^{-27}$. Unlike the Day 4 signature, the Day 8 signature also showed strong enrichment of two functional annotation terms: antigen presentation in the up-regulated signature, and mitotic cell cycle in the down-regulated signature (FIG. 12). Together, these results confirm that the effect of the antimiR compounds is mediated by the inhibition of miR-155-5p and its direct gene targets, and that phenotypes elicited by the inhibition of miR-155-5p function may include enhanced antigen presentation and reduction in proliferation.

Figure 13:
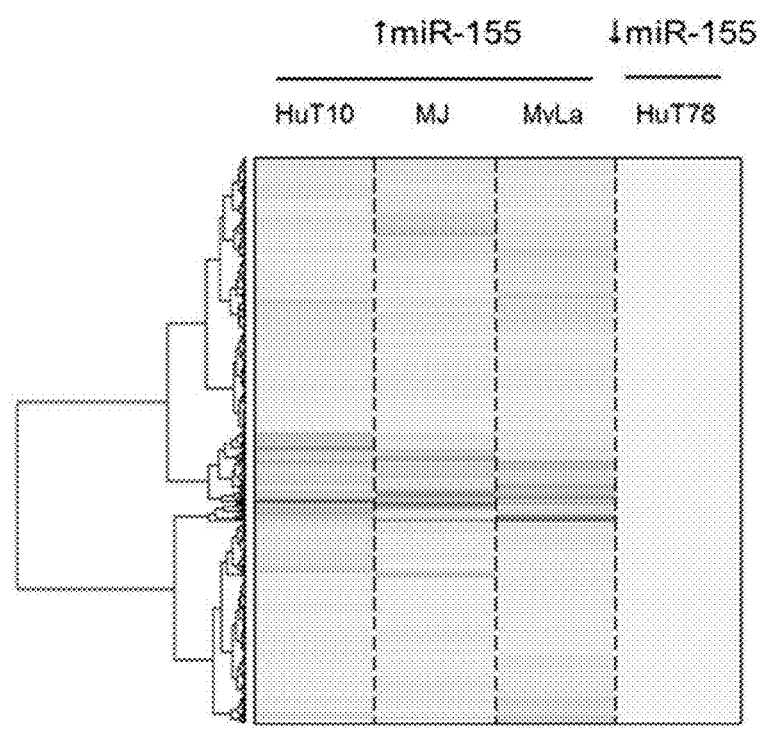
FIG. 13 shows an expression profile of genes upregulated or downregulated in response to 8 days of treatment with the antimiR-155 having a sequence of SEQ ID NO: 25 in CTCL cells.

The activity of antimiR-155 compound 4 (SEQ ID NO: 25) was further investigated by treating the third mycosis fungoides cell line, MyLa, with compound 4 (SEQ ID NO: 25) for 4 days and 8 days and profiling the changes in gene expression. To test the specificity of compound 4 (SEQ ID NO: 25), cells of the Sézary syndrome cell line (HuT78) were treated with compound 4 (SEQ ID NO: 25) for 8 days and the changes in gene expression were profiled. These results are shown in FIG. 13. Genes that are statistically changed with a false discovery rate (FDR) corrected p-value of <0.05 in response to compound 4 (SEQ ID NO: 25) in three mycosis fungoides cell lines, HuT102, MJ, and My-La, are depicted in the heat map as described above. The total number of genes in the heat map is 324. FIG. 13 shows that the treatment of Sézary syndrome cell line HuT78 with compound 4 (SEQ ID NO: 25) did not show much change in the gene expression indicating that the gene expression changes in mycosis fungoides cell lines are indeed due to the inhibition of miR-155-5p by compound 4 (SEQ ID NO: 25).

Figure 21:
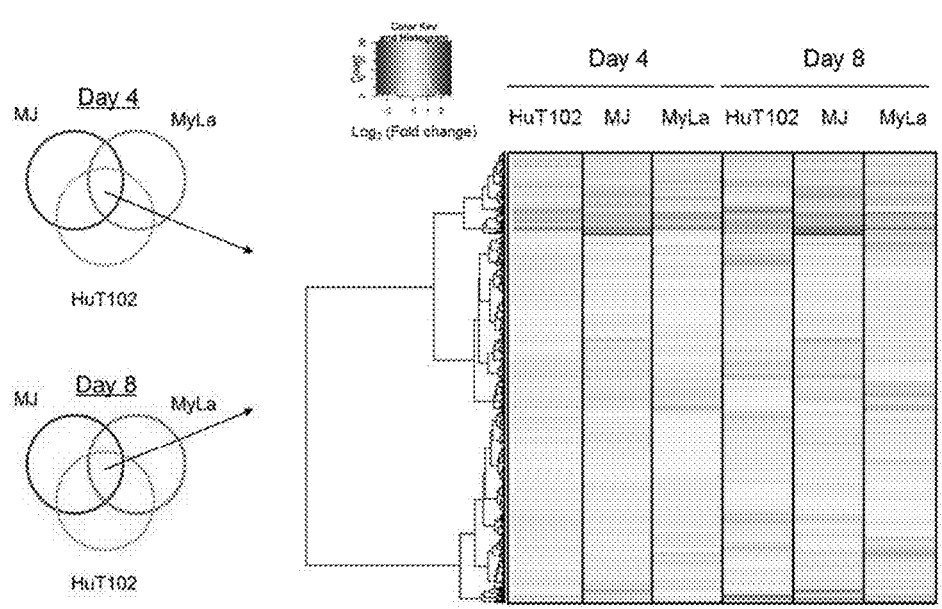
FIG. 21 shows a heat map of expression changes in 587 genes up-regulated or down-regulated in all three mycosis fungoides cell lines at day 4 or day 8 in response to compound 4 (SEQ ID NO: 25).

Additionally, genes regulated by compound 4 (SEQ ID NO: 25) in all three mycosis fungoides cell lines were identified as a biomarker signature that could be used for clinical assessment of treatment with antimiR-155 compounds, such as compound 4 (SEQ ID NO: 25), of the invention. The identified set of genes was up-regulated in all three cell lines or down-regulated in all three cell lines. Common signatures for each time point (Day 4 and Day 8) were identified and then combined into a single gene list (Table 2). No filter was placed on the magnitude of gene expression. Therefore, Table 2 contains genes that are regulated only at Day 4, or only at Day 8, or regulated at both time points. Table 2 contains 587 genes comprising early (direct) targets and downstream (indirect) targets regulated by compound 4 (SEQ ID NO: 25) (FIG. 21). The gene list in Table 2 includes the direct targets Bach1, Picalm, and Jarid2, demonstrating that these genes are robust markers of the compound 4 (SEQ ID NO: 25) activity across multiple cell lines and time points.

Example 5: AntimiR-155 Compounds of the Invention Inhibits Cell Proliferation and Increases Apoptosis in CTCL Cells Passive uptake of antimiR-155 compounds by CTCL cells produced a significant reduction in cellular proliferation and induced programmed cell death. These effects were observed in two CTCL cell lines, HuT102 and MyLa. AntimiR-155 compounds 2 (SEQ ID NO: 22) and 4 (SEQ ID NO: 25) that demonstrated a greater target de-repression than antimiR-155 compound 3 (SEQ ID NO: 23) in both HuT102 and MyLa cell lines, showed a greater inhibition of proliferation and greater apoptotic activity.

Figure 14A:
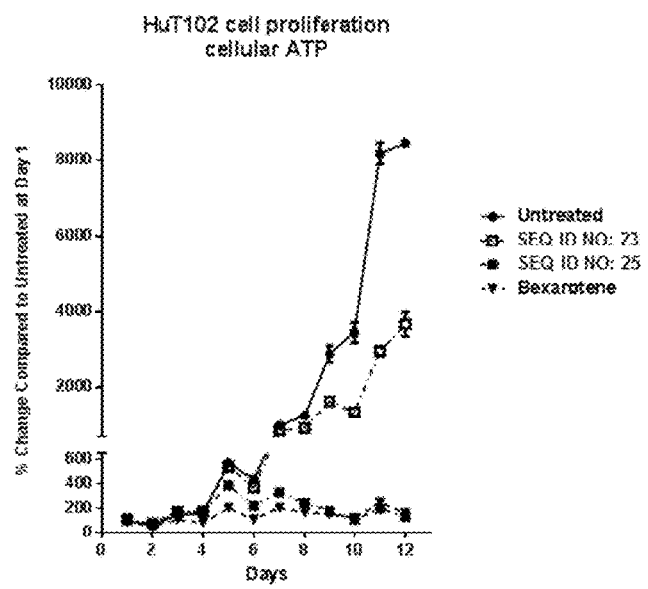
FIG. 14A shows the effect of antimiR-155 compounds on proliferation of HuT102 cells.
Figure 14B:
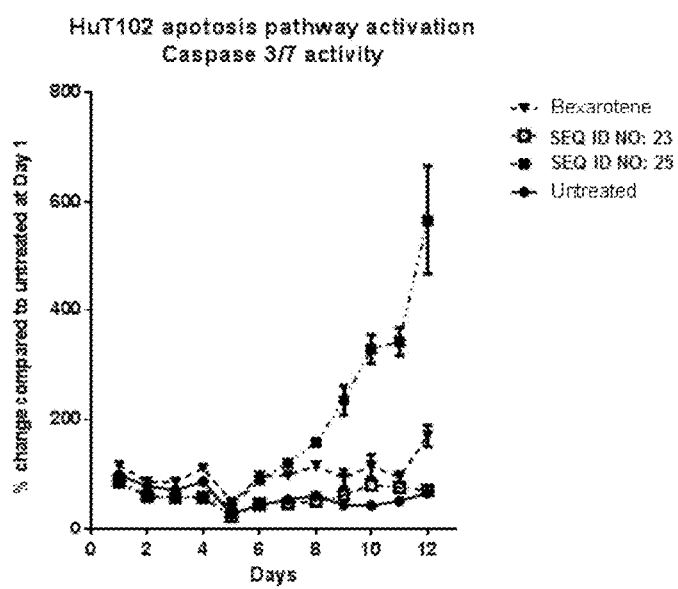
FIG. 14B shows the effect of antimiR-155 compounds on caspase 3/7 activity in HuT102 cells.

FIG. 14A shows the effect of antimiR-155 compound 4 (SEQ ID NO: 25) on proliferation of HuT-102 cells over time. Since the level of ATP correlates directly with cell number, ATP was measured to determine the cell number. The effect of compound 4 (SEQ ID NO: 25) on cell number was comparable to that seen with bexarotene, a standard-of-care therapy for CTCL (FIG. 14A). The reduction in cell number was accompanied by an increase in apoptosis as measured by caspase 3/7 activity (FIG. 14B). The caspase 3 and 7 proteins are members of the cysteine aspartic acid-specific protease (caspase) family. The caspase family plays key effector roles in apoptosis in mammalian cells. Caspase activity was normalized to ATP levels, as all cells have a low level of basal caspase activity that can confound the results if not normalized appropriately. Compound 4 (SEQ ID NO: 25) showed greater induction of apoptosis than bexarotene (FIG. 14B).

Figure 15A:
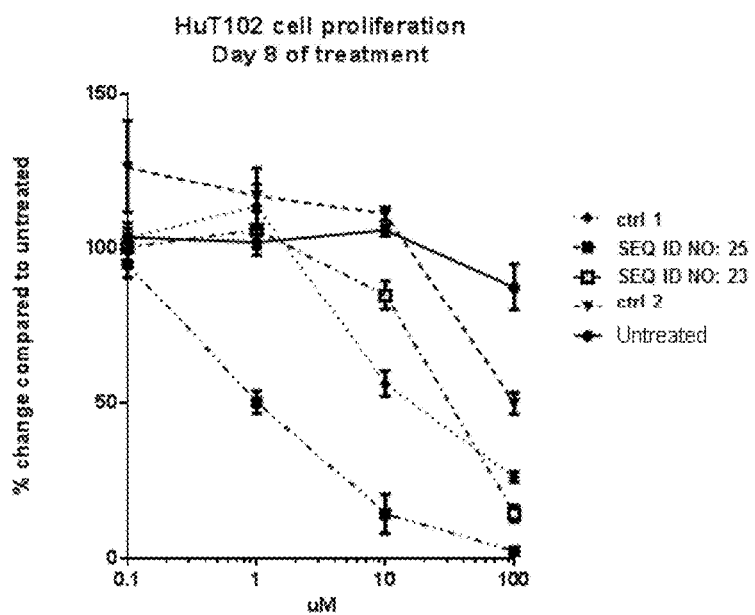
FIG. 15A shows proliferation of HuT102 cells in response to various concentrations of antimiR-155 compounds at day 8 of treatment.
Figure 15B:
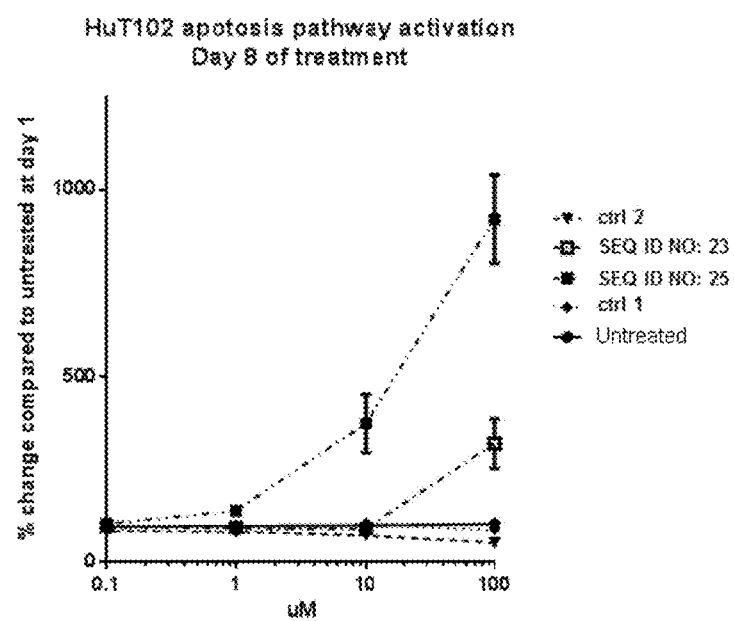
FIG. 15B shows caspase 3/7 activity in HuT102 cells in response to various concentrations of antimiR-155 compounds at day 8 of treatment.

In addition to a time course, a dose titration of antimiR-155 compounds in HuT102 cells was performed with ATP and caspase 3/7 measurements performed after eight days of treatment (FIGS. 15A and 15B, respectively). These results confirm the inhibitory potential of compound 4 (SEQ ID NO: 25).

Figure 16A:
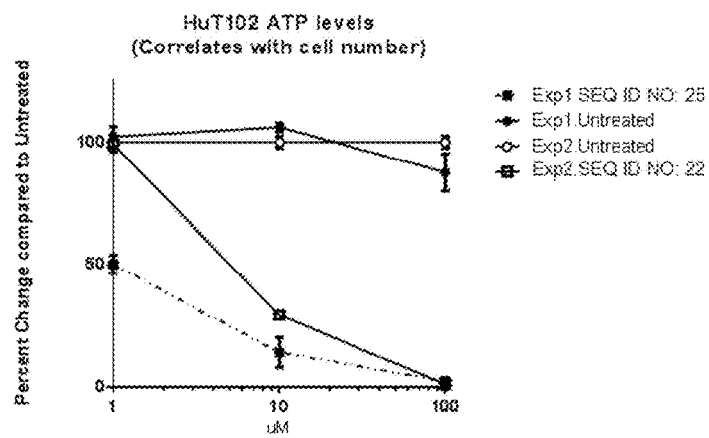
FIG. 16A shows the effect of antimiR-155 compounds on proliferation of HuT102 cells.
Figure 16B:
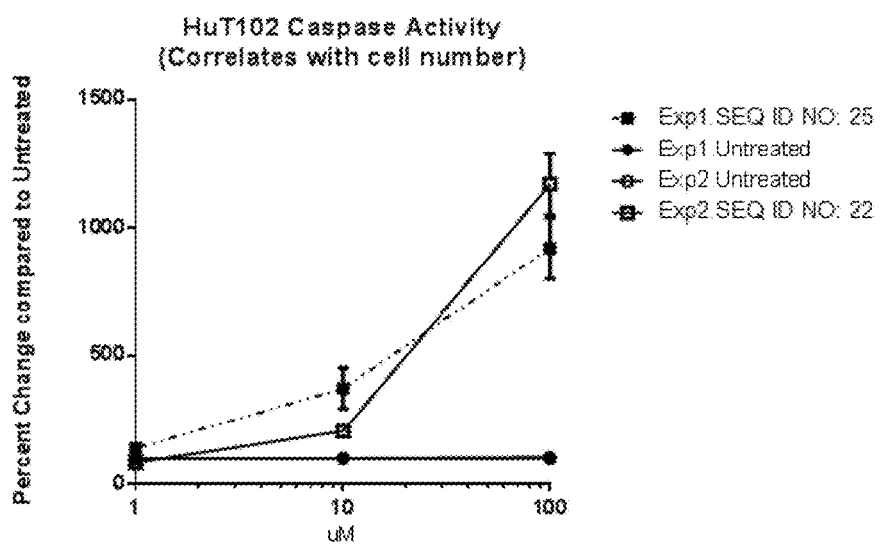
FIG. 16B shows the effect of antimiR-155 compounds on caspase 3/7 activity in HuT102 cells.

Similar effects on proliferation and caspase 3/7 activation were observed with antimiR-155 compound 2 (SEQ ID NO: 22) at day 8 in HuT-102 cells (FIGS. 16A and 16B, respectively).

Figure 17A:
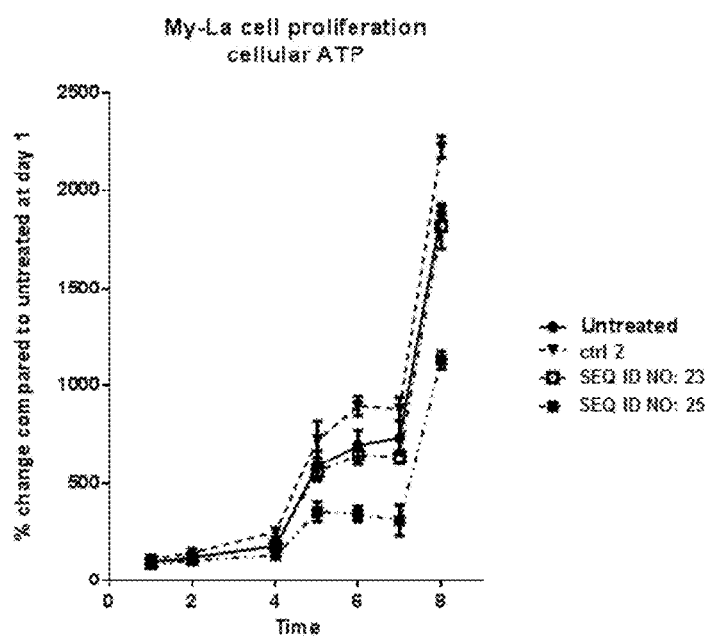
FIG. 17A shows the effect of antimiR-155 compounds on proliferation of My-La cells.
Figure 17B:
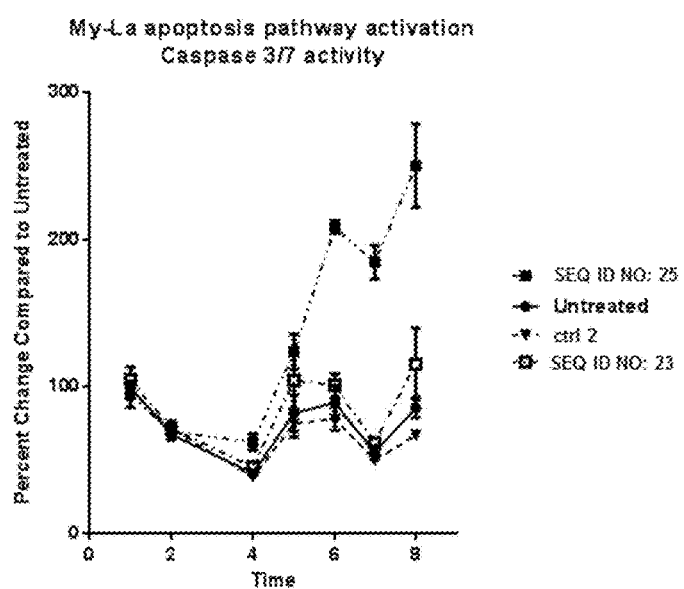
FIG. 17B shows the effect of antimiR-155 compounds on caspase 3/7 activity in My-La cells.

Compound 4 (SEQ ID NO: 25) showed similar activity in a second mycosis fungoides cell line, My-La cells. FIGS. 17A and 17B show proliferation and activation of caspase 3/7 over time with compounds 3 (SEQ ID NO: 23) and 4 (SEQ ID NO: 25). Similar to HuT102 cells, compound 4 (SEQ ID NO: 25) showed greater activity compared to compound 3 (SEQ ID NO: 23).

Figure 18A:
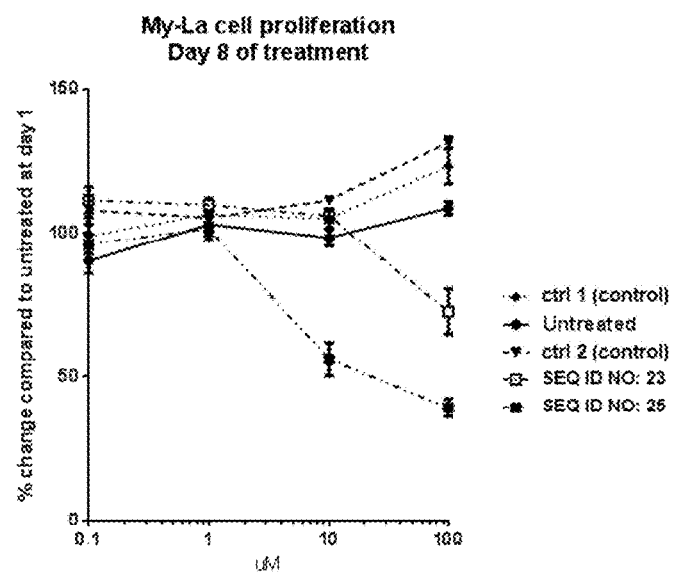
FIG. 18A shows proliferation of My-La cells in response to various concentrations of antimiR-155 compounds at day 8 of treatment.
Figure 18B:
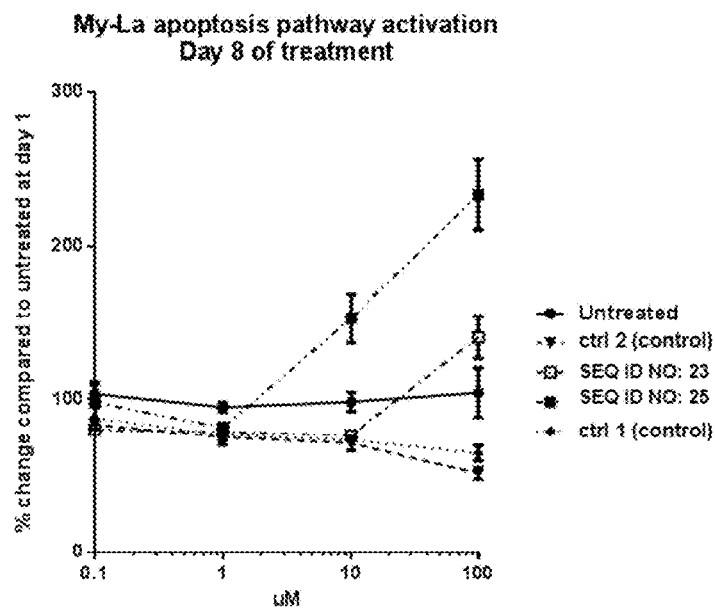
FIG. 18B shows caspase 3/7 activity in My-La cells in response to various concentrations of antimiR-155 compounds at day 8 of treatment.

In addition to a time course, a dose titration of antimiR-155 compounds in My-La cells was performed with ATP and caspase 3/7 measurements after eight days of treatment (FIGS. 18A and 18B, respectively). These results further confirm the inhibitory potential of compound 4 (SEQ ID NO: 25).

Example 6: AntimiR-155 Treatment Combined with an HDAC Inhibitor Enhances the Effect on Cell Proliferation and Apoptosis Activity Vorinostat (chemical name: SAHA) is a standard-of-care epigenetic therapy for patients with advanced mycosis fungoides. However, the side-effects of pan-HDAC inhibitors are well-described. To determine whether a combination therapy might show enhanced activity compared to treatment with individual compounds, HuT102 cells were treated with a sub-efficacious dose of SAHA combined with anti-miR-155.

Figure 19A:
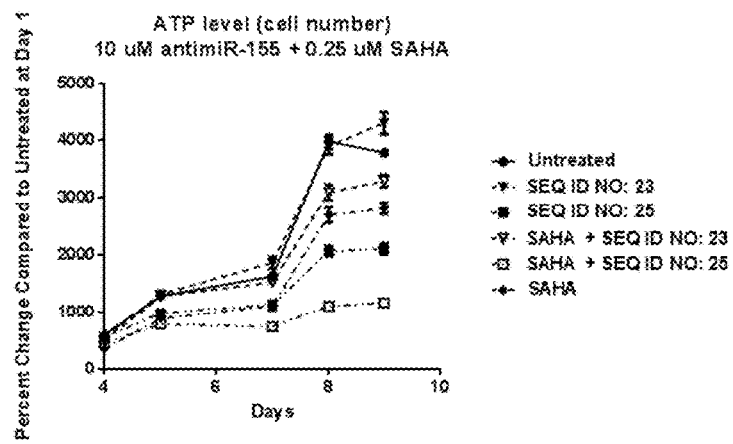
FIG. 19A shows the effect of 10 μM antimiR-155 compounds and 0.25 μM HDAC inhibitor on proliferation of HuT102 cells.
Figure 19B:
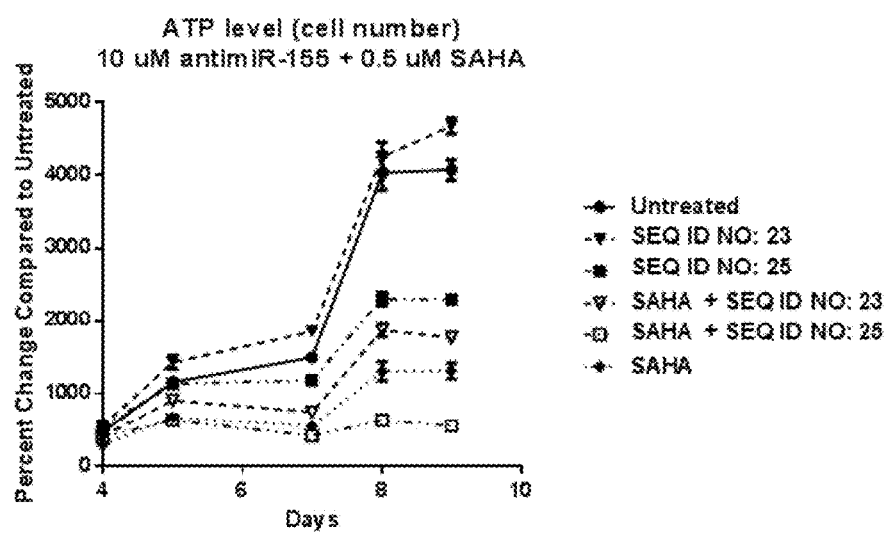
FIG. 19B shows the effect of 10 μM antimiR-155 compounds and 0.50 μM HDAC inhibitor on proliferation of HuT102 cells.

HuT102 cells were treated with 0.25 µM SAHA and 10 µM compound 3 (SEQ ID NO: 23) or 4 (SEQ ID NO: 25), individually or in combination. Cells were harvested daily to measure ATP levels and caspase 3/7 activity. ATP levels are shown in FIG. 19A. A similar experiment was performed with 0.50 µM SAHA. FIG. 19B shows ATP levels obtained when HuT102 cells were treated with 0.50 µM SAHA and 10 µM compound 3 (SEQ ID NO: 23) or 4 (SEQ ID NO: 25), individually or in combination.

Figure 20A:
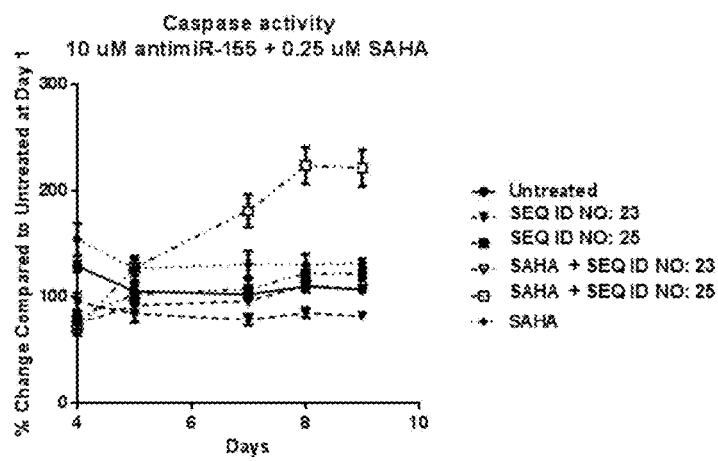
FIG. 20A shows the effect of 10 μM antimiR-155 compounds and 0.25 μM HDAC inhibitor on caspase 3/7 activity in HuT102 cells.
Figure 20B:
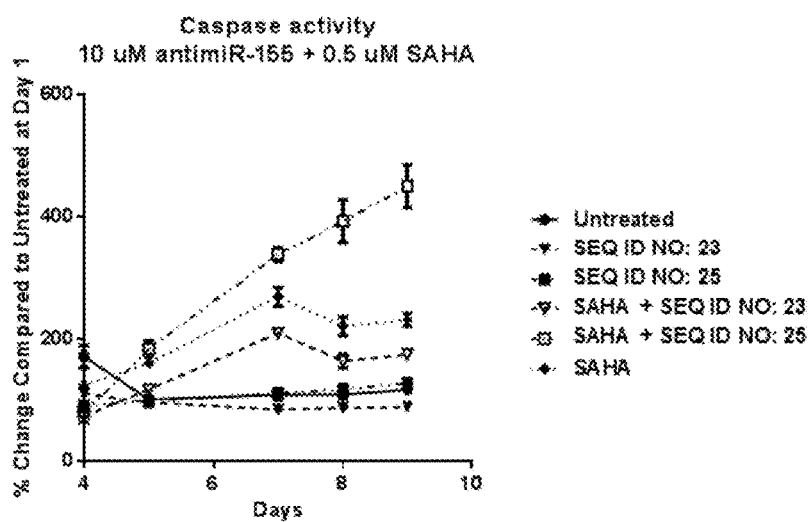
FIG. 20B shows the effect of 10 μM antimiR-155 compounds and 0.50 μM HDAC inhibitor on caspase 3/7 activity in HuT102 cells.

FIGS. 20A and 20B show the effect on caspase 3/7 activity. Compound 4 (SEQ ID NO: 25) when combined with 0.25 or 0.5 µM of SAHA resulted in increased apoptosis compared to each treatment alone. This data suggests that antimiR-155 oligos can be used in combination with low doses pan-HDAC inhibitor.

Example 7: AntimiR-155 Activity of Oligonucleotides of Different Lengths

To assess the activity of a miR-155 inhibitor, a dual luciferase reporter assay system was used. In brief, the binding site for miR-155 was cloned into the 3' UTR of the *Renilla* luciferase gene located within the commercially-available psiCHECK-2 vector system (Promega). In the absence of a miR-155 inhibitor, the expression of *Renilla* luciferase protein is repressed by a miR-155 mimic. In the presence of a miR-155 inhibitor, the expression of *Renilla* luciferase protein is de-repressed. To control for transfection of the plasmid, the vector contains a firefly luciferase gene that does not contain the miR-155 binding site. Expression of either *Renilla* or firefly luciferase is measured through detection of light emitted by the luciferase protein.

50 ng of the dual luciferase reporter plasmid containing the miR-155 binding site was transfected into HeLa cells without a miR-155 mimic ("Reporter" only), with 10 nM miR-155 mimic ("Reporter+mimic"), with 10 nM miR-155 mimic and 2 nM of the control oligonucleotide, or with 10 nM miR-155 mimic and 2 nM of a test miR-155 oligonucleotide inhibitor of 11-14 nucleotide lengths (Table 4). The miR-155 mimic was purchased from Dharmacon (miRIDIAN microRNA Human hsa-miR-155-5p mimic; Accession number MIMAT0000646; catalog # C-300647-05-0005) and contains the mature miRNA sequence: -UUAAUGC-UAAUCGUGAUAGGGGU- (SEQ ID NO: 121). The control oligonucleotide used in the experiment had the following sequence: 5'-1Cs.dTs.dAs.1Gs.dAs.1As.dAs.1Gs1As.dGs.1Ts.dAs.1Gs.1A-3' (SEQ ID NO: 122).

TABLE 4

| SEQ ID NO. | Modified Sequence | LNA # | Length |
|---|---|---|---|
| 25 | 5'-1Cs;dAs;1Cs;dGs;dAs;1Ts;1Ts;dAs;1Gs;dCs;1As;1Ts;1Ts;1A-3' | 9 | 14 |
| 54 | 5'-1As;1Cs;dGs;dAs;1Ts;1Ts;dAs;1Gs;dCs;1As;1Ts;1Ts;1A-3' | 9 | 13 |
| 55 | 5'-1Cs;dGs;dAs;1Ts;1Ts;dAs;1Gs;dCs;1As;1Ts;1Ts;1A-3' | 8 | 12 |
| 56 | 5'-1Gs;dAs;1Ts;1Ts;dAs;1Gs;dCs;1As;1Ts;1Ts;1A-3' | 8 | 11 |

Figure 22:
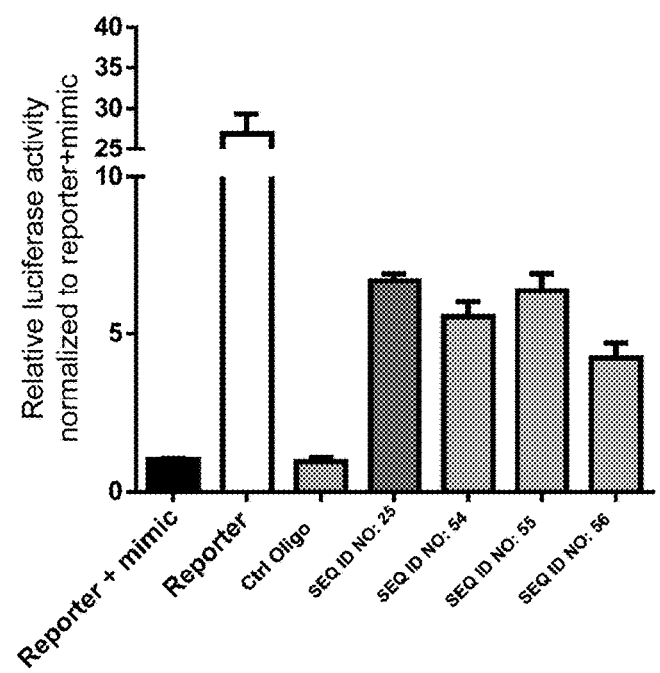
FIG. 22 shows the antimiR-155 activity of oligonucleotide inhibitors of different lengths measured using a dual luciferase reporter plasmid containing the miR-155 binding site.

FIG. 22 shows that transfection of the reporter plasmid and the mimic resulted in the maximal repression of luciferase; transfection of the reporter plasmid alone resulted in the maximum expression of luciferase; transfection of the control oligonucleotide with the reporter and the mimic did not de-repress the expression of luciferase; and transfection of the test miR-155 oligonucleotide inhibitors with the reporter and the mimic de-repressed the expression of luciferase to differing extents.

Example 8: AntimiR-155 Activity of Oligonucleotides Containing Varying Number of Locked Nucleotides (LNAs)

Figure 23A:
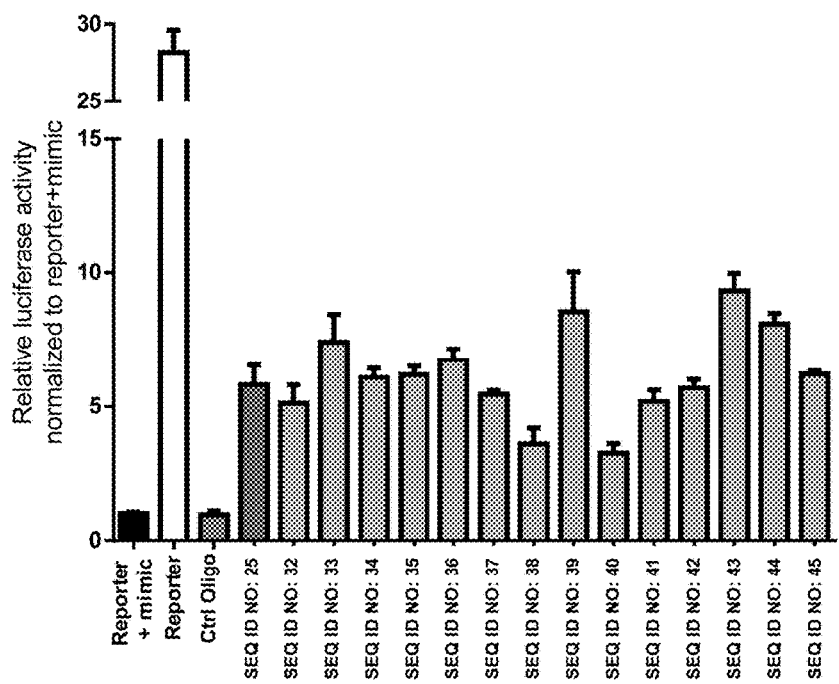
FIGS. 23A, 23B, 23C, and 23D show the antimiR-155 activity of oligonucleotide inhibitors containing varying number of locked nucleotide modifications measured using a dual luciferase reporter plasmid containing the miR-155 binding site.
Figure 23B:
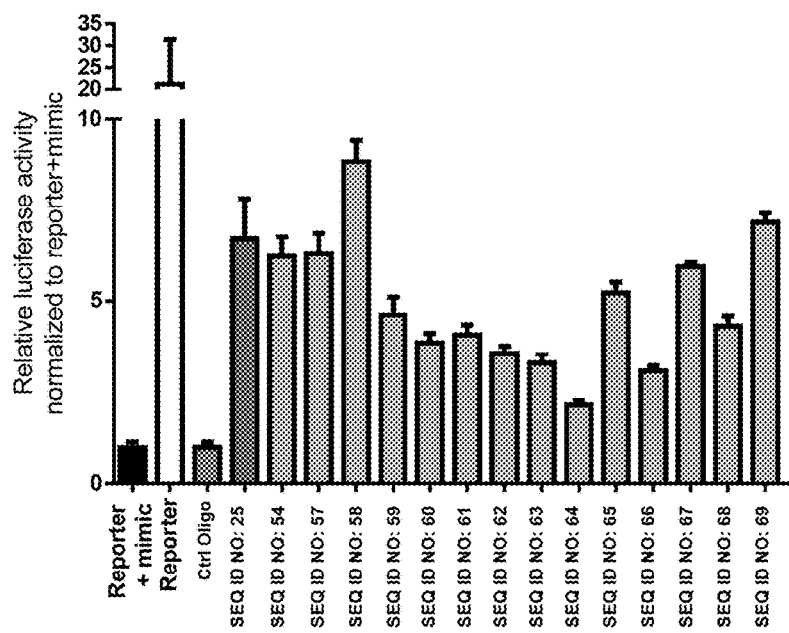
Figure 23C:
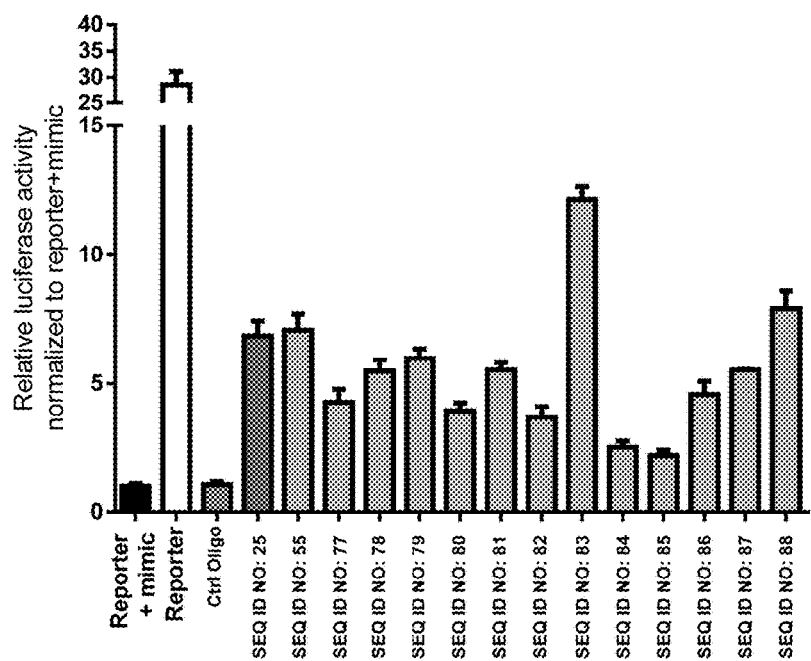
Figure 23D:
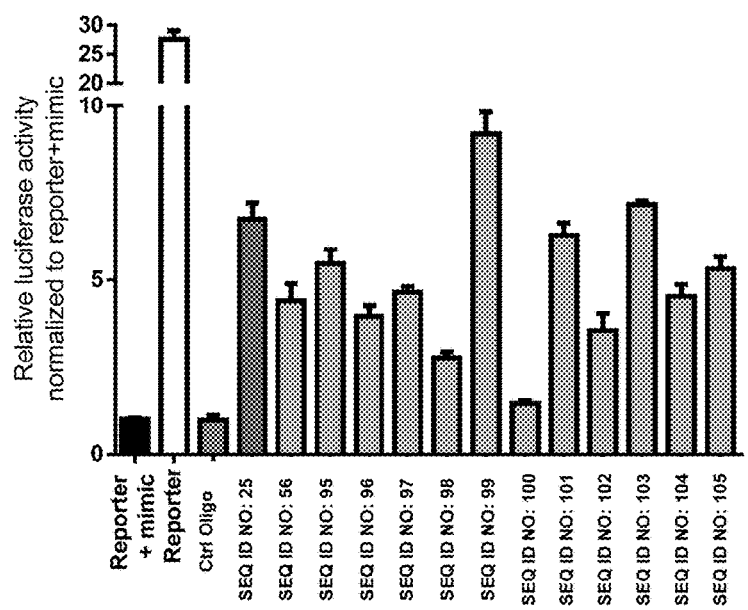

The experiment was performed as described in Example 7. Test miR-155 oligonucleotide inhibitors used in this experiment differed in the number of LNAs contained (Tables 5-8). The results are shown in FIGS. 23A (Table 5), 23B (Table 6), 23C (Table 7), and 23D (Table 8).

TABLE 5

| SEQ ID NO. | Modified Sequence | LNA # | Length |
|---|---|---|---|
| 25 | 5'-lCs;dAs;lCs;dGs;dAs;lTs;lTs;dAs;lGs;dCs;lAs;lTs;lTs;lA-3' | 9 | 14 |
| 32 | 5'-dCs;dAs;lCs;dGs;dAs;lTs;lTs;dAs;lGs;dCs;lAs;lTs;lTs;lA-3' | 8 | 14 |
| 33 | 5'-lCs;lAs;lCs;dGs;dAs;lTs;lTs;dAs;lGs;dCs;lAs;lTs;lTs;lA-3' | 10 | 14 |
| 34 | 5'-lCs;dAs;dCs;dGs;dAs;lTs;lTs;dAs;lGs;dCs;lAs;lTs;lTs;lA-3' | 8 | 14 |
| 35 | 5'-lCs;dAs;lCs;lGs;dAs;lTs;lTs;dAs;lGs;dCs;lAs;lTs;lTs;lA-3' | 10 | 14 |
| 36 | 5'-lCs;dAs;lCs;dGs;lAs;lTs;lTs;dAs;lGs;dCs;lAs;lTs;lTs;lA-3' | 10 | 14 |
| 37 | 5'-lCs;dAs;lCs;dGs;dAs;dTs;lTs;dAs;lGs;dCs;lAs;lTs;lTs;lA-3' | 8 | 14 |
| 38 | 5'-lCs;dAs;lCs;dGs;dAs;lTs;dTs;dAs;lGs;dCs;lAs;lTs;lTs;lA-3' | 8 | 14 |
| 39 | 5'-lCs;dAs;lCs;dGs;dAs;lTs;lTs;lAs;lGs;dCs;lAs;lTs;lTs;lA-3' | 10 | 14 |
| 40 | 5'-lCs;dAs;lCs;dGs;dAs;lTs;lTs;dAs;dGs;dCs;lAs;lTs;lTs;lA-3' | 8 | 14 |
| 41 | 5'-lCs;dAs;lCs;dGs;dAs;lTs;lTs;dAs;lGs;lCs;lAs;lTs;lTs;lA-3' | 10 | 14 |
| 42 | 5'-lCs;dAs;lCs;dGs;dAs;lTs;lTs;dAs;lGs;dCs;dAs;lTs;lTs;lA-3' | 8 | 14 |
| 43 | 5'-lCs;dAs;lCs;dGs;dAs;lTs;lTs;dAs;lGs;dCs;lAs;dTs;lTs;lA-3' | 8 | 14 |
| 44 | 5'-lCs;dAs;lCs;dGs;dAs;lTs;lTs;dAs;lGs;dCs;lAs;lTs;dTs;lA-3' | 8 | 14 |
| 45 | 5'-lCs;dAs;lCs;dGs;dAs;lTs;lTs;dAs;lGs;dCs;lAs;lTs;lTs;dA-3' | 8 | 14 |

TABLE 6

| SEQ ID NO. | Modified Sequence | LNA # | Length |
|---|---|---|---|
| 25 | 5'-lCs;dAs;lCs;dGs;dAs;lTs;lTs;dAs;lGs;dCs;lAs;lTs;lTs;lA-3' | 9 | 14 |
| 54 | 5'-lAs;lCs;dGs;dAs;lTs;lTs;dAs;lGs;dCs;lAs;lTs;lTs;lA-3' | 9 | 13 |
| 57 | 5'-dAs;lCs;dGs;dAs;lTs;lTs;dAs;lGs;dCs;lAs;lTs;lTs;lA-3' | 8 | 13 |
| 58 | 5'-lAs;dCs;dGs;dAs;lTs;lTs;dAs;lGs;dCs;lAs;lTs;lTs;lA-3' | 8 | 13 |
| 59 | 5'-lAs;lCs;lGs;dAs;lTs;lTs;dAs;lGs;dCs;lAs;lTs;lTs;lA-3' | 10 | 13 |
| 60 | 5'-lAs;lCs;dGs;lAs;lTs;lTs;dAs;lGs;dCs;lAs;lTs;lTs;lA-3' | 10 | 13 |
| 61 | 5'-lAs;lCs;dGs;dAs;dTs;lTs;dAs;lGs;dCs;lAs;lTs;lTs;lA-3' | 8 | 13 |
| 62 | 5'-lAs;lCs;dGs;dAs;lTs;dTs;dAs;lGs;dCs;lAs;lTs;lTs;lA-3' | 8 | 13 |
| 63 | 5'-lAs;lCs;dGs;dAs;lTs;lTs;lAs;lGs;dCs;lAs;lTs;lTs;lA-3' | 10 | 13 |
| 64 | 5'-lAs;lCs;dGs;dAs;lTs;lTs;dAs;dGs;dCs;lAs;lTs;lTs;lA-3' | 8 | 13 |
| 65 | 5'-lAs;lCs;dGs;dAs;lTs;lTs;dAs;lGs;lCs;lAs;lTs;lTs;lA-3' | 10 | 13 |
| 66 | 5'-lAs;lCs;dGs;dAs;lTs;lTs;dAs;lGs;dCs;dAs;lTs;lTs;lA-3' | 8 | 13 |
| 67 | 5'-lAs;lCs;dGs;dAs;lTs;lTs;dAs;lGs;dCs;lAs;dTs;lTs;lA-3' | 8 | 13 |
| 68 | 5'-lAs;lCs;dGs;dAs;lTs;lTs;dAs;lGs;dCs;lAs;lTs;dTs;lA-3' | 8 | 13 |
| 69 | 5'-lAs;lCs;dGs;dAs;lTs;lTs;dAs;lGs;dCs;lAs;lTs;lTs;dA-3' | 8 | 13 |

TABLE 7

| SEQ ID NO. | Modified Sequence | LNA # | Length |
|---|---|---|---|
| 25 | 5'-lCs;dAs;lCs;dGs;dAs;lTs;lTs;dAs;lGs;dCs;lAs;lTs;lTs;lA-3' | 9 | 14 |
| 55 | 5'-lCs;dGs;dAs;lTs;lTs;dAs;lGs;dCs;lAs;lTs;lTs;lA-3' | 8 | 12 |
| 77 | 5'-dCs;dGs;dAs;lTs;lTs;dAs;lGs;dCs;lAs;lTs;lTs;lA-3' | 7 | 12 |
| 78 | 5'-lCs;lGs;dAs;lTs;lTs;dAs;lGs;dCs;lAs;lTs;lTs;lA-3' | 9 | 12 |
| 79 | 5'-lCs;dGs;lAs;lTs;lTs;dAs;lGs;dCs;lAs;lTs;lTs;lA-3' | 9 | 12 |
| 80 | 5'-lCs;dGs;dAs;dTs;lTs;dAs;lGs;dCs;lAs;lTs;lTs;lA-3' | 7 | 12 |
| 81 | 5'-lCs;dGs;dAs;lTs;dTs;dAs;lGs;dCs;lAs;lTs;lTs;lA-3' | 7 | 12 |
| 82 | 5'-lCs;dGs;dAs;lTs;lTs;lAs;lGs;dCs;lAs;lTs;lTs;lA-3' | 9 | 12 |
| 83 | 5'-lCs;dGs;dAs;lTs;lTs;dAs;dGs;dCs;lAs;lTs;lTs;lA-3' | 7 | 12 |
| 84 | 5'-lCs;dGs;dAs;lTs;lTs;dAs;lGs;lCs;lAs;lTs;lTs;lA-3' | 9 | 12 |
| 85 | 5'-lCs;dGs;dAs;lTs;lTs;dAs;lGs;dCs;dAs;lTs;lTs;lA-3' | 7 | 12 |
| 86 | 5'-lCs;dGs;dAs;lTs;lTs;dAs;lGs;dCs;lAs;dTs;lTs;lA-3' | 7 | 12 |
| 87 | 5'-lCs;dGs;dAs;lTs;lTs;dAs;lGs;dCs;lAs;lTs;dTs;lA-3' | 7 | 12 |
| 88 | 5'-lCs;dGs;dAs;lTs;lTs;dAs;lGs;dCs;lAs;lTs;lTs;dA-3' | 7 | 12 |

TABLE 8

| SEQ ID NO. | Modified Sequence | LNA # | Length |
|---|---|---|---|
| 25 | 5'-lCs;dAs;lCs;dGs;dAs;lTs;lTs;dAs;lGs;dCs;lAs;lTs;lTs;lA-3' | 9 | 14 |
| 56 | 5'-lGs;dAs;lTs;lTs;dAs;lGs;dCs;lAs;lTs;lTs;lA-3' | 8 | 11 |
| 95 | 5'-dGs;dAs;lTs;lTs;dAs;lGs;dCs;lAs;lTs;lTs;lA-3' | 7 | 11 |
| 96 | 5'-lGs;lAs;lTs;lTs;dAs;lGs;dCs;lAs;lTs;lTs;lA-3' | 9 | 11 |
| 97 | 5'-lGs;dAs;dTs;lTs;dAs;lGs;dCs;lAs;lTs;lTs;lA-3' | 7 | 11 |
| 98 | 5'-lGs;dAs;lTs;dTs;dAs;lGs;dCs;lAs;lTs;lTs;lA-3' | 7 | 11 |
| 99 | 5'-lGs;dAs;lTs;lTs;lAs;lGs;dCs;lAs;lTs;lTs;lA-3' | 9 | 11 |
| 100 | 5'-lGs;dAs;lTs;lTs;dAs;dGs;dCs;lAs;lTs;lTs;lA-3' | 7 | 11 |
| 101 | 5'-lGs;dAs;lTs;lTs;dAs;lGs;lCs;lAs;lTs;lTs;lA-3' | 9 | 11 |
| 102 | 5'-lGs;dAs;lTs;lTs;dAs;lGs;dCs;dAs;lTs;lTs;lA-3' | 7 | 11 |
| 103 | 5'-lGs;dAs;lTs;lTs;dAs;lGs;dCs;lAs;dTs;lTs;lA-3' | 7 | 11 |
| 104 | 5'-lGs;dAs;lTs;lTs;dAs;lGs;dCs;lAs;lTs;dTs;lA-3' | 7 | 11 |
| 105 | 5'-lGs;dAs;lTs;lTs;dAs;lGs;dCs;lAs;lTs;lTs;dA-3' | 7 | 11 |

Figure 24A:
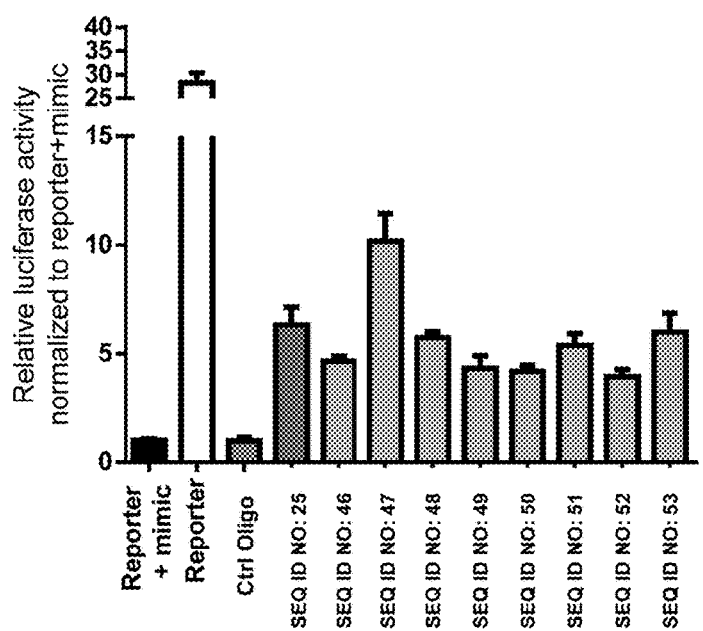
FIGS. 24A, 24B, 24C, and 24D show the antimiR-155 activity of oligonucleotide inhibitors containing locked nucleotide modifications at various positions, measured using a dual luciferase reporter plasmid containing the miR-155 binding site.
Figure 24B:
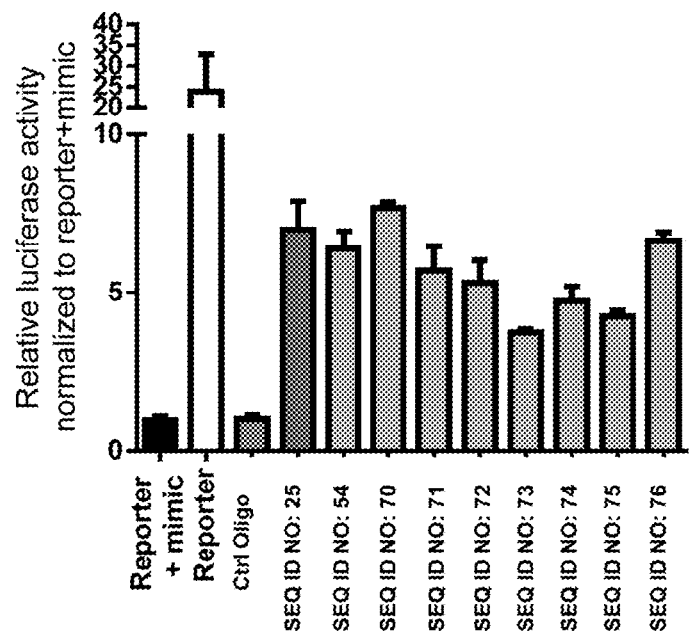
Figure 24C:
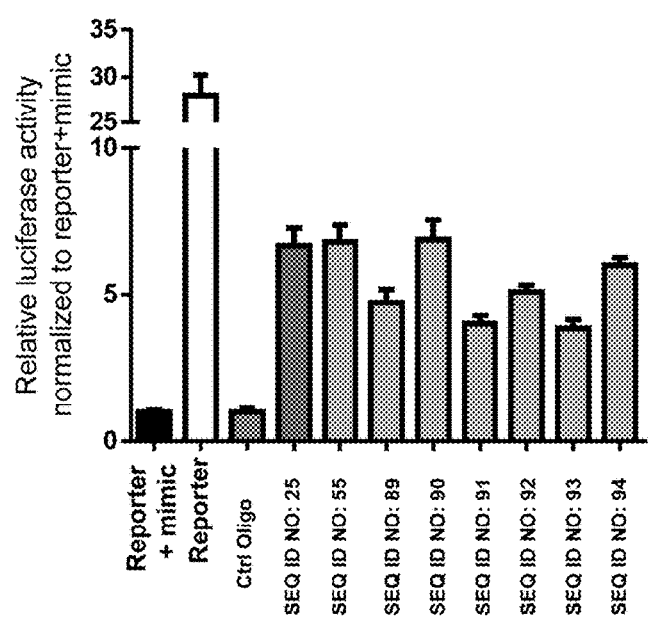
Figure 24D:
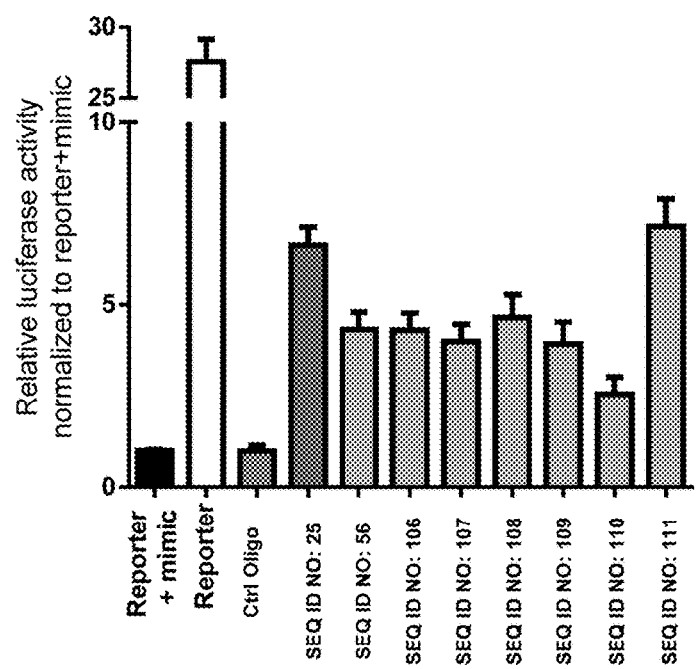

Example 9: AntimiR-155 Activity of Oligonucleotides Containing LNA Modifications at Various Positions The experiment was performed as described in Example 7. Test miR-155 oligonucleotide inhibitors used in this experiment differed in the position of LNA modifications (Tables 9-12). The results are shown in FIGS. 24A (Table 9), 24B (Table 10), 24C (Table 11), and 24D (Table 12).

TABLE 9

| SEQ ID NO. | Modified Sequence | LNA # | Length |
|---|---|---|---|
| 25 | 5'-lCs;dAs;lCs;dGs;dAs;lTs;lTs;dAs;lGs;dCs;lAs;lTs;lTs;lA-3' | 9 | 14 |
| 46 | 5'-dCs;lAs;lCs;dGs;dAs;lTs;lTs;dAs;lGs;dCs;lAs;lTs;lTs;lA-3' | 9 | 14 |
| 47 | 5'-lCs;lAs;dCs;dGs;dAs;lTs;lTs;dAs;lGs;dCs;lAs;lTs;lTs;lA-3' | 9 | 14 |
| 48 | 5'-lCs;dAs;dCs;lGs;dAs;lTs;lTs;dAs;lGs;dCs;lAs;lTs;lTs;lA-3' | 9 | 14 |
| 49 | 5'-lCs;dAs;lCs;dGs;lAs;dTs;lTs;dAs;lGs;dCs;lAs;lTs;lTs;lA-3' | 9 | 14 |
| 50 | 5'-lCs;dAs;lCs;dGs;dAs;lTs;dTs;lAs;lGs;dCs;lAs;lTs;lTs;lA-3' | 9 | 14 |
| 51 | 5'-lCs;dAs;lCs;dGs;dAs;lTs;lTs;lAs;dGs;dCs;lAs;lTs;lTs;lA-3' | 9 | 14 |
| 52 | 5'-lCs;dAs;lCs;dGs;dAs;lTs;lTs;dAs;dGs;lCs;lAs;lTs;lTs;lA-3' | 9 | 14 |
| 53 | 5'-lCs;dAs;lCs;dGs;dAs;lTs;lTs;dAs;lGs;lCs;dAs;lTs;lTs;lA-3' | 9 | 14 |

TABLE 10

| SEQ ID NO. | Modified Sequence | LNA # | Length |
|---|---|---|---|
| 25 | 5'-lCs;dAs;lCs;dGs;dAs;lTs;lTs;dAs;lGs;dCs;lAs;lTs;lTs;lA-3' | 9 | 14 |
| 54 | 5'-lAs;lCs;dGs;dAs;lTs;lTs;dAs;lGs;dCs;lAs;lTs;lTs;lA-3' | 9 | 13 |
| 70 | 5'-lAs;dCs;lGs;dAs;lTs;lTs;dAs;lGs;dCs;lAs;lTs;lTs;lA-3' | 9 | 13 |
| 71 | 5'-lAs;lCs;dGs;lAs;dTs;lTs;dAs;lGs;dCs;lAs;lTs;lTs;lA-3' | 9 | 13 |
| 72 | 5'-lAs;lCs;dGs;dAs;lTs;lTs;dAs;lGs;dCs;lAs;lTs;lTs;lA-3' | 9 | 13 |
| 73 | 5'-lAs;lCs;dGs;dAs;lTs;dTs;lAs;lGs;dCs;lAs;lTs;lTs;lA-3' | 9 | 13 |
| 74 | 5'-lAs;lCs;dGs;dAs;lTs;lTs;lAs;dGs;dCs;lAs;lTs;lTs;lA-3' | 9 | 13 |
| 75 | 5'-lAs;lCs;dGs;dAs;lTs;lTs;dAs;dGs;lCs;lAs;lTs;lTs;lA-3' | 9 | 13 |
| 76 | 5'-lAs;lCs;dGs;dAs;lTs;lTs;dAs;lGs;lCs;dAs;lTs;lTs;lA-3' | 9 | 13 |

TABLE 11

| SEQ ID NO. | Modified Sequence | LNA # | Length |
|---|---|---|---|
| 25 | 5'-lCs;dAs;lCs;dGs;dAs;lTs;lTs;dAs;lGs;dCs;lAs;lTs;lTs;lA-3' | 9 | 14 |
| 55 | 5'-lCs;dGs;dAs;lTs;lTs;dAs;lGs;dCs;lAs;lTs;lTs;lA-3' | 8 | 12 |
| 89 | 5'-dCs;lGs;dAs;lTs;lTs;dAs;lGs;dCs;lAs;lTs;lTs;lA-3' | 8 | 12 |
| 90 | 5'-lCs;dGs;lAs;dTs;lTs;dAs;lGs;dCs;lAs;lTs;lTs;lA-3' | 8 | 12 |
| 91 | 5'-lCs;dGs;dAs;lTs;dTs;lAs;lGs;dCs;lAs;lTs;lTs;lA-3' | 8 | 12 |
| 92 | 5'-lCs;dGs;dAs;lTs;lTs;lAs;dGs;dCs;lAs;lTs;lTs;lA-3' | 8 | 12 |
| 93 | 5'-lCs;dGs;dAs;lTs;lTs;dAs;dGs;lCs;lAs;lTs;lTs;lA-3' | 8 | 12 |
| 94 | 5'-lCs;dGs;dAs;lTs;lTs;dAs;lGs;lCs;dAs;lTs;lTs;lA-3' | 8 | 12 |

TABLE 12

| SEQ ID NO. | Modified Sequence | LNA # | Length |
|---|---|---|---|
| 25 | 5'-lCs;dAs;lCs;dGs;dAs;lTs;lTs;dAs;lGs;dCs;lAs;lTs;lTs;lA-3' | 9 | 14 |
| 56 | 5'-lGs;dAs;lTs;lTs;dAs;lGs;dCs;lAs;lTs;lTs;lA-3' | 8 | 11 |
| 106 | 5'-dGs;lAs;lTs;lTs;dAs;lGs;dCs;lAs;lTs;lTs;lA-3' | 8 | 11 |
| 107 | 5'-lGs;lAs;dTs;lTs;dAs;lGs;dCs;lAs;lTs;lTs;lA-3' | 8 | 11 |
| 108 | 5'-lGs;dAs;lTs;dTs;lAs;lGs;dCs;lAs;lTs;lTs;lA-3' | 8 | 11 |
| 109 | 5'-lGs;dAs;lTs;lTs;lAs;dGs;dCs;lAs;lTs;lTs;lA-3' | 8 | 11 |
| 110 | 5'-lGs;dAs;lTs;lTs;dAs;dGs;lCs;lAs;lTs;lTs;lA-3' | 8 | 11 |
| 111 | 5'-lGs;dAs;lTs;lTs;dAs;lGs;lCs;dAs;lTs;lTs;lA-3' | 8 | 11 |

Figure 25:
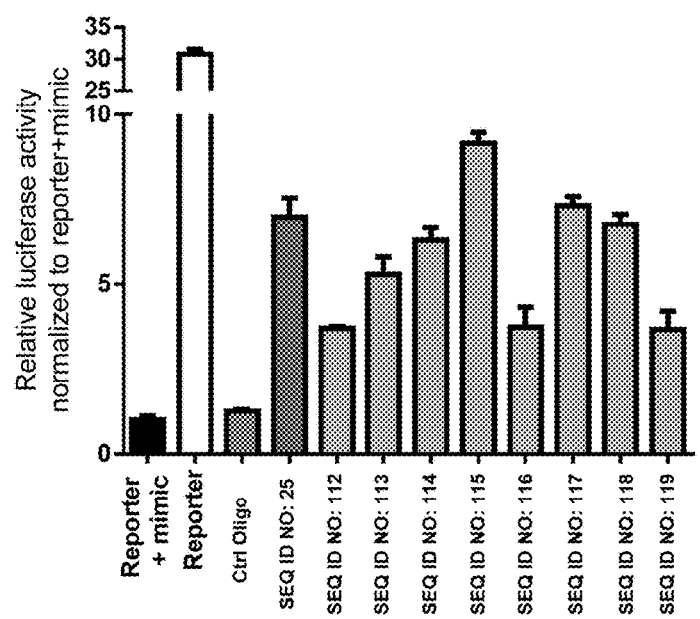
FIG. 25 shows the antimiR-155 activity of oligonucleotide inhibitors containing various nucleotide modifications, measured using a dual luciferase reporter plasmid containing the miR-155 binding site.

Example 10: AntimiR-155 Activity of Oligonucleotides Containing Various Nucleotide Modifications The experiment was performed as described in Example 7. Test miR-155 oligonucleotide inhibitors used in this experiment were 14 nucleotides in length and each contained 9 nucleotide modifications (Table 13). The nucleotide modifications included locked nucleotides (LNAs), ethylene-bridged nucleic acids/ethylene-bridged nucleotides (ENAs), and 2'-C-Bridged Bicyclic Nucleotide (CBBN). The results are shown in FIG. 25.

TABLE 13

| SEQ ID NO. | Modified Sequence | Mod # | Length |
|---|---|---|---|
| 25 | 5'-lCs;dAs;lCs;dGs;dAs;lTs;lTs;dAs;lGs;dCs;lAs;lTs;lTs;lA-3' | 9 | 14 |
| 112 | 5'-eCs;dAs;eCs;dGs;dAs;eTs;eTs;dAs;eGs;dCs;eAs;eTs;eTs;eA-3' | 9 | 14 |
| 113 | 5'-lCs;dAs;lCs;dGs;dAs;lTs;lTs;dAs;lGs;dCs;eAs;lTs;lTs;eA-3' | 9 | 14 |
| 114 | 5'-eCs;dAs;eCs;dGs;dAs;lTs;lTs;dAs;lGs;dCs;lAs;lTs;lTs;lA-3' | 9 | 14 |
| 115 | 5'-lCs;dAs;lCs;dGs;dAs;lTs;lTs;dAs;eGs;dCs;lAs;lTs;lTs;lA-3' | 9 | 14 |
| 116 | 5'-lCs;dAs;lCs;dGs;dAs;eTs;eTs;dAs;lGs;dCs;lAs;eTs;eTs;lA-3' | 9 | 14 |
| 117 | 5'-lCs;dAs;lCs;dGs;dAs;lTs;eTs;dAs;lGs;dCs;lAs;lTs;lTs;lA-3' | 9 | 14 |

TABLE 13-continued

| SEQ ID NO. | Modified Sequence | Mod # | Length |
|---|---|---|---|
| 118 | 5'-lCs;dAs;lCs;dGs;dAs;lTs;lTs;dAs;lGs;dCs;lAs;lTs;eTs;lA-3' | 9 | 14 |
| 119 | 5'-lCs;dAs;lCs;dGs;dAs;lTs;lTs;dAs;lGs;dCs;abAs;lTs;lTs;abA-3' | 9 | 14 | l = locked nucleotide; d = deoxyribonucleotide; s = phosphorothioate linkage; e = ethylene-bridged nucleotide; ab = amino-2'-C-Bridged Bicyclic Nucleotide (CBBN).

Example 11: AntimiR-155 Activity of 14-Nucleotide Long Oligonucleotides

Figure 26:
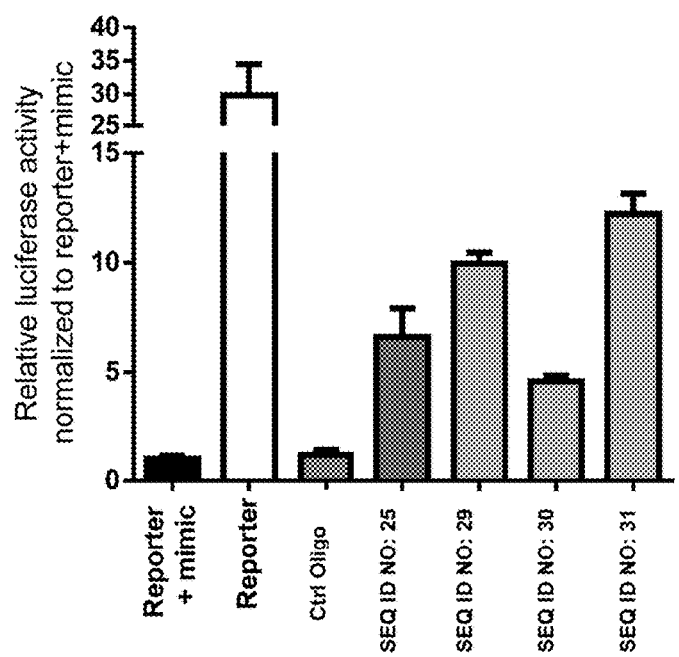
FIG. 26 shows the antimiR-155 activity of various 14-nucleotide long oligonucleotide inhibitors, measured using a dual luciferase reporter plasmid containing the miR-155 binding site.

The experiment was performed as described in Example 7. Test miR-155 oligonucleotide inhibitors used in this experiment were 14 nucleotides in length and contained 9 or 10 LNA modifications (Table 14). The results are shown in FIG. 26.

TABLE 14

| SEQ ID NO. | Modified Sequence | LNA # | Length |
|---|---|---|---|
| 25 | 5-lCs;dAs;lCs;dGs;dAs;lTs;lTs;dAs;lGs;dCs;lAs;lTs;lTs;lA-3' | 9 | 14 |
| 29 | 5-lCs;dAs;lCs;dGs;lAs;lTs;lTs;dAs;lGs;dCs;lAs;lTs;lTs;lA-3' | 10 | 14 |
| 30 | 5-lCs;dAs;lCs;dGs;lAs;dTs;lTs;dAs;lGs;dCs;lAs;lTs;lTs;lA-3' | 9 | 14 |
| 31 | 5-lCs;dAs;lCs;dGs;dAs;lTs;lTs;lAs;lGs;dCs;lAs;dTs;lTs;lA-3' | 9 | 14 |

Example 12: AntimiR-155 Activity of Oligonucleotide Inhibitors Containing SEQ ID NOs: 25 and 23

Figure 27:
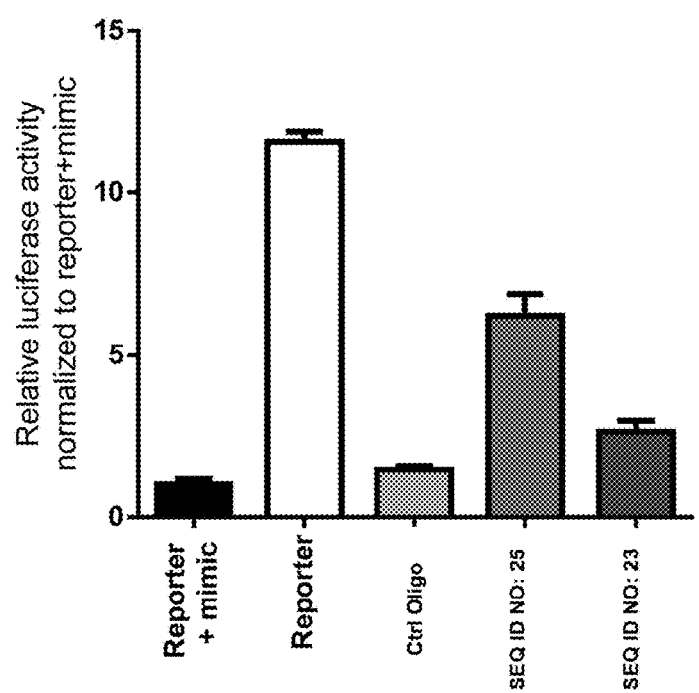
FIG. 27 shows the antimiR-155 activity of oligonucleotide inhibitors of SEQ ID NOs: 25 and 23, measured using a dual luciferase reporter plasmid containing the miR-155 binding site.

The experiment was performed as described in Example 7. Test miR-155 oligonucleotide inhibitors used in this experiment were oligonucleotide inhibitors of SEQ ID NOs: 25 and 23. The results are shown in FIG. 27.

Figure 28:
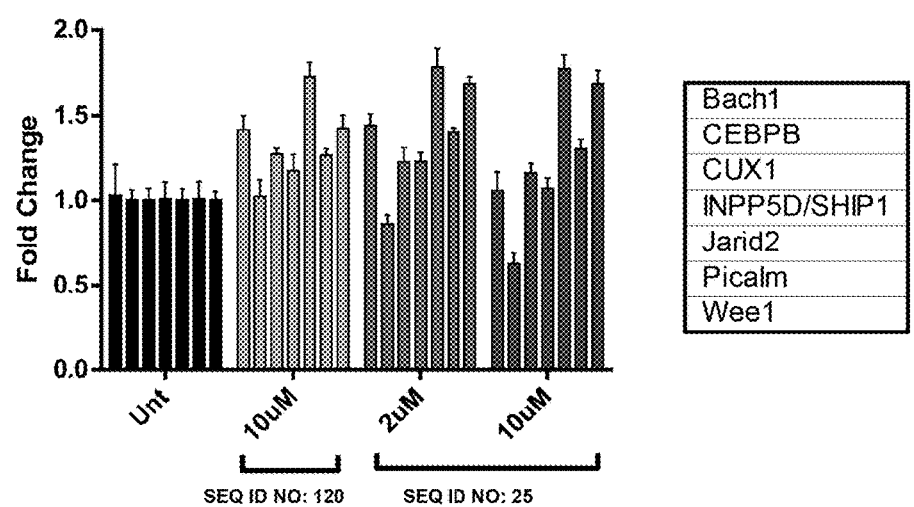
FIG. 28 shows the fold-change in the expression of miR-155 target genes in response to treatment with oligonucleotide inhibitors of SEQ ID NOs: 25 and 120.

Example 13: AntimiR-155 Activity of Oligonucleotide Inhibitors Containing SEQ ID NOs: 25 and 120 miR-155 oligonucleotide inhibitors of SEQ ID NOs: 25 and 120 were passively transfected in the Oci-Ly3 cell line. mRNA was isolated on Day 4 and was analyzed by qPCR for the expression of miR-155 target genes (Bach1, CEBPB, CUX1, INPP5D/SHIP1, Jarid2, Picalm, and Wee1). FIG. 28 shows the fold-change in the expression of these genes upon transfection of the oligonucleotide inhibitors of SEQ ID NOs: 25 and 120. The order of genes from left to right in each data point in FIG. 28 is Bach1, CEBPB, CUX1, INPP5D/SHIP1, Jarid2, Picalm, and Wee1. SEQ ID NO: 120 contains CBBN nucleotides in the same positions as the LNA in SEQ ID NO: 25.

---

The invention claimed is:

1. A method for treating a T cell lymphoma in a subject in need thereof, comprising administering to the subject an oligonucleotide inhibitor of miR-155 comprising the sequence of 5'-1Cs.dAs.1Cs.dGs.dAs.1Ts.1Ts.dAs.1Gs.dCs.1As.1Ts.1Ts.1A-3' (SEQ ID NO: 25), wherein 1 stands for a locked nucleotide; d stands for a deoxyribonucleotide; and s stands for a phosphorothioate linkage.

2. The method of claim 1, wherein administration of said oligonucleotide inhibitor reduces proliferation of T cell lymphoma cells.

3. The method of claim 2, wherein administration of said oligonucleotide inhibitor reduces proliferation of T cell lymphoma cells by about 30% compared to untreated cells.

4. The method of claim 2, wherein administration of said oligonucleotide inhibitor reduces proliferation of T cell lymphoma cells by about 40% compared to untreated cells.

5. The method of claim 2, wherein administration of said oligonucleotide inhibitor reduces proliferation of T cell lymphoma cells by about 50% compared to untreated cells.

6. The method of claim 2, wherein administration of said oligonucleotide inhibitor reduces proliferation of T cell lymphoma cells by about 60% compared to untreated cells.

7. The method of claim 2, wherein administration of said oligonucleotide inhibitor reduces proliferation of T cell lymphoma cells by about 70% compared to untreated cells.

8. The method of claim 2, wherein administration of said oligonucleotide inhibitor reduces proliferation of T cell lymphoma cells by about 80% compared to untreated cells.

9. The method of claim 2, wherein administration of said oligonucleotide inhibitor reduces proliferation of T cell lymphoma cells by about 90% compared to untreated cells.

10. The method of claim 1, wherein administration of said oligonucleotide inhibitor shows a dose-dependent inhibition of miR-155.

11. The method of claim 1, wherein administration of said oligonucleotide inhibitor induces apoptosis of T cell lymphoma cells.

12. The method of claim 1, wherein administration of said oligonucleotide inhibitor increases caspase activity in T cell lymphoma cells by at least about 2-fold compared to untreated cells.

13. The method of claim 1, wherein the T cell lymphoma is cutaneous T cell lymphoma (CTCL).

14. The method of claim 13, wherein the CTCL is mycosis fungoides (MF) sub-type.

15. The method of claim 13, wherein the CTCL is Sézary syndrome (SS) sub-type.

16. The method of claim 1, wherein said oligonucleotide inhibitor is administered to the subject via injection.

* * * * *